US008796205B2

(12) United States Patent
Jonassen et al.

(10) Patent No.: US 8,796,205 B2
(45) Date of Patent: *Aug. 5, 2014

(54) INSULIN DERIVATIVE

(75) Inventors: Ib Jonassen, Valby (DK); Patrick William Garibay, Holte (DK); Janos Tibor Kodra, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 499 days.

This patent is subject to a terminal disclaimer.

(21) Appl. No.: 12/297,914

(22) PCT Filed: May 8, 2007

(86) PCT No.: PCT/EP2007/054439
§ 371 (c)(1),
(2), (4) Date: Dec. 15, 2008

(87) PCT Pub. No.: WO2007/128815
PCT Pub. Date: Nov. 15, 2007

(65) Prior Publication Data
US 2009/0105121 A1  Apr. 23, 2009

Related U.S. Application Data

(60) Provisional application No. 60/835,225, filed on Aug. 3, 2006, provisional application No. 60/801,123, filed on May 17, 2006.

(30) Foreign Application Priority Data

May 9, 2006 (EP) .................................... 06113711
Aug. 1, 2006 (EP) .................................... 06118254

(51) Int. Cl.
A61K 38/28 (2006.01)
C07K 14/62 (2006.01)
A61K 38/00 (2006.01)

(52) U.S. Cl.
CPC C07K 14/62 (2013.01); A61K 38/00 (2013.01)
USPC ............... 514/5.9; 514/6.9; 530/303

(58) Field of Classification Search
CPC ................. A61K 38/28; C07K 14/62
See application file for complete search history.

(56) References Cited

U.S. PATENT DOCUMENTS

| | | | |
|---|---|---|---|
| 3,528,960 A | 9/1970 | Haas | |
| 5,478,575 A | 12/1995 | Miyazaki et al. | |
| 5,750,497 A | 5/1998 | Havelund et al. | |
| 5,898,067 A | 4/1999 | Balschmidt et al. | |
| 5,905,140 A | 5/1999 | Hansen | |
| 6,011,007 A | 1/2000 | Havelund et al. | |
| 6,174,856 B1 | 1/2001 | Langballe et al. | |
| 6,869,930 B1 | 3/2005 | Havelund et al. | |
| 7,615,532 B2 | 11/2009 | Jonassen et al. | |
| 8,003,605 B2 | 8/2011 | Bayer et al. | |
| 8,067,362 B2 | 11/2011 | Kodra et al. | |
| 2004/0138099 A1 | 7/2004 | Draeger | |
| 2006/0183667 A1 | 8/2006 | Jonassen et al. | |
| 2009/0074882 A1 | 3/2009 | Havelund et al. | |
| 2009/0137454 A1 | 5/2009 | Fynbo et al. | |
| 2009/0239784 A1 | 9/2009 | Jonassen et al. | |
| 2009/0239785 A1 | 9/2009 | Hubalek et al. | |
| 2010/0009899 A1 | 1/2010 | Jonassen et al. | |
| 2010/0167990 A1 | 7/2010 | Poulsen et al. | |
| 2010/0279931 A1 | 11/2010 | Garibay et al. | |
| 2011/0230402 A1 | 9/2011 | Johansen et al. | |
| 2011/0245163 A1 | 10/2011 | Jonassen et al. | |
| 2012/0035104 A1 | 2/2012 | Kodra et al. | |

FOREIGN PATENT DOCUMENTS

| | | |
|---|---|---|
| JP | H3-204823 | 9/1991 |
| JP | H6-506444 | 7/1994 |
| JP | H09502867 A | 3/1997 |
| JP | 2008-528659 | 7/2008 |
| JP | 2009-522231 | 6/2009 |
| JP | 2009-528325 | 8/2009 |
| JP | 2009-530242 | 8/2009 |
| WO | WO 92/12999 | 8/1992 |
| WO | WO 95/07931 | 3/1995 |
| WO | 2005/005477 A2 | 1/2005 |
| WO | WO 2005/012347 | 2/2005 |
| WO | 2005/047508 A1 | 5/2005 |
| WO | 2006/008238 A1 | 1/2006 |
| WO | WO 2006/082204 | 8/2006 |
| WO | 2007/074133 A2 | 7/2007 |
| WO | 2007/096431 A1 | 8/2007 |
| WO | 2007/128817 A2 | 11/2007 |
| WO | 2008/152106 A1 | 12/2008 |
| WO | 2009/060071 A1 | 5/2009 |
| WO | 2010/049488 A1 | 5/2010 |
| WO | 2011/141407 A1 | 11/2011 |

OTHER PUBLICATIONS

Definition of moiety from http://dictionary.reference.com/browse/moiety, pp. 1-3, Accessed Aug. 26, 2010.*
Dohle et al., "Copper-Mediated Cross-Coupling of Functionalized Arylmagnesium Reagents With Functionalized Alkyl and Beyzylic Halides", Organic Letters, 2001, vol. 3, No. 18, pp. 2871-2873.

* cited by examiner

*Primary Examiner* — James H Alstrum Acevedo
*Assistant Examiner* — Kaipeen Yang
(74) *Attorney, Agent, or Firm* — Richard W. Bork

(57) ABSTRACT

Novel human insulin derivatives are described which are soluble at physiological pH values and have a prolonged profile of action.

11 Claims, No Drawings

INSULIN DERIVATIVE

CROSS-REFERENCE TO RELATED APPLICATIONS

This application is a 35 U.S.C. §371 national stage application of International Patent Application PCT/EP2007/054439 (published as WO 2007/128815 A1), filed May 8, 2007, which claimed priority of European Patent Application 06113711.3, filed May 9, 2006 and European Patent Application 06118254.9, filed Aug. 1, 2006; this application further claims priority under 35 U.S.C. §119 of U.S. Provisional Application 60/801,123, filed May 17, 2006 and U.S. Provisional Application 60/835,225, filed Aug. 3, 2006.

FIELD OF THE INVENTION

The present invention relates to novel human insulin derivatives which are soluble at physiological pH values and have a prolonged profile of action. The invention also relates to pharmaceutical compositions containing such derivatives to methods of treating diabetes and hyperglycaemia using the insulin derivatives of the invention and to the use of such insulin derivatives in the treatment of diabetes and hyperglycaemia.

BACKGROUND OF THE INVENTION

Currently, the treatment of diabetes, both type 1 diabetes and type 2 diabetes, relies to an increasing extent on the so-called intensive insulin treatment. According to this regimen, the patients are treated with multiple daily insulin injections comprising one or two daily injections of a long acting insulin to cover the basal insulin requirement supplemented by bolus injections of a rapid acting insulin to cover the insulin requirement related to meals.

Long acting insulin compositions are well known in the art. Thus, one main type of long acting insulin compositions comprises injectable aqueous suspensions of insulin crystals or amorphous insulin. In these compositions, the insulin compounds utilized typically are protamine insulin, zinc insulin or protamine zinc insulin.

Certain drawbacks are associated with the use of insulin suspensions. Thus, in order to secure an accurate dosing, the insulin particles must be suspended homogeneously by gentle shaking before a defined volume of the suspension is withdrawn from a vial or expelled from a cartridge. Also, for the storage of insulin suspensions, the temperature must be kept within more narrow limits than for insulin solutions in order to avoid lump formation or coagulation.

WO 95/07931 (Novo Nordisk A/S) discloses human insulin derivatives wherein the ε-amino group of Lys$^{B29}$ has a lipophilic substituent. These insulin derivatives have a prolonged profile of action and are soluble at physiological pH values.

International patent application published under number WO 2005/012347 (Novo Nordisk A/S) concerns insulin derivatives which have a sidechain attached to either the α-amino group of the N-terminal amino acid residue of the B chain or the ε-amino group of a Lys residue present in the B chain.

International patent application No. EP2006/050593 (Novo Nordisk A/S) discloses insulin derivatives having at least one aromatic group in the side chain.

However, there is still a need for insulin having a more prolonged profile of action than the insulin derivatives known up till now.

SUMMARY OF THE INVENTION

The invention concerns an insulin derivative having a formula

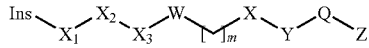

wherein Ins is a parent insulin moiety and $X_1$—$X_2$—$X_3$—W—$[CH_2]_m$—X—Y-Q-Z is a substituent and where the Ins is attached to the substituent via an amide bond between the α-amino group of the N-terminal amino acid residue of the B chain of Ins or an ε-amino group of a Lys residue present in the A or B chain of Ins and a CO-group in $X_1$, $X_2$ or $X_3$ of the substituent;

$X_1$ is:
—CO—$(CH_2)_n$ where n is 1, 2, 3, 4, 5 or 6;
—CO—$((CR^6R^7)_q$—NR—CO$)_{1-4}$—, where $R^6$ and $R^7$ independently of each other and independently for each value of q can be hydrogen, $C_{1-6}$-alkyl, $C_{2-6}$-alkenyl, $C_{2-6}$-alkynyl, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H, q is 1-6 and R is hydrogen, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H$_2$; $C_{1-6}$-alkyl, $C_{2-6}$-alkenyl; $C_{2-6}$-alkynyl or aryl or CH$_2$-aryl, in which the aryl group may be substituted with 1 or 2 groups selected from group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O) R$^2$ or —C(O)OR$^2$ or —OCH$_2$C(O) OR$^2$, where R$^2$ and R$^3$ independently are hydrogen, $C_{1-6}$-alkyl $C_{2-6}$-alkenyl or $C_{2-6}$-alkynyl, an amino acid amide residue of an amino acid with carboxylic acid in the side chain, or an amino acid with an uncharged side chain, or an amino acid with negatively charged side chain, which residue forms, with its carboxylic acid group, an amide bond together with the α-amino group of the N-terminal amino acid residue of the B chain of Ins or together with the ε-amino group of a Lys residue present in the A or B chain of Ins, a chain composed of two, three or four residues linked together via amide bonds in which the residues are chosen from the group consisting of: α-amino acid amide residues and amino acid residues as specified above, in which the chain—via an amide bond—is linked to the α-amino group of the N-terminal amino acid residue of the B chain of Ins or to the ε-amino group of a Lys residue present in the A or B chain of Ins, or a bond $X_2$ is:
—CO—
—COCH(R$^8$)—;
—COCH$_2$N(CH$_2$R$^8$)—;
—COCH$_2$N(CH$_2$R$^8$)COCH$_2$N(CH$_2$R$^8$)—;
—COCH$_2$CH$_2$N(CH$_2$CH$_2$R$^8$)—;
—COCH$_2$CH$_2$N(CH$_2$CH$_2$R$^8$)—COCH$_2$CH$_2$N (CH$_2$CH$_2$R$^8$)—;
—COCH$_2$N(CH$_2$CH$_2$R$^8$)—;
—COCH$_2$CH$_2$N(CH$_2$R$^8$)—; where R$^8$ can be COOH or CONH$_2$
—CO—((CH$_2$)$_{2-6}$—NH—CO)$_{1-4}$—;
—(CO—(CH$_2$)$_{2-6}$—CO—NH)$_{1-4}$—;
—(CO—(CR$^9$R$^{10}$)$_{1-6}$—CO—NH)$_{1-4}$—, where R$^9$ can be H, —COOH, —(CH$_2$)$_{1-6}$COOH, CH$_3$, —(CH$_2$)$_{1-6}$CH$_3$ or CONH$_2$ and R$^{10}$ can be H, —(CH$_2$)$_{1-6}$COOH, CH$_3$ or —(CH$_2$)$_{1-6}$CH$_3$;
a bond
provided that if an amine in X$_1$ or X$_2$ forms a bond with the rest of the substituent, the amine must be bound to the rest of the substituent via a carbonyl group.
X$_3$ is —C═O, provided that X$_3$ is only present if X$_1$ and X$_2$ are bonds.
W is:
arylene, which may be substituted with one, two, three or four groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;
heteroarylene, wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$-alkynyl, C(O)—C$_{1-6}$-alkyl, C(O)—C$_{2-6}$-alkenyl or C(O)—C$_{2-6}$-alkynyl for substitutions on nitrogen atoms, or
a bond
m is 0, 1, 2, 3, 4, 5 or 6;
X is
—O—;
—C═O;
—S—;
—S═O
—SO$_2$

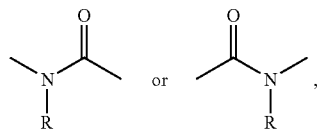

where R hydrogen, C$_{1-6}$-alkyl, C$_{2-6}$-alkenyl or C$_{2-6}$-alkynyl; or
a bond;
Y is
—(CR$^6$R$^7$)$_q$—NR$^1$—CO)$_{1-4}$—, where R$^6$ and R$^7$ independently of each other can be H, —COOH, or OH, q is 1-6 and R$^1$ is hydrogen, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H$_2$; C$_{1-6}$-alkyl, C$_{2-6}$-alkenyl; C$_{2-6}$-alkynyl or aryl or CH$_2$-aryl, in which the aryl group may be substituted with 1 or more groups selected from group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl;
—NCOR$^1$ where R$^1$ is defined as above; or
a bond;
Q is
a chain of the formula —(CH$_2$)$_{s1}$-Q$_1$-(CH$_2$)$_{s2}$-Q$_2$-(CH$_2$)$_{s3}$-Q$_3$-(CH$_2$)$_{s4}$-Q$_4$-(CH$_2$)$_{s5}$—; wherein Q$_1$-Q$_3$ independently of each other can be O, S, S(O), S(O)$_2$, P(O$_2$H), —O—P(O$_2$H)—O—, —N(COR$^2$)— or a bond; where R$^2$ is hydrogen, C$_{1-6}$-alkyl, C$_{2-6}$-alkenyl, C$_{2-6}$-alkynyl,
where Q$_4$ can be
arylene, which may be substituted with one or two groups selected from the group consisting —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$—NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds; or
heteroarylene, wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$—S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$- alkynyl, C(O)—$C_{1-6}$-alkyl, C(O)—$C_{2-6}$-alkenyl or C(O)—$C_{2-6}$-alkynyl for substitutions on nitrogen atoms;

and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that $Q_1$, $Q_2$ and $Q_3$ may not form bonds to each other and if s1, S2 and s3 are zero or 1, then no —$CH_2$— may be bound to 2 of the following atoms: O, N, S, or P, if $Q_4$ is arylene or heteroarylene, then it is not linked to the aliphatic chain via oxygen, if $Q_4$ is $C_6H_4$ then it is not linked to the aliphatic chain via sulphur;

and

Z is:
—COOH;
—CO-Asp;
—CO-Glu;
—CO-Gly;
—CO-Sar;
—$CH(COOH)_2$;
—$N(CH_2COOH)_2$;
—$SO_3H$
—$PO_3H_2$;
O—$SO_3H$;
O—$PO_3H_2$; or
tetrazo-5-lyl;
and any $Zn^{2+}$ complex thereof.

DEFINITIONS

By "insulin analogue" as used herein is meant a polypeptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residues can either be codable amino acid residues or other naturally occurring residues or purely synthetic amino acid residues In aspects of the invention a maximum of 17 amino acids have been modified. The insulin analogues may be such wherein position 28 of the B chain may be modified from the natural Pro residue to one of Asp, Lys, or Ile. In another aspect Lys at position B29 is modified to Pro. Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin; des(B30) human insulin analogues; insulin analogues wherein PheB1 has been deleted; insulin analogues wherein the A-chain and/or the B-chain have an N-terminal extension and insulin analogues wherein the A-chain and/or the B-chain have a C-terminal extension. Thus one or two Arg may be added to position B1.

In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

With "desB30 insulin", "desB30 human insulin" is meant a natural insulin or an analogue thereof lacking the B30 amino acid residue. Similarly, "desB29desB30 insulin" or "desB29desB30 human insulin" means a natural insulin or an analogue thereof lacking the B29 and B30 amino acid residues.

With "B1", "A1" etc. is meant the amino acid residue at position 1 in the B chain of insulin (counted from the N-terminal end) and the amino acid residue at position 1 in the A chain of insulin (counted from the N-terminal end), respectively. The amino acid residue in a specific position may also be denoted as e.g. PheB1 which means that the amino acid residue at position B1 is a phenylalanine residue.

With "insulin" as used herein is meant human insulin, porcine insulin or bovine insulin with disulfide bridges between CysA7 and CysB7 and between CysA20 and CysB19 and an internal disulfide bridge between CysA6 and CysA11.

By "parent insulin" is meant a naturally occurring insulin such as human insulin or porcine insulin. Alternatively, the parent insulin can be an insulin analogue.

The expression "uncharged" means that no group or groups that would assume a charge at pH interval 4 to 9 are present. For example no free carboxylic acids are present.

The expression "negatively charged" means that at least one group which would assume a negative charge at pH interval 4 to 9 is present.

When an insulin derivative according to the invention is stated to be "soluble at physiological pH values" it means that the insulin derivative can be used for preparing insulin compositions that are fully dissolved at physiological pH values. Such favourable solubility may either be due to the inherent properties of the insulin derivative alone or a result of a favourable interaction between the insulin derivative and one or more ingredients contained in the vehicle.

"Amino acid amide residue" means the alpha-carboxy amide of an amino acid, or if the amino acid contains a carboxylic acid in the side-chain, "amino acid amide" means amide of either the alpha-carboxy group, or amide of the side-chain carboxy group, as specified.

The term "arylene" as used herein is intended to include divalent carbocyclic aromatic ring systems such as phenylene, biphenylylene, naphthylene, anthracenylene, phenanthrenylene, fluorenylene, indenylene, pentalenylene, azulenylene and the like. Arylene is also intended to include the partially hydrogenated derivatives of the carbocyclic systems enumerated above. Non-limiting examples of such partially hydrogenated derivatives are 1,2,3,4-tetrahydronaphthylene, 1,4-dihydronaphthylene and the like. In an embodiment of the present invention "arylene" represents phenylene.

The term "heteroarylene" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, benzodioxanyl, benzoxanyl, methylenedioxybenzene, diphenyleneoxide, pyrrolinyl, pyrazolinyl, indolinyl, oxazolidinyl, oxazolinyl, oxazepinyl and the like.

In an embodiment of the present invention the term "heteroaryl" represents furyl, thienyl, thiazolyl, tetrazolyl, pyridyl, oxazolyl, 2,3-dihydrobenzofuranyl, benzodioxanyl, benzoxanyl, methylenedioxybenzene, diphenyleneoxide, pyrrolinyl, pyrazolinyl, indolinyl, oxazolidinyl, oxazolinyl, oxazepinyl.

"Halogen" designates an atom selected from the group consisting of F, Cl, Br and I.

The term "$C_{1-6}$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, Sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 2,4-hexadienyl and the like.

The following abbreviations have been used in the specification and examples:

| | |
|---|---|
| CV | column volume |
| EDTA | ethylene diamine tetraacetic acid |
| HI | human insulin |
| HPLC | High Performance Liquid Chromatography |
| HSA | human serum albumin |
| LC | liquid chromatography |
| MALDI | Matrix Assisted Laser Desorption Ionization |
| MS | mass spectrometry |
| NMP | N-methyl-2-pyrrolidone |
| RT | room temperature |
| SEC | size exclusion chromatography |
| SPA | Scitillation Proximity Assay |
| Tris | tris(hydroxymethyl)aminomethane |
| vol % | volume percentage |
| O.D. | optical density = absorbance |
| X2 monomer | AspB9 GluB27 human insulin |
| hGlu | homo-glutamic acid |
| Aad: | Alpha-amino-adipic acid (homoglutamic acid) |
| Bzl = Bn: | benzyl |
| DIEA: | N,N-diisopropylethylamine |
| DMF: | N,N-dimethylformamide |
| IDA: | Iminodiacetic acid |
| Sar: | Sarcosine (N-methyl-glycine) |
| tBu: | tert-butyl |
| HSTU: | O-(N-succinimidyl)-1,1,3,3-tetramethyluronium hexafluorophosphate |
| TSTU: | O-(N-succinimidyl)-1,1,3,3-tetramethyluronium tetrafluoroborate |
| THF: | Tetrahydrofuran |
| EtOAc: | Ethyl acetate |
| DIPEA: | Diisopropylethylamine |
| HOAt: | 1-Hydroxy-7-azabenzotriazole |
| TEA: | triethyl amine |
| Su: | N-succinimidyl = 2,5-dioxo-pyrrolidin-1-yl |
| TFA: | trifluoracetic acid |
| DCM: | dichloromethane |
| DMSO: | dimethyl sulphoxide |
| TLC: | Thin Layer Chromatography |
| RT: | room temperature |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

DESCRIPTION OF THE INVENTION

The present invention is based on the recognition that having a terminal aromatic group in a substituent in an insulin derivative molecule, plays an important role for the in vivo duration of action of prolonged-acting insulins, and for the mixability of prolonged-acting insulin with fast-acting insulin with no blunting.

Advantageously, insulin derivatives according to the invention are soluble at physiological pH values, have a potency which is comparable to that of human insulin, and are mixable with fast-acting insulins with no blunting. The individual profiles of action of mixed basal and bolus insulins are retained in formulations containing Zn(II) concentrations of up to or less than approximately 3 Zn(II) per insulin hexamer which limits the risk of precipitations in the formulation, compared to formulations containing more than 3 Zn (II) per insulin hexamer.

The invention relates to an insulin derivative having a formula

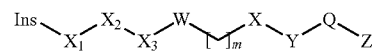

wherein Ins is a parent insulin moiety and $X_1$—$X_2$—$X_3$—W—$[CH_2]_m$—X—Y-Q-Z is a substituent and where the Ins is attached to the substituent via an amide bond between the α-amino group of the N-terminal amino acid residue of the B chain of Ins or an ε-amino group of a Lys residue present in the A or B chain of Ins and a CO-group in $X_1$, $X_2$ or $X_3$ of the substituent;

$X_1$ is:

—CO—$(CH_2)_n$ where n is 1, 2, 3, 4, 5 or 6;

—CO—$((CR^6R^7)_q$—NR—CO$)_{1-4}$—, where $R^6$ and $R^7$ independently of each other and independently for each value of q can be hydrogen, $C_{1-6}$-alkyl, $C_{2-6}$-alkenyl, $C_{2-6}$-alkynyl, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H, q is 1-6 and R is hydrogen, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H$_2$; $C_{1-6}$-alkyl, $C_{2-6}$-alkenyl; $C_{2-6}$-alkynyl or aryl or CH$_2$-aryl, in which the aryl group may be substituted with 1 or 2 groups selected from group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O) OR$^2$, where R$^2$ and R$^3$ independently are hydrogen, $C_{1-6}$-alkyl $C_{2-6}$-alkenyl or $C_{2-6}$-alkynyl, an amino acid amide residue of an amino acid with carboxylic acid in the side chain, or an amino acid with an uncharged side chain, or an amino acid with negatively charged side chain, which residue forms, with its carboxylic acid group, an amide bond together with the α-amino group of the N-terminal amino acid residue of the B chain of Ins or together with the ε-amino group of a Lys residue present in the A or B chain of Ins, a chain composed of two, three or four residues linked together via amide bonds in which the residues are chosen from the group consisting of: α-amino acid amide residues and amino acid residues as specified above, in which the chain—via an amide bond—is linked to the α-amino group of the N-terminal amino acid residue of the B chain of Ins or to the ε-amino group of a Lys residue present in the A or B chain of Ins, or a bond $X_2$ is:

—CO—

—COCH(R$^8$)—;

—COCH$_2$N(CH$_2$R$^8$)—;

—COCH$_2$N(CH$_2$R$^8$)COCH$_2$N(CH$_2$R$^8$)—;

—COCH$_2$CH$_2$N(CH$_2$CH$_2$R$^8$)—;

—COCH$_2$CH$_2$N(CH$_2$CH$_2$R$^8$)—COCH$_2$CH$_2$N(CH$_2$CH$_2$R$^8$)—;

—COCH$_2$N(CH$_2$CH$_2$R$^8$)—;

—COCH$_2$CH$_2$N(CH$_2$R$^8$)—; where R$^8$ can be COOH or CONH$_2$

—CO—$((CH_2)_{2-6}$—NH—CO$)_{1-4}$—;

—(CO—$(CH_2)_{2-6}$—CO—NH$)_{1-4}$—;

—(CO—$(CR^9R^{10})_{1-6}$—CO—NH$)_{1-4}$—, where R$^9$ can be H, —COOH, —$(CH_2)_{1-6}$COOH, CH$_3$, —$(CH_2)_{1-6}$CH$_3$ or CONH$_2$ and R$^{10}$ can be H, —$(CH_2)_{1-6}$COOH, CH$_3$ or —$(CH_2)_{1-6}$CH$_3$;

a bond provided that if an amine in $X_1$ or $X_2$ forms a bond with the rest of the substituent, the amine must be bound to the rest of the substituent via a carbonyl group.

$X_3$ is —C=O, provided that $X_3$ is only present if $X_1$ and $X_2$ are bonds.

W is:

arylene, which may be substituted with one, two, three or four groups selected from the group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, OCH$_2$C(O)R$^2$, —C(O)R$^2$ or —C(O)OR$^2$ or —OCH$_2$C(O)OR$^2$, where R$^2$ and R$^3$ independently are hydrogen, $C_{1-6}$-alkyl, $C_{2-6}$-alkenyl or $C_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;

heteroarylene, wherein the heteroarylene is substituted with one or two groups selected from the group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, $C_{1-6}$-alkyl, $C_{2-6}$-alkenyl or $C_{2-6}$-alkynyl for substitutions on carbon atoms, and selected from the group consisting of hydrogen, $C_{1-6}$-alkyl, $C_{2-6}$-alkenyl, $C_{2-6}$-alkynyl, C(O)—$C_{1-6}$-alkyl, C(O)—$C_{2-6}$-alkenyl or C(O)—$C_{2-6}$-alkynyl for substitutions on nitrogen atoms, or a bond m is 0, 1, 2, 3, 4, 5 or 6;

X is

—O—;

—C=O;

—S—

—S=O

—SO$_2$ or , where R hydrogen, $C_{1-6}$-alkyl, $C_{2-6}$-alkenyl or $C_{2-6}$-alkynyl; or a bond;

Y is

—$(CR^6R^7)_q$—NR$^1$—CO$)_{1-4}$—, where R$^6$ and R$^7$ independently of each other can be H, —COOH, or OH, q is 1-6 and R$^1$ is hydrogen, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H$_2$; $C_{1-6}$-alkyl, $C_{2-6}$-alkenyl; $C_{2-6}$-alkynyl or aryl or CH$_2$-aryl, in which the aryl group may be substituted with 1 or more groups selected from group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl;

—NCOR$^1$ where R$^1$ is defined as above; or a bond;

Q is a chain of the formula —(CH$_2$)$_{s1}$-Q$_1$-(CH$_2$)$_{s2}$-Q$_2$-(CH$_2$)$_{s3}$-Q$_3$-(CH$_2$)$_{s4}$-Q$_4$-(CH$_2$)$_{s5}$—; wherein Q$_1$-Q$_3$ independently of each other can be O, S, S(O), S(O)$_2$, P(O$_2$H), —O—P(O$_2$H)—O—, —N(COR$^2$)— or a bond; where R$^2$ is hydrogen, C$_{1-6}$-alkyl, C$_{2-6}$-alkenyl, C$_{2-6}$-alkynyl, where Q$_4$ can be arylene, which may be substituted with one or two groups selected from the group consisting —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds; or heteroarylene, wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$—S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$-alkynyl, C(O)—C$_{1-6}$-alkyl, C(O)—C$_{2-6}$-alkenyl or C(O)—C$_{2-6}$-alkynyl for substitutions on nitrogen atoms;

and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that Q$_1$, Q$_2$ and Q$_3$ may not form bonds to each other and if s1, S2 and s3 are zero or 1, then no —CH$_2$— may be bound to 2 of the following atoms: O, N, S, or P, if Q$_4$ is arylene or heteroarylene, then it is not linked to the aliphatic chain via oxygen, if Q$_4$ is C$_6$H$_4$ then it is not linked to the aliphatic chain via sulphur; and Z is:
—COOH;
—CO-Asp;
—CO-Glu;
—CO-Gly;
—CO-Sar;
—CH(COOH)$_2$;
—N(CH$_2$COOH)$_2$;
—SO$_3$H;
—PO$_3$H$_2$;
O—SO$_3$H;
O—PO$_3$H$_2$; or
tetrazo-5-lyl;

and any Zn$^{2+}$ complex thereof.

In one aspect the invention concerns an insulin derivative having a formula

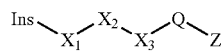

wherein Ins is a parent insulin moiety and X$_1$—X$_2$—X$_3$-Q-Z is a substituent and where the Ins is attached to the substituent via an amide bond between the α-amino group of the N-terminal amino acid residue of the B chain of Ins or an ε-amino group of a Lys residue present in the A or B chain of Ins and a CO-group in X$_1$, X$_2$ or X$_3$ of the substituent;

X$_1$ is:
—CO—(CH$_2$)$_n$ where n is 1, 2, 3, 4, 5 or 6;
—CO—((CR$^6$R$^7$)$_q$—NR—CO)$_{1-4}$—, where R$^3$ and R$^7$ independently of each other and independently for each value of q can be hydrogen, C$_{1-6}$-alkyl, C$_{2-6}$-alkenyl, C$_{2-6}$-alkynyl, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H, q is 1-6 and R is hydrogen, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H$_2$; C$_{1-6}$-alkyl, C$_{2-6}$-alkenyl; C$_{2-6}$-alkynyl or aryl or CH$_2$-aryl, in which the aryl group may be substituted with 1 or 2 groups selected from group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O) R$^2$ or —C(O)OR$^2$ or —OCH$_2$C(O) OR$^2$, where R$^2$ and R$^3$ independently are hydrogen, C$_{1-6}$-alkyl C$_{2-6}$-alkenyl or C$_{2-6}$-alkynyl, an amino acid amide residue of an amino acid with carboxylic acid in the side chain, or an amino acid with an uncharged side chain, or an amino acid with negatively charged side chain, which residue forms, with its carboxylic acid group, an amide bond together with the α-amino group of the N-terminal amino acid residue of the B chain of Ins or together with the ε-amino group of a Lys residue present in the A or B chain of Ins, a chain composed of two, three or four residues linked together via amide bonds in which the residues are chosen from the group consisting of: α-amino acid amide residues and amino acid residues as specified above, in which the chain—via an amide bond—is linked to the α-amino group of the N-terminal amino acid residue of the B chain of Ins or to the ε-amino group of a Lys residue present in the A or B chain of Ins, or a bond $X_2$ is:
—CO—
—COCH($R^8$)—;
—COCH$_2$N(CH$_2R^8$)—;
—COCH$_2$N(CH$_2R^8$)COCH$_2$N(CH$_2R^8$)—;
—COCH$_2$CH$_2$N(CH$_2$CH$_2R^8$)—;
—COCH$_2$CH$_2$N(CH$_2$CH$_2R^8$)—COCH$_2$CH$_2$N(CH$_2$CH$_2R^8$)—;
—COCH$_2$N(CH$_2$CH$_2R^8$)—;
—COCH$_2$CH$_2$N(CH$_2R^8$)—; where $R^8$ can be COOH or CONH$_2$
—CO—((CH$_2$)$_{2-6}$—NH—CO)$_{1-4}$—;
—(CO—(CH$_2$)$_{2-6}$—CO—NH)$_{1-4}$—;
—(CO—(CR$^9R^{10}$)$_{1-6}$—CO—NH)$_{1-4}$—, where $R^9$ can be H, —COOH, —(CH$_2$)$_{1-6}$COOH, CH$_3$, —(CH$_2$)$_{1-6}$CH$_3$ or CONH$_2$ and $R^{10}$ can be H, —(CH$_2$)$_{1-6}$COOH, CH$_3$ or —(CH$_2$)$_{1-6}$CH$_3$;

a bond provided that if an amine in $X_1$ or $X_2$ forms a bond with the rest of the substituent, the amine must be bound to the rest of the substituent via a carbonyl group.

$X_3$ is —C=O, provided that $X_3$ is only present if $X_1$ and $X_2$ are bonds.

Q is a chain of the formula —(CH$_2$)$_{s1}$-Q$_1$-(CH$_2$)$_{s2}$-Q$_2$-(CH$_2$)$_{s3}$-Q$_3$-(CH$_2$)$_{s4}$-Q$_4$-(CH$_2$)$_{s5}$—; wherein Q$_1$-Q$_3$ independently of each other can be O, S, S(O), S(O)$_2$, P(O$_2$H), —O—P(O$_2$H)—O—, —N(COR$^2$)— or a bond; where $R^2$ is hydrogen, C$_{1-6}$-alkyl, C$_{2-6}$-alkenyl, C$_{2-6}$-alkynyl, where Q$_4$ can be arylene, which may be substituted with one or two groups selected from the group consisting —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2R^3$, —S(O)NR$^2R^3$, —S(O)R$^2$, —S(O)$_2R^2$, —C(O)NR$^2R^3$, —OC(O)NR$^2R^3$, —NR$^2$C(O)R$^3$, —CH$_2$C(O)NR$^2R^3$, —OCH$_2$C(O)NR$^2R^3$, —OC(O)R$^2$, —OCH$_2$C(O)R$^2$, —C(O)R$^2$ or —C(O)OR$^2$ or —OCH$_2$C(O)OR$^2$, where $R^2$ and $R^3$ independently are hydrogen, C$_{1-6}$-alkyl, C$_{2-6}$-alkenyl or C$_{2-6}$-alkynyl; and when $R^2$ and $R^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds; or heteroarylene, wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2R^3$, —S(O)NR$^2R^3$, —S(O)R$^2$—S(O)$_2R^2$, —C(O)NR$^2R^3$, —OC(O)NR$^2R^3$, —NR$^2$C(O)R$^3$, —CH$_2$C(O)NR$^2R^3$, —OCH$_2$C(O)NR$^2R^3$, —OC(O)R$^2$, —OCH$_2$C(O)R$^2$—C(O)R$^2$ or —C(O)OR$^2$ or —OCH$_2$C(O)OR$^2$, where $R^2$ and $R^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$-alkynyl, C(O)—C$_{1-6}$-alkyl, C(O)—C$_{2-6}$-alkenyl or C(O)—C$_{2-6}$-alkynyl for substitutions on nitrogen atoms;

and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that Q$_1$, Q$_2$ and Q$_3$ may not form bonds to each other and if s1, S2 and s3 are zero or 1, then no —CH$_2$— may be bound to 2 of the following atoms: O, N, S, or P, if Q$_4$ is arylene or heteroarylene, then it is not linked to the aliphatic chain via oxygen, if Q$_4$ is C$_6$H$_4$ then it is not linked to the aliphatic chain via sulphur;

and

Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—PO$_3$H$_2$;
O—SO$_3$H;
O—PO$_3$H$_2$; or
tetrazo-5-lyl;

and any Zn$^{2+}$ complex thereof.

In one aspect the insulin derivative according to the invention is selected from the group consisting of:

N$^{εB29}$-(12-(4-carboxyphenyl) dodecanoyl-γ-Glu) desB30 insulin,

N$^{εB29}$-(-11-(4-carboxyphenyl) undecanoyl γ-Glu) desB30 insulin,

N$^{εB29}$-(12-(3-carboxyphenyl) dodecanoyl γ-Glu desB30 insulin,

N$^{εB29}$-(9-[4-(2-carboxyethyl) phenyl]nonanoyl) γ-Glu) desB30 insulin,

N$^{εB29}$-(4-[11-(4-carboxyphenyl) undecanoylamino]butyryl) desB30 insulin,

N$^{εB29}$-[12-(5-carboxythiophen-2-yl)dodecanoyl] desB30 insulin or

N$^{εB29}$-[12-(5-Carboxythiophen-2-yl)dodecanoyl-γ-Glu] desB30 insulin.

The invention will be summarized in the following paragraphs:

1. An Insulin derivative comprising a parent insulin and a substituent, wherein the substituent comprises a terminal group which is negatively charged at physiological pH; an aromatic group having 0, 1, 2 or 3 carbon atoms between the aromatic group and the terminal group; an aliphatic chain having at least 4 CH$_2$ groups; and a linker, wherein the aliphatic chain is bound to the parent insulin through the linker, with the proviso that 1) if the aromatic group is arylene or heteroarylene, then it is not linked to the aliphatic chain via oxygen and 2) if the aromatic group is C$_6$H$_4$ then it is not linked to the aliphatic chain via sulphur.

2. Insulin derivative according to paragraph 1, wherein the aromatic group is arylene or heteroarylene.

3. Insulin derivative according to paragraph 1 or 2, wherein the substituent comprises more than one aromatic group.

4. Insulin derivative according to paragraph 2, wherein the terminal group is —COOH.

5. Insulin derivative according to paragraph 2, wherein the arylene may be substituted with one or two groups selected from —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl.

6. Insulin derivative according to paragraph 5, wherein the arylene may be substituted with one or two groups selected from C$_{1-3}$-alkyl, C$_{2-3}$-alkenyl, C$_{2-3}$-alkynyl or —OR$^2$ where R$^2$ can be C$_{1-3}$-alkyl, C$_{2-3}$-alkenyl or C$_{2-3}$-alkynyl.

7. Insulin derivative according to paragraph 2, wherein the heteroarylene group comprises nitrogen, Sulphur or oxygen.

8. Insulin derivative according to paragraph 7, wherein the carbon or the nitrogen atoms may be substituted.

9. Insulin derivative according to paragraph 8 wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$—SR$^2$, —NR$^2$S(O)$_2$R$^3$—S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O) OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl C$_{2-6}$-alkenyl, C$_{2-6}$-alkynyl, C(O)—C$_{1-6}$-alkyl C(O)—C$_{2-6}$-alkenyl or C(O)—C$_{2-6}$-alkynyl for substitutions on nitrogen atoms.

10. Insulin derivative according to paragraphs 1-10, wherein the linker comprises 1-4 residues linked together via amide bonds chosen from the following: an amino acid amide residue of an amino acid with carboxylic acid in the side chain, or an amino acid with an uncharged side chain or an amino acid with a negatively charged side chain.

11. Insulin derivative according paragraph 10, wherein the linker is selected from the group consisting of β-D-Asp-amide, β-L-Asp-amide, γ-L-Glu-amide and γ-D-Glu-amide.

12. Insulin derivative according to paragraphs 1-11, wherein the linker comprises 1-4 amino acid residues linked together via amide bonds.

13. Insulin derivative according to paragraph 12, wherein the linker has at least one free carboxylic acid group or a group which is negatively charged at neutral pH.

14. Insulin derivative according to paragraphs 1-11, wherein the linker comprises 1-4 amino acid amide residues linked together via amide bonds.

15. Insulin derivative according to paragraph 1-11, wherein the linker comprises an amide.

16. Insulin derivative according to any of paragraphs 1-11, wherein the linker comprises an amide or a N-substituted amide of the formula —CONR$^4$R$^5$, —SONR$^4$R$^5$ or —SO$_2$NR$^4$R$^5$ where R$^4$ and R$^5$ independently of each other can be hydrogen, —CH$_3$, —CH$_{1-6}$CH$_3$, C$_{1-6}$-alkyl C$_{2-6}$-alkenyl or C$_{2-6}$-alkynyl and when R$^4$ and R$^5$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds.

17. Insulin derivative according to paragraph 16, where R$^4$ and R$^5$ are hydrogen.

18. An insulin derivative according to any of the preceeding paragraphs, wherein the substituent is attached to the ε-amino group of LysB29.

19. An insulin derivative having a formula

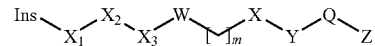

wherein Ins is a parent insulin moiety and X$_1$—X$_2$—X$_3$—W—[CH$_2$]$_m$—X—Y-Q-Z is a substituent and where the Ins is attached to the substituent via an amide bond between the α-amino group of the N-terminal amino acid residue of the B chain of Ins or an ε-amino group of a Lys residue present in the A or B chain of Ins and a CO-group in X$_1$, X$_2$ or X$_3$ of the substituent;

X$_1$ is:

—CO—(CH$_2$)$_n$ where n is 1, 2, 3, 4, 5 or 6;

—CO—((CR$^6$R$^7$)$_q$—NR—CO)$_{1-4}$—, where R$^6$ and R$^7$ independently of each other and independently for each value of q can be hydrogen, C$_{1-6}$-alkyl, C$_{2-6}$-alkenyl, C$_{2-6}$-alkynyl, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H, q is 1-6 and R is hydrogen, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H$_2$; C$_{1-6}$-alkyl, C$_{2-6}$-alkenyl; C$_{2-6}$-alkynyl or aryl or CH$_2$-aryl, in which the aryl group may be substituted with 1 or 2 groups selected from group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O) OR$^2$, where R$^2$ and R$^3$ independently are hydrogen, C$_{1-6}$-alkyl C$_{2-6}$-alkenyl or C$_{2-6}$-alkynyl, an amino acid amide residue of an amino acid with carboxylic acid in the side chain, or an amino acid with an uncharged side chain, or an amino acid with negatively charged side chain, which residue forms, with its carboxylic acid group, an amide bond together with the α-amino group of the N-terminal amino acid residue of the B chain of Ins or together with the ε-amino group of a Lys residue present in the A or B chain of Ins, a chain composed of two, three or four residues linked together via amide bonds in which the residues are chosen from the group consisting of: α-amino acid amide residues and amino acid residues as specified above, in which the chain—via an amide bond—is linked to the α-amino group of the N-terminal amino acid residue of the B chain of Ins or to the ε-amino group of a Lys residue present in the A or B chain of Ins, or a bond X$_2$ is:

—CO—

—COCH$_2$N(CH$_2$R$^8$)—;

—COCH$_2$N(CH$_2$R$^8$)COCH$_2$N(CH$_2$R$^8$)—;

—COCH₂CH₂N(CH₂CH₂R⁸)—;

—COCH₂CH₂N(CH₂CH₂R⁸)—COCH₂CH₂N(CH₂CH₂R⁸)—;

—COCH₂N(CH₂CH₂R⁸)—;

—COCH₂CH₂N(CH₂R⁸)—; where R⁸ can be COOH or CONH₂

—CO—((CH₂)₂₋₆—NH—CO)₁₋₄—;

—(CO—(CH₂)₂₋₆—CO—NH)₁₋₄—;

—(CO—(CR⁹R¹⁰)₁₋₆—CO—NH)₁₋₄—, where R⁹ can be H, —COOH, —(CH₂)₁₋₆COOH, CH₃, —(CH₂)₁₋₆CH₃ or CONH₂ and R¹⁰ can be H, —(CH₂)₁₋₆COOH, CH₃ or —(CH₂)₁₋₆CH₃; or a bond provided that if an amine in X₁ or X₂ forms a bond with the rest of the substituent, the amine must be bound to the rest of the substituent via a carbonyl group.

X₃ is —C=O, provided that X₃ is only present if X₁ and X₂ are bonds.

W is:

arylene, which may be substituted with one, two, three or four groups selected from the group consisting of —COOH, —CH₃, —SO₃H, —(CH₂)₁₋₆—SO₃H, —PO₃H₂, —(CH₂)₁₋₆—O—PO₃H₂, tetrazo-5-lyl or CONH₂, C₁₋₆-alkyl, C₂₋₆-alkenyl, C₂₋₆-alkynyl, hydrogen, halogen, —CN, —CF₃, —OCF₃, —S(O)₂CF₃, —SCF₃, —NO₂, —OR², —SR², —NR²S(O)₂R³, —S(O)₂NR²R³, —S(O)NR²R³, —S(O)R², —S(O)₂R², —C(O)NR²R³, —OC(O)NR²R³, —NR²C(O)R³, —CH₂C(O)NR²R³, —OCH₂C(O)NR²R³, —OC(O)R², —OCH₂C(O)R², —C(O)R² or —C(O)OR² or —OCH₂C(O)OR², where R² and R³ independently are hydrogen, C₁₋₆-alkyl, C₂₋₆-alkenyl or C₂₋₆-alkynyl; and when R² and R³ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;

heteroarylene, wherein the heteroarylene is substituted with one or two groups selected from the group consisting of —COOH, —CH₃, —SO₃H, —(CH₂)₁₋₆—SO₃H, —PO₃H₂, —(CH₂)₁₋₆—O—PO₃H₂, tetrazo-5-lyl or CONH₂, C₁₋₆-alkyl, C₂₋₆-alkenyl, C₂₋₆-alkynyl, hydrogen, halogen, —CN, —CF₃, —OCF₃, —S(O)₂CF₃, —SCF₃, —NO₂, —OR², —SR², —NR²S(O)₂R³, —S(O)₂NR²R³, —S(O)NR²R³, —S(O)R², —S(O)₂R², —C(O)NR²R³, —OC(O)NR²R³, —NR²C(O)R³, —CH₂C(O)NR²R³, —OCH₂C(O)NR²R³, —OC(O)R², OCH₂C(O)R²—C(O)R² or —C(O)OR² or —OCH₂C(O)OR², where R² and R³ independently are hydrogen, C₁₋₆-alkyl, C₂₋₆-alkenyl or C₂₋₆-alkynyl for substitutions on carbon atoms, and selected from the group consisting of hydrogen, C₁₋₆-alkyl, C₂₋₆-alkenyl, C₂₋₆-alkynyl, C(O)—C₁₋₆-alkyl, C(O)—C₂₋₆-alkenyl or C(O)—C₂₋₆-alkynyl for substitutions on nitrogen atoms, or a bond m is 0, 1, 2, 3, 4, 5 or 6;

X is

—O—;

—C=O;

—S—

—S=O

—SO₂

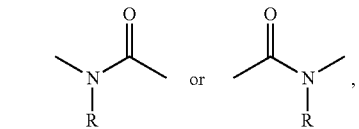

or where R hydrogen, C₁₋₆-alkyl, C₂₋₆-alkenyl or C₂₋₆-alkynyl; or a bond;

Y is

—(CR⁶R⁷)q—NR¹—CO)₁₋₄—, where R⁶ and R⁷ independently of each other can be H, —COOH, or OH, q is 1-6 and R¹ is hydrogen, —(CH₂)₁₋₆—COOH; —(CH₂)₁₋₆—CONH₂; —(CH₂)₁₋₆—SO₃H; —(CH₂)₁₋₆—PO₃H₂; —(CH₂)₁₋₆—O—SO₃H₂; —(CH₂)₁₋₆—O—PO₃H₂; C₁₋₆-alkyl, C₂₋₆-alkenyl; C₂₋₆-alkynyl or aryl or CH₂-aryl, in which the aryl group may be substituted with 1 or more groups selected from group consisting of —COOH, —CH₃, —SO₃H, —(CH₂)₁₋₆—SO₃H, —PO₃H₂, —(CH₂)₁₋₆—O—PO₃H₂, tetrazo-5-lyl or CONH₂, C₁₋₆-alkyl, C₂₋₆-alkenyl, C₂₋₆-alkynyl, hydrogen, halogen, —CN, —CF₃, —OCF₃, —S(O)₂CF₃, —SCF₃, —NO₂, —OR², —SR², —NR²S(O)₂R³, —S(O)₂NR²R³, —S(O)NR²R³, —S(O)R², —S(O)₂R², —C(O)NR²R³, —OC(O)NR²R³, —NR²C(O)R³, —CH₂C(O)NR²R³, —OCH₂C(O)NR²R³, —OC(O)R², —OCH₂C(O)R², —C(O)R² or —C(O)OR² or —OCH₂C(O)OR², where R² and R³ independently are hydrogen, C₁₋₆-alkyl, C₂₋₆-alkenyl or C₂₋₆-alkynyl;

—NCOR¹ where R¹ is defined as above; or a bond;

Q is a chain of the formula —(CH₂)s1-Q₁-(CH₂)s2-Q₂-(CH₂)s3-Q₃-(CH₂)s4-Q₄-(CH₂)s5—; wherein Q₁-Q₃ independently of each other can be O, S, S(O), S(O)₂, P(O₂H), —O—P(O₂H)—O—, —N(COR²)— or a bond; where R² is hydrogen, C₁₋₆-alkyl, C₂₋₆-alkenyl, C₂₋₆-alkynyl, where Q₄ can be arylene, which may be substituted with one or two groups selected from the group consisting —COOH, —CH₃, —SO₃H, —(CH₂)₁₋₆—SO₃H, —PO₃H₂, —(CH₂)₁₋₆—O—PO₃H₂, tetrazo-5-lyl or CONH₂, C₁₋₆-alkyl, C₂₋₆-alkenyl, C₂₋₆-alkynyl, hydrogen, halogen, —CN, —CF₃, —OCF₃, —S(O)₂CF₃, —SCF₃, —NO₂, —OR², —SR²—NR²S(O)₂R³, —S(O)₂NR²R³, —S(O)NR²R³, —S(O)R², —S(O)₂R², —C(O)NR²R³, —OC(O)NR²R³, —NR²C(O)R³, —CH₂C(O)NR²R³, —OCH₂C(O)NR²R³, —OC(O)R², —OCH₂C(O)R², —C(O)R² or —C(O)OR² or —OCH₂C(O)OR², where R² and R³ independently are hydrogen, C₁₋₆-alkyl, C₂₋₆-alkenyl or C₂₋₆-alkynyl; and when R² and R³ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds; or heteroarylene, wherein the heteroarylene is substituted with one or two groups selected from the group consisting of —COOH, —CH₃, —SO₃H, —(CH₂)₁₋₆—SO₃H, —PO₃H₂, —(CH₂)₁₋₆—O—PO₃H₂, tetrazo-5-lyl or CONH₂, C₁₋₆-alkyl, C₂₋₆-alkynyl, hydrogen, halogen, —CN, —CF₃, —OCF₃, —S(O)₂CF₃, —SCF₃, —NO₂, —OR², —SR², —NR²S(O)₂R³, —S(O)₂NR²R³, —S(O)NR²R³, —S(O)R²—S(O)₂R², —C(O)NR²R³, —OC(O)NR²R³, —NR²C(O)R³, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$-alkynyl, C(O)—C$_{1-6}$-alkyl, C(O)—C$_{2-6}$-alkenyl or C(O)—C$_{2-6}$-alkynyl for substitutions on nitrogen atoms;

and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that Q$_1$, Q$_2$ and Q$_3$ may not form bonds to each other and if s1, S2 and s3 are zero or 1, then no —CH$_2$— may be bound to 2 of the following atoms: O, N, S, or P, if Q$_4$ is arylene or heteroarylene, then it is not linked to the aliphatic chain via oxygen, if Q$_4$ is C$_6$H$_4$ then it is not linked to the aliphatic chain via sulphur;

and

Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—PO$_3$H$_2$;
O—SO$_3$H;
O—PO$_3$H$_2$; or
tetrazo-5-lyl;

and any Zn$^{2+}$ complex thereof.

20. An insulin derivative according to claim 19 having a formula

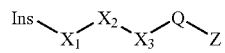

wherein Ins is a parent insulin moiety and X$_1$—X$_2$—X$_3$-Q-Z is a substituent and where the Ins is attached to the substituent via an amide bond between the α-amino group of the N-terminal amino acid residue of the B chain of Ins or an ε-amino group of a Lys residue present in the A or B chain of Ins and a CO-group in X$_1$, X$_2$ or X$_3$ of the substituent;

X$_1$ is:
—CO—(CH$_2$)$_n$ where n is 1, 2, 3, 4, 5 or 6;
—CO—((CR$^6$R$^7$)$_q$—NR—CO)$_{1-4}$—, where R$^6$ and R$^7$ independently of each other and independently for each value of q can be hydrogen, C$_{1-6}$-alkyl, C$_{2-6}$-alkenyl, C$_{2-6}$-alkynyl, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H, q is 1-6 and R is hydrogen, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H$_2$; C$_{1-6}$-alkyl, C$_{2-6}$-alkenyl; C$_{2-6}$-alkynyl or aryl or CH$_2$-aryl, in which the aryl group may be substituted with 1 or 2 groups selected from group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O) OR$^2$, where R$^2$ and R$^3$ independently are hydrogen, C$_{1-6}$-alkyl C$_{2-6}$-alkenyl or C$_{2-6}$-alkynyl, an amino acid amide residue of an amino acid with carboxylic acid in the side chain, or an amino acid with an uncharged side chain, or an amino acid with negatively charged side chain, which residue forms, with its carboxylic acid group, an amide bond together with the α-amino group of the N-terminal amino acid residue of the B chain of Ins or together with the ε-amino group of a Lys residue present in the A or B chain of Ins, a chain composed of two, three or four residues linked together via amide bonds in which the residues are chosen from the group consisting of: α-amino acid amide residues and amino acid residues as specified above, in which the chain—via an amide bond—is linked to the α-amino group of the N-terminal amino acid residue of the B chain of Ins or to the ε-amino group of a Lys residue present in the A or B chain of Ins, or a bond X$_2$ is:
—CO—
—COCH(R$^8$)—;
—COCH$_2$N(CH$_2$R$^8$)—;
—COCH$_2$N(CH$_2$R$^8$)COCH$_2$N(CH$_2$R$^8$)—;
—COCH$_2$CH$_2$N(CH$_2$CH$_2$R$^8$)—;
—COCH$_2$CH$_2$N(CH$_2$CH$_2$R$^8$)—COCH$_2$CH$_2$N(CH$_2$CH$_2$R$^8$)—;
—COCH$_2$N(CH$_2$CH$_2$R$^8$)—;
—COCH$_2$CH$_2$N(CH$_2$R$^8$)—; where R$^8$ can be COOH or CONH$_2$
—CO—((CH$_2$)$_{2-6}$—NH—CO)$_{1-4}$—;
—(CO—(CH$_2$)$_{2-6}$—CO—NH)$_{1-4}$—;
—(CO—(CR$^9$R$^{10}$)$_{1-6}$—CO—NH)$_{1-4}$—, where R$^9$ can be H, —COOH, —(CH$_2$)$_{1-6}$COOH, CH$_3$, —(CH$_2$)$_{1-6}$CH$_3$ or CONH$_2$ and R$^{10}$ can be H, —(CH$_2$)$_{1-6}$COOH, CH$_3$ or —(CH$_2$)$_{1-6}$CH$_3$;

a bond provided that if an amine in X$_1$ or X$_2$ forms a bond with the rest of the substituent, the amine must be bound to the rest of the substituent via a carbonyl group.

X$_3$ is —C=O, provided that X$_3$ is only present if X$_1$ and X$_2$ are bonds.

Q is a chain of the formula —(CH$_2$)$_{s1}$-Q$_1$-(CH$_2$)$_{s2}$-Q$_2$-(CH$_2$)$_{s3}$-Q$_3$-(CH$_2$)$_{s4}$-Q$_4$-(CH$_2$)$_{s5}$—; wherein Q$_1$-Q$_3$ independently of each other can be O, S, S(O), S(O)$_2$, P(O$_2$H), —O—P(O$_2$H)—O—, —N(COR$^2$)— or a bond; where R$^2$ is hydrogen, C$_{1-6}$-alkyl, C$_{2-6}$-alkenyl, C$_{2-6}$-alkynyl, where Q$_4$ can be arylene, which may be substituted with one or two groups selected from the group consisting —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$—NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds; or heteroarylene, wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$—S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$-alkynyl, C(O)—C$_{1-6}$-alkyl, C(O)—C$_{2-6}$-alkenyl or C(O)—C$_{2-6}$-alkynyl for substitutions on nitrogen atoms;

and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that Q$_1$, Q$_2$ and Q$_3$ may not form bonds to each other and if s1, S2 and s3 are zero or 1, then no —CH$_2$— may be bound to 2 of the following atoms: O, N, S, or P, if Q$_4$ is arylene or heteroarylene, then it is not linked to the aliphatic chain via oxygen, if Q$_4$ is C$_6$H$_4$ then it is not linked to the aliphatic chain via sulphur;

and

Z is:
  —COOH;
  —CO-Asp;
  —CO-Glu;
  —CO-Gly;
  —CO-Sar;
  —CH(COOH)$_2$;
  —N(CH$_2$COOH)$_2$;
  —SO$_3$H
  —PO$_3$H$_2$;
  O—SO$_3$H;
  O—PO$_3$H$_2$; or
  tetrazo-5-lyl;
and any Zn$^{2+}$ complex thereof.

21. Insulin derivative according to paragraph 19-20, wherein X$_1$ is an amino acid amide residue of an amino acid with carboxylic acid in the side chain.

22. Insulin derivative according to any of paragraphs 19-21, wherein X$_1$ is selected from the group consisting of β-D-Asp-amide, β-L-Asp-amide, γ-L-Glu-amide and γ-D-Glu-amide.

23. Insulin derivative according to paragraph 19-20, wherein X$_1$ is a chain composed of two, three or four amino acid amide residues of amino acids with carboxylic acids in their side chain.

24. Insulin derivative according to paragraphs 19-20 or 23, wherein X$_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

25. Insulin derivative according to paragraph 19-20, wherein X$_1$ is an amino acid residue having from 2 to 10 carbon atoms.

26. Insulin derivative according to paragraph 25, wherein X$_1$ is selected from the group consisting of α-Asp, β-Asp, α-Glu, γ-Glu, α-hGlu and δ-hGlu.

27. Insulin derivative according to paragraph 25, wherein X$_1$ is γ-Glu.

28. Insulin derivative according to paragraph 19-20, wherein X$_1$ is a chain composed of two, three or four residues selected from the group consisting of an amino acid amide residue of an amino acid with carboxylic acid in the side chain, an amino acid with an uncharged side chain and an amino acid with a negatively charged side chain.

29. Insulin derivative according to paragraph 28, wherein X$_1$ is a chain composed of two α-amino acid residues of which one has from 4 to 10 carbon atoms and a free carboxylic acid group while the other has from 2 to 11 carbon atoms but no free carboxylic acid group.

30. Insulin derivative according to paragraph 29, wherein X$_1$ is selected from the group consisting of α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

31. Insulin derivative according to paragraph 28, wherein X$_1$ is a chain composed of two α-amino acid residues independently having from 4 to 10 carbon atoms and both having a free carboxylic acid group.

32. Insulin derivative according to paragraph 31, wherein X$_1$ is selected from the group consisting of α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp; α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

33. Insulin derivative according to paragraph 19-20, wherein X$_1$ is —CO—((CR$^6$R$^7$)$_q$—NR—CO)$_{1-4}$—, where R$^6$ and R$^7$ independently of each other and independently for each value of q can be hydrogen, C$_{1-6}$-alkyl, C$_{2-6}$-alkenyl, C$_{2-6}$-alkynyl, —(CH$_2$)$_{1-6}$—COOH; —(CH$_2$)$_{1-6}$—CONH$_2$; —(CH$_2$)$_{1-6}$—SO$_3$H$_2$; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H, q is 1-6 and R is hydrogen, —(CH$_2$)$_{1-6}$—COOH; —(CH$_2$)$_{1-6}$—CONH$_2$; —(CH$_2$)$_{1-6}$—SO$_3$H; —(CH$_2$)$_{1-6}$—PO$_3$H$_2$; —(CH$_2$)$_{1-6}$—O—SO$_3$H$_2$; —(CH$_2$)$_{1-6}$—O—PO$_3$H$_2$; C$_{1-6}$-alkyl, C$_{2-6}$-alkenyl; C$_{2-6}$-alkynyl or aryl or CH$_2$-aryl, in which the aryl group may be substituted with 1 or 2 groups selected from group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O) OR$^2$, where R$^2$ and R$^3$ independently are hydrogen, C$_{1-6}$-alkyl C$_{2-6}$-alkenyl or C$_{2-6}$-alkynyl, 34. Insulin derivative according to paragraph 33, wherein $X_1$ is —CO—$(CH_2)_2$—(CH COOH)—NH—CO—.

35. Insulin derivative according to any of paragraphs 19-34, wherein $X_2$ is a bond 36. Insulin derivative according to paragraph 19-20, wherein $X_2$ is:
—CO—
—COCH$_2$N(CH$_2$R$^8$)—;
—COCH$_2$N(CH$_2$R$^8$)COCH$_2$N(CH$_2$R$^8$)—;
—COCH$_2$CH$_2$N(CH$_2$CH$_2$R$^8$)—;
—COCH$_2$CH$_2$N(CH$_2$CH$_2$R$^8$)—COCH$_2$CH$_2$N(CH$_2$CH$_2$R$^8$)—;
—COCH$_2$N(CH$_2$CH$_2$R$^8$)—;
—COCH$_2$CH$_2$N(CH$_2$R$^8$)—; where R$^8$ can be COOH or CONH$_2$
—CO—$((CH_2)_{2-6}$—NH—CO)$_{1-4}$—;
—(CO—$(CH_2)_{2-6}$—CO—NH)$_{1-4}$—;
—(CO—(CR$^9$R$^{10}$)$_{1-6}$—CO—NH)$_{1-4}$—, where R$^9$ can be H, —COOH, —(CH$_2$)$_{1-6}$COOH, CH$_3$, —(CH$_2$)$_{1-6}$CH$_3$ or CONH$_2$ and R$^{10}$ can be H, —(CH$_2$)$_{1-6}$COOH, CH$_3$ or —(CH$_2$)$_{1-6}$CH$_3$;
a bond 37. Insulin derivative according to paragraph 36, wherein $X_2$ is selected from the group consisting of —(CO—(CH$_2$)$_2$—NH—CO) 1- or —(CO—(CH$_2$)$_3$—NH—CO)$_1$—.

38. Insulin derivative according to paragraphs 36, wherein $X_2$ is —CO—.

39. Insulin derivative according to paragraphs 36-38, wherein $X_1$ is a bond.

40. Insulin derivative according to paragraphs 19 and 21-39, wherein W is phenylene.

41. Insulin derivative according to paragraph 40, wherein W is 5-7 membered heterocyclic ring system comprising nitrogen, oxygen or sulphur.

42. Insulin derivative according to paragraph 41, wherein W is a 5 membered heterocyclic ring system comprising at least one oxygen or sulphur.

43. Insulin derivative according to paragraphs 19 and 21-39, wherein W is a bond 44. Insulin derivative according to paragraphs 19 and 21-43, wherein m is 0, 1 or 2.

45. Insulin derivative according to paragraphs 19 and 21-44, wherein X is —CO— or a bond.

46. Insulin derivative according to paragraphs 19 and 21-45, wherein Y is a bond.

47. Insulin derivative according to any of paragraphs 19-46, wherein Q is a chain of the formula —(CH$_2$)$_{s1}$-Q$_1$-(CH$_2$)$_{s2}$-Q$_2$-(CH$_2$)$_{s3}$-Q$_3$-(CH$_2$)$_{s4}$-Q$_4$-(CH$_2$)$_{s5}$—; wherein Q$_1$-Q$_3$ independently of each other can be O, S, S(O), S(O)$_2$, P(O$_2$H), —O—P(O$_2$H)—O—, —N(COR$^2$)— or a bond; where R$^2$ is hydrogen, C$_{1-6}$-alkyl, C$_{2-6}$-alkenyl, C$_{2-6}$-alkynyl, where Q$_4$ can be
arylene, which may be substituted with one or two groups selected from the group consisting —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds; or
heteroarylene, wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$—S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$-alkynyl, C(O)—C$_{1-6}$-alkyl, C(O)—C$_{2-6}$-alkenyl or C(O)—C$_{2-6}$-alkynyl for substitutions on nitrogen atoms;
and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that Q$_1$, Q$_2$ and Q$_3$ may not form bonds to each other and if s1, s2 and s3 are zero or 1, then no —CH$_2$— may be bound to 2 of the following atoms: O, N, S, or P.

48. Insulin derivative according to paragraph 47, wherein Q$_4$ is arylene.

49. Insulin derivative according to paragraphs 47 or 48, wherein Q$_4$ is C$_6$H$_4$.

50. Insulin derivative according to paragraphs 47 or 48, wherein Q$_4$ is arylene, which may be substituted with one or two groups selected from the group consisting —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl C$_{2-6}$-alkenyl or C$_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds.

51. Insulin derivative according to paragraph 47, wherein Q$_4$ is heteroarylene.

52. Insulin derivative according to paragraph 51, wherein the heteroarylene group comprises nitrogen, Sulphur or oxygen.

53. Insulin derivative according to paragraph 51, wherein the heteroarylene, wherein the heteroarylene is substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$^2$R$^3$, —S(O)R$^2$—S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl for substitutions on carbon atoms, and selected from the group consisting of hydrogen, C$_{1-6}$-alkyl, C$_{2-6}$-alkenyl, C$_{2-6}$-alkynyl, C(O)—C$_{1-6}$-alkyl, C(O)—C$_{2-6}$-alkenyl or C(O)—C$_{2-6}$-alkynyl for substitutions on nitrogen atoms.

54. Insulin derivative according to paragraphs 46-53, wherein Q$_4$ is a 5-7 membered ring system.

55. Insulin derivative according to paragraphs 54, wherein Q$_4$ is a 5 membered ring system.

56. Insulin derivative according to paragraphs 46-55, wherein Q$_4$ is a bicyclic system.

57. Insulin derivative according to paragraph 56, wherein the bicyclic system contains two 5-7 membered ring system.

58. Insulin derivative according to paragraphs 57, wherein the bicyclic system contains one 6 membered ring and one 5 membered ring, where the 5 membered ring can comprise nitrogen, oxygen or sulphur.

59. Insulin derivative according paragraphs 56-58, wherein the bicyclic system consist of a 6 membered and a 5 membered ring and where the 5 membered ring is at the terminal end of the substituent.

60. Insulin derivative according to paragraph 59, wherein Z is not present in the substituent.

61. Insulin derivative according to paragraph 60, wherein the 6 membered ring comprises nitrogen.

62. Insulin derivative according to paragraphs 46-61, wherein Q$_1$, Q$_2$ and Q$_3$ are all bonds.

63. Insulin derivative according to paragraphs 46-62, wherein s2, S3 and s4 are one.

64. Insulin derivative according to paragraphs 46-63, wherein s1 is 5, 6, 7 or 8 and s5 is 0, 1 or 2.

65. Insulin derivative according to paragraphs 46-64, wherein s5 is 0.

66. Insulin derivative according to paragraphs 46-64, wherein s5 is 1 or 2.

67. Insulin derivative according paragraphs 46-61 and paragraphs 63-66, wherein
Q$_1$ and Q$_2$ are oxygen.

68. Insulin derivative according paragraphs 19-59 and 61-67, wherein Z is —COOH.

69. Insulin derivative according paragraphs 19-59 and 61-67, wherein Z is —CO-Asp.

70. Insulin derivative according paragraphs 19-59 and 61-67, wherein Z is —CO-Glu.

71. Insulin derivative according paragraphs 19-59 and 61-67, wherein Z is —CO-Gly.

72. Insulin derivative according paragraphs 19-59 and 61-67, wherein Z is —CO-Sar.

73. Insulin derivative according paragraphs 19-59 and 61-67, wherein Z is —CH(COOH)$_2$.

74. Insulin derivative according paragraphs 19-59 and 61-67, wherein Z is —N(CH$_2$COOH)$_2$.

75. Insulin derivative according paragraphs 19-59 and 61-67, wherein Z is —SO$_3$H.

76. Insulin derivative according paragraphs 19-59 and 61-67, wherein Z is —PO$_3$H$_2$.

77. Insulin derivative according paragraphs 19-59 and 61-67, wherein Z is O—SO$_3$H.

78. Insulin derivative according paragraphs 19-59 and 61-67, wherein Z is O—PO$_3$H$_2$.

79. Insulin derivative according paragraphs 19-59 and 61-67, wherein Z is tetrazo-5-lyl.

80. Insulin derivative according to any of the paragraphs 1-79, wherein the parent insulin is human insulin or porcine insulin or an insulin analogue.

81. Insulin derivative according to any of paragraphs 79-80, wherein the amino acid residue at position B30 of the parent insulin is Lys or has been deleted.

82. Insulin derivative according to paragraph 81, wherein the parent insulin is desB30 human insulin.

83. Insulin derivative according to any of paragraphs 79-82, wherein the amino acid residue at position B1 of the parent insulin has been deleted.

84. Insulin derivative according to any of paragraphs 79-83, wherein the amino acid residue in position A21 of the parent insulin is Gly or Asn.

85. Insulin derivative according to any of paragraphs 79-84, wherein the amino acid residue at position B3 of the parent insulin is Lys 86. Insulin derivative according to any of paragraphs 79-85, wherein the amino acid residue at position B28 of the parent insulin is Asp or Lys.

87. Insulin derivative according to any of paragraphs 79-86, wherein the amino acid residue at position B29 of the parent insulin is Pro or Thr.

88. Insulin derivative according to paragraph 86, wherein the parent insulin is AspB28 human insulin.

89. Insulin derivative according to paragraph 84, wherein the parent insulin is GlyA21 human insulin or GlyA21desB30 human insulin or GlyA21ArgB31ArgB32 human insulin.

90. Insulin derivative according to paragraph 85, wherein the parent insulin is LysB3GluB29 human insulin.

91. Insulin derivative according to paragraph 86-87, wherein the parent insulin is LysB28ProB29 human insulin 92. Insulin derivative according to paragraph 81 and 87, wherein the parent insulin is ThrB29LysB30 human insulin 93. A zinc complex of an insulin derivative according to any one of the preceding paragraphs wherein the insulin derivative binds two zinc ions, three zinc ions four zinc ions, five zinc ions, Six zinc ions, Seven zinc ions, eight zinc ions, nine zinc ions or ten zinc ions per 6 insulin derivatives.

94. A pharmaceutical composition for the treatment of diabetes in a patient in need of such treatment, comprising a therapeutically effective amount of an insulin derivative according to any of the preceeding paragraphs together with a pharmaceutically acceptable carrier.

95. A pharmaceutical composition for the treatment of diabetes in a patient in need of such treatment, comprising a therapeutically effective amount of an insulin derivative according to any of the preceeding paragraphs in mixture with an insulin or an insulin analogue which has a rapid onset of action, together with a pharmaceutically acceptable carrier.

96. A method of treating diabetes in a patient in need of such a treatment, comprising administering to the patient a therapeutically effective amount of an insulin derivative according to any of the preceeding paragraphs together with a pharmaceutically acceptable carrier.

97. A method of treating diabetes in a patient in need of such a treatment, comprising administering to the patient a therapeutically effective amount of an insulin derivative according to any of the preceeding paragraphs in mixture with an insulin or an insulin analogue which has a rapid onset of action, together with a pharmaceutically acceptable carrier.

98. A method according to paragraphs 98 or 99 for pulmonary treatment of diabetes 99. A mixture of an insulin derivative according to any of paragraphs 1-95 and a rapid acting insulin analogue selected group consisting of AspB28 human insulin; LysB28ProB29 human insulin and LysB3GluB29 human insulin.

1. An insulin derivative according to any of paragraphs 1-95 selected from the group consisting of $N^{\epsilon B29}$-(12-(4-carboxyphenyl) dodecanoyl-γ-Glu) desB30 insulin, $N^{\epsilon B29}$-(-11-(4-carboxyphenyl) undecanoyl γ-Glu) desB30 insulin, $N^{\epsilon B29}$-(12-(3-carboxyphenyl) dodecanoyl γ-Glu desB30 insulin, $N^{\epsilon B29}$-(9-[4-(2-carboxyethyl) phenyl]nonanoyl) γ-Glu) desB30 insulin, $N^{\epsilon B29}$-(4-[11-(4-carboxyphenyl) undecanoylamino]butyryl) desB30 insulin, $N^{\epsilon B29}$-[12-(5-carboxythiophen-2-yl)dodecanoyl] desB30 insulin or $N^{\epsilon B29}$-[12-(5-carboxythiophen-2-yl)dodecanoyl-γ-Glu] desB30 insulin.

101. Insulin derivative as described in the examples.

In one aspect of the invention $X_1$ is a chain composed of two, three or four residues selected from the group consisting of an amino acid amide residue of an amino acid with carboxylic acid in the side chain, an amino acid with an uncharged side chain and an amino acid with a negatively charged side chain. $X_1$ can be an amino acid amide residue of an amino acid with carboxylic acid in the side chain. $X_1$ can also be a chain composed of two, three or four amino acid amide residues of amino acids with carboxylic acids in their side chain. Thus, $X_1$ can, for example, be selected from the group consisting of β-D-Asp-amide, β-L-Asp-amide, γ-L-Glu-amide and γ-D-Glu-amide.

In one aspect of the invention $X_1$ is a chain composed of three amino acid residues, independently having from 4 to 10 carbon atoms, where at least one of the amino acid residues of the chain being selected from the group of residues having an amide. The combination of the three amino acid amides can be any combination of β-D-Asp-amide, β-L-Asp-amide, γ-L-Glu-amide and γ-D-Glu-amide, which means that 64 different combinations are possible.

In a further aspect, $X_1$ is a chain composed of four amino acid residues, independently having from 4 to 10 carbon atoms, where at least one of the amino acid residues of the chain being selected from the group of residues having an amide. The combination of the four amino acid amides can be any combination of β-D-Asp-amide, β-L-Asp-amide, γ-L-Glu-amide and γ-D-Glu-amide, which means that 256 different combinations are possible.

In one aspect of the invention $X_1$ is an amino acid residue having from 4 to 10 carbon atoms. The amino acid residues may be selected from the group consisting of α-Asp, β-Asp, α-Glu, γ-Glu, α-hGlu and δ-hGlu. In one aspect $X_1$ is γ-Glu.

In one aspect $X_1$ is a chain of amino acid residues.

The starting product for the acylation, the parent insulin or insulin analogue or a precursor thereof can be produced by either well-know peptide synthesis or by well known recombinant production in suitable transformed microorganisms. Thus the insulin starting product can be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, Such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of peptide in question.

The DNA sequence encoding the parent insulin may suitably be of genomic or cDNA origin, for instance obtained by preparing a genomic or cDNA library and screening for DNA sequences coding for all or part of the polypeptide by hybridisation using synthetic oligonucleotide probes in accordance with standard techniques (see, for example, Sambrook, J. Fritsch, E F and Maniatis, T. *Molecular Cloning: A Laboratory Manual*, Cold Spring Harbor Laboratory Press, New York, 1989). The DNA sequence encoding the parent insulin may also be prepared synthetically by established standard methods, e.g. the phosphoramidite method described by Beaucage and Caruthers, *Tetrahedron Letters* 22 (1981), 1859-1869, or the method described by Matthes et al., *EMBO Journal* 3 (1984), 801-805. The DNA sequence may also be prepared by polymerase chain reaction using specific primers, for instance as described in U.S. Pat. No. 4,683,202 or Saiki et al., *Science* 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is for example an expression vector in which the DNA sequence encoding the parent insulin is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the parent insulin in a variety of host cells are well known in the art, cf. for instance Sambrook et al., Supra.

The DNA sequence encoding the parent insulin may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracycline chloramphenicol, neomycin, hygromycin or methotrexate.

To direct a peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the parent insulin, the promoter and optionally the terminator and/or secretory signal sequence, respectively, and to insert them into suitable vectors containing the information necessary for replication, are well known to persons skilled in the art (cf., for instance, Sambrook et al., Supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

The parent insulin molecule is then converted into the insulin derivatives of the invention by introducing of the relevant substituent in either the B1 position or in the chosen Lys position in the A or B chain. The substituent can be introduced by any convenient method and many methods are disclosed in the prior art for acylation of an amino group. More details will appear from the following examples.

In one aspect the invention is related to a pharmaceutical composition comprising a therapeutically effective amount of an insulin derivative or a zinc complex of the insulin derivative according to the invention optionally together with a pharmaceutically acceptable carrier and/or a pharmaceutically acceptable additive, which composition can be provided for the treatment of type 1 diabetes, type 2 diabetes and other states that cause hyperglycaemia in patients in need of such a treatment.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition comprising the insulin derivative or a zinc complex of the insulin derivative according to the invention optionally together with a pharmaceutically acceptable carrier and/or pharmaceutical acceptable additives.

In one aspect of the invention, there is provided a method for the manufacture of a pharmaceutical composition for the use in the treatment of type 1 diabetes, type 2 diabetes and other states that cause hyperglycaemia, the composition comprising an insulin derivative or a zinc complex of the insulin derivative according to the invention optionally together with a pharmaceutically acceptable carrier and/or pharmaceutical acceptable additives.

In one aspect of the invention, there is provided a pharmaceutical composition for treating type 1 diabetes, type 2 diabetes and other states that cause hyperglycaemia in a patient in need of such a treatment, the composition comprising a therapeutically effective amount of an insulin derivative or a zinc complex of the insulin derivative according to the invention in mixture with an insulin or an insulin analogue which has a rapid onset of action, optionally together with pharmaceutically acceptable carriers and/or additives.

In one aspect of the invention, there is provided a method of treating type 1 diabetes, type 2 diabetes and other states that cause hyperglycaemia in a patient in need of such a treatment, comprising administering to the patient a therapeutically effective amount of an pharmaceutical composition comprising the insulin derivative or a zinc complex of the insulin derivative according to the invention in mixture with an insulin or an insulin analogue which has a rapid onset of action, optionally together with a pharmaceutically acceptable carrier and/or pharmaceutical acceptable additives.

In one aspect of the invention, there is provided a method for the manufacture of a pharmaceutical composition for the use in the treatment of type 1 diabetes, type 2 diabetes and other states that cause hyperglycaemia, the composition comprising a therapeutically effective amount of an insulin derivative or a zinc complex of the insulin derivative according to the invention in mixture with an insulin or an insulin analogue which has a rapid onset of action, optionally together with a pharmaceutically acceptable carrier and/or pharmaceutical acceptable additives.

In one aspect the invention provides a pharmaceutical composition being a mixture of an insulin derivative or a zinc complex of the insulin derivative according to the invention and a rapid acting insulin analogue selected group consisting of AspB28 human insulin; LysB28ProB29 human insulin and LysB3GluB29 human insulin.

One aspect of the invention is related to a pharmaceutical composition comprising a therapeutically effective amount of an insulin derivative or a zinc complex of the insulin derivative according to the invention optionally together with a pharmaceutically acceptable carrier and/or a pharmaceutically acceptable additive, which can be provided for pulmonary treatment of type 1 diabetes, type 2 diabetes and other states that cause hyperglycaemia in patients in need of such a treatment.

In one aspect the invention is related to application of a pharmaceutical composition for pulmonary treatment of type 1 diabetes, type 2 diabetes and other states that cause hyperglycaemia in a patient in need of such a treatment, the pharmaceutical composition comprising a therapeutically effective amount of an insulin derivative or a zinc complex of the insulin derivative according to the invention optionally in mixture with an insulin or an insulin analogue which has a rapid onset of action, together with pharmaceutically acceptable carriers and/or additives.

In one aspect of the invention, there is provided a method for the manufacture of a pharmaceutical composition for the use in the treatment of type 1 diabetes, type 2 diabetes and other states that cause hyperglycaemia, the composition being used pulmonary and comprising a therapeutically effective amount of an insulin derivative or a zinc complex of the insulin derivative according to the invention optionally in mixture with an insulin or an insulin analogue which has a rapid onset of action, together with a pharmaceutically acceptable carrier and/or pharmaceutical acceptable additives.

The insulin derivative according to the invention and the rapid acting insulin analogue can be mixed in a ratio from about 90/10%; about 70/30% or about 50/50%.

In one aspect, the invention relates to a pharmaceutical composition comprising an insulin derivative according to the invention which is soluble at physiological pH values.

In one aspect, the invention relates to a pharmaceutical composition comprising an insulin derivative according to the invention which is soluble at pH values in the interval from about 6.5 to about 8.5.

In one aspect, the invention relates to a pharmaceutical composition with a prolonged profile of action which comprises an insulin derivative according to the invention.

In one aspect, the invention relates to a pharmaceutical composition which is a solution containing from about 120 nmol/ml to about 2400 nmol/ml, from about 400 nmol/ml to about 2400 nmol/ml, from about 400 nmol/ml to about 1200 nmol/ml, from about 600 nmol/ml to about 2400 nmol/ml, or from about 600 nmol/ml to about 1200 nmol/ml of an insulin derivative according to the invention or of a mixture of the insulin derivative according to the invention with a rapid acting insulin analogue.

Pharmaceutical Compositions

The insulin derivatives of this invention of the claimed formula can, for example, be administered subcutaneously, orally, or pulmonary.

For subcutaneous administration, the compounds of the formula are formulated analogously with the formulation of known insulins. Furthermore, for subcutaneous administration, the compounds of the formula are administered analogously with the administration of known insulins and, generally, the physicians are familiar with this procedure.

The insulin derivatives of this invention may be administered by inhalation in a dose effective manner to increase circulating insulin levels and/or to lower circulating glucose levels. Such administration can be effective for treating disorders such as diabetes or hyperglycemia. Achieving effective doses of insulin requires administration of an inhaled dose of insulin derivative of this invention of more than about 0.5 µg/kg to about 50 µg/kg. A therapeutically effective amount can be determined by a knowledgeable practitioner, who will take into account factors including insulin level, blood glucose levels, the physical condition of the patient, the patient's pulmonary status, or the like.

Administration by inhalation can result in pharmacokinetics comparable to subcutaneous administration of insulins. Different inhalation devices typically provide similar pharmacokinetics when similar particle sizes and similar levels of lung deposition are compared.

According to the invention, insulin derivative of this invention may be delivered by any of a variety of inhalation devices known in the art for administration of a therapeutic agent by inhalation. These devices include metered dose inhalers, nebulizers, dry powder generators, sprayers, and the like. Insulin derivative of this invention is delivered by a dry powder inhaler or a sprayer. There are a several desirable features of an inhalation device for administering insulin derivative of this invention. For example, delivery by the inhalation device is advantageously reliable, reproducible, and accurate. The inhalation device should deliver small particles, for example, less than about 10 µm, for example about 1-5 µm, for good respirability. Some specific examples of commercially available inhalation devices suitable for the practice of this invention are TURBOHALER™ (Astra), ROTAHALER® (Glaxo), DISKUS® (Glaxo), SPIROS™ inhaler (Dura), devices marketed by Inhale Therapeutics, AER$_x$.™ (Aradigm), the ULTRAVENT® nebulizer (Mallinckrodt), the ACORN II® nebulizer (Marquest Medical Products), the VENTOLIN® metered dose inhaler (Glaxo), the SPINHALER® powder inhaler (Fisons), or the like.

As those skilled in the art will recognize, the formulation of insulin derivative of this invention, the quantity of the formulation delivered, and the duration of administration of a single dose depend on the type of inhalation device employed. For some aerosol delivery systems, Such as nebulizers, the frequency of administration and length of time for which the system is activated will depend mainly on the concentration of insulin conjugate in the aerosol. For example, Shorter periods of administration can be used at higher concentrations of insulin conjugate in the nebulizer solution. Devices such as metered dose inhalers can produce higher aerosol concentrations, and can be operated for shorter periods to deliver the desired amount of insulin conjugate. Devices such as powder inhalers deliver active agent until a given charge of agent is expelled from the device. In this type of inhaler, the amount of insulin derivative of this invention in a given quantity of the powder determines the dose delivered in a single administration.

The particle size of insulin derivative of this invention in the formulation delivered by the inhalation device is critical with respect to the ability of insulin to make it into the lungs, and into the lower airways or alveoli. The insulin derivative of this invention can be formulated so that at least about 10% of the insulin conjugate delivered is deposited in the lung, for example about 10 to about 20%, or more. It is known that the maximum efficiency of pulmonary deposition for mouth breathing humans is obtained with particle sizes of about 2 μm to about 3 μm. When particle sizes are above about 5 μpulmonary deposition decreases substantially. Particle sizes below about 1 μm cause pulmonary deposition to decrease, and it becomes difficult to deliver particles with sufficient mass to be therapeutically effective. Thus, particles of the insulin derivative delivered by inhalation have a particle size less than about 10 μm, for example in the range of about 1 μm to about 5 μm. The formulation of the insulin derivative is selected to yield the desired particle size in the chosen inhalation device.

Advantageously for administration as a dry powder, an insulin derivative of this invention is prepared in a particulate form with a particle size of less than about 10 μm, for example about 1 to about 5 μm. The particle size is effective for delivery to the alveoli of the patient's lung. The dry powder is largely composed of particles produced so that a majority of the particles have a size in the desired range. Advantageously, at least about 50% of the dry powder is made of particles having a diameter less than about 10 μm. Such formulations can be achieved by spray drying, milling, or critical point condensation of a solution containing insulin conjugate and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. In another type of inhaler, air flow generated by the patient's inhalation activates an impeller motor which deagglomerates the particles.

Formulations of insulin derivatives of this invention for administration from a dry powder inhaler typically include a finely divided dry powder containing the derivative, but the powder can also include a bulking agent, carrier, excipient, another additive, or the like. Additives can be included in a dry powder formulation of insulin conjugate, for example, to dilute the powder as required for delivery from the particular powder inhaler, to facilitate processing of the formulation, to provide advantageous powder properties to the formulation, to facilitate dispersion of the powder from the inhalation device, to stabilize the formulation (for example, antioxidants or buffers), to provide taste to the formulation, or the like. Advantageously, the additive does not adversely affect the patient's airways. The insulin derivative can be mixed with an additive at a molecular level or the solid formulation can include particles of the insulin conjugate mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, Starch, or combinations thereof; surfactants, Such as sorbitols, diphosphatidyl choline, or lecithin; or the like. Typically an additive, Such as a bulking agent, is present in an amount effective for a purpose described above, often at about 50% to about 90% by weight of the formulation. Additional agents known in the art for formulation of a protein such as insulin analogue protein can also be included in the formulation.

A spray including the insulin derivatives of this invention can be produced by forcing a suspension or solution of insulin conjugate through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of insulin conjugate delivered by a sprayer have a particle size less than about 10 μm, for example in the range of about 1 μm to about 5 μm.

Formulations of insulin derivatives of this invention suitable for use with a sprayer will typically include the insulin derivative in an aqueous solution at a concentration of about 1 mg to about 20 mg of insulin conjugate per ml of solution. The formulation can include agents such as an excipient, a buffer, an isotonicity agent, a preservative, a surfactant, and, for example zinc. The formulation can also include an excipient or agent for stabilization of the insulin derivative, Such as a buffer, a reducing agent, a bulk protein, or a carbohydrate. Bulk proteins useful in formulating insulin conjugates include albumin, protamine, or the like. Typical carbohydrates useful in formulating insulin conjugates include sucrose, mannitol, lactose, trehalose, glucose, or the like. The insulin derivative formulation can also include a surfactant, which can reduce or prevent surface-induced aggregation of the insulin conjugate caused by atomization of the solution in forming an aerosol. Various conventional surfactants can be employed, Such as polyoxyethylene fatty acid esters and alcohols, and polyoxyethylene sorbitol fatty acid esters. Amounts will generally range between about 0.001 and about 4% by weight of the formulation.

Pharmaceutical compositions containing an insulin derivative according to the present invention may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump. Further options are to administer the insulin nasally or pulmonally, for example in compositions, powders or liquids, specifically designed for the purpose.

Injectable compositions of the insulin derivatives of the invention can be prepared using the conventional techniques of the pharmaceutical industry which involve dissolving and mixing the ingredients as appropriate to give the desired end product. Thus, according to one procedure, an insulin derivative according to the invention is dissolved in an amount of water which is somewhat less than the final volume of the composition to be prepared. An isotonic agent, a preservative and a buffer is added as required and the pH value of the solution is adjusted—if necessary—using an acid, e.g. hydrochloric acid, or a base, e.g. aqueous sodium hydroxide as needed. Finally, the volume of the solution is adjusted with water to give the desired concentration of the ingredients.

In a further aspect of the invention the buffer is selected from the group consisting of sodium acetate, Sodium carbonate, citrate, glycylglycine, histidine, glycine, lysine, arginine, sodium dihydrogen phosphate, disodium hydrogen phosphate, Sodium phosphate, and tris(hydroxymethyl)-aminomethane, bicine, tricine, malic acid, Succinate, maleic acid, fumaric acid, tartaric acid, aspartic acid or mixtures thereof. Each one of these specific buffers constitutes an alternative aspect of the invention.

In a further aspect of the invention the formulation further comprises a pharmaceutically acceptable preservative which may be selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further aspect of the invention the preservative is present in a concentration from 0.1 mg/ml to 20 mg/ml. In a further aspect of the invention the preservative is present in a concentration from 0.1 mg/ml to 5 mg/ml. In a further aspect of the invention the preservative is present in a concentration from 5 mg/ml to 10 mg/ml. In a further aspect of the invention the preservative is present in a concentration from 10 mg/ml to 20 mg/ml. Each one of these specific preservatives constitutes an alternative aspect of the invention. The use of a preservative in pharmaceutical compositions is well-known to the skilled person. For convenience reference is made to Remington: *The Science and Practice of Pharmacy,* $19^{th}$ edition, 1995.

In a further aspect of the invention the formulation further comprises an isotonic agent which may be selected from the group consisting of a salt (e.g. sodium chloride), a sugar or sugar alcohol, an amino acid (e.g. glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, Sorbose, xylose, maltose, lactose, Sucrose, trehalose, dextran, pullulan, dextrin, cyclodextrin, Soluble starch, hydroxyethyl starch and carboxymethylcellulose-Na may be used. In one aspect the sugar additive is sucrose. Sugar alcohol is defined as a C4-C8 hydrocarbon having at least one—OH group and includes, for example, mannitol, Sorbitol, inositol, galactitol, dulcitol, xylitol, and arabitol. In one aspect the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one aspect, the sugar or sugar alcohol concentration is between about 1 mg/ml and about 150 mg/ml. In a further aspect of the invention the isotonic agent is present in a concentration from 1 mg/ml to 50 mg/ml. In a further aspect of the invention the isotonic agent is present in a concentration from 1 mg/ml to 7 mg/ml. In a further aspect of the invention the isotonic agent is present in a concentration from 8 mg/ml to 24 mg/ml. In a further aspect of the invention the isotonic agent is present in a concentration from 25 mg/ml to 50 mg/ml. Each one of these specific isotonic agents constitutes an alternative aspect of the invention. The use of an isotonic agent in pharmaceutical compositions is well-known to the skilled person. For convenience reference is made to Remington: *The Science and Practice of Pharmacy,* $19^{th}$ edition, 1995.

Typical isotonic agents are sodium chloride, mannitol, dimethyl sulfone and glycerol and typical preservatives are phenol, m-cresol, methyl p-hydroxybenzoate and benzyl alcohol.

Examples of suitable buffers are sodium acetate, glycylglycine, HEPES (4-(2-hydroxyethyl)-1-piperazineethanesulfonic acid) and sodium phosphate.

A composition for nasal administration of an insulin derivative according to the present invention may, for example, be prepared as described in European Patent No. 272097 (to Novo Nordisk A/S).

Compositions containing insulin derivatives of this invention can be used in the treatment of states which are sensitive to insulin. Thus, they can be used in the treatment of type 1 diabetes, type 2 diabetes and hyperglycaemia for example as sometimes seen in seriously injured persons and persons who have undergone major surgery. The optimal dose level for any patient will depend on a variety of factors including the efficacy of the specific insulin derivative employed, the age, body weight, physical activity, and diet of the patient, on a possible combination with other drugs, and on the severity of the state to be treated. It is recommended that the daily dosage of the insulin derivative of this invention be determined for each individual patient by those skilled in the art in a similar way as for known insulin compositions.

Where expedient, the insulin derivatives of this invention may be used in mixture with other types of insulin, e.g. insulin analogues with a more rapid onset of action. Examples of such insulin analogues are described e.g. in the European patent applications having the publication Nos. EP 214826 (Novo Nordisk A/S), EP 375437 (Novo Nordisk A/S) and EP 383472 (Eli Lilly & Co.).

The invention will further be summarized in the following paragraphs:

1a. Insulin derivative comprising a parent insulin and a substituent, wherein the substituent comprises a terminal group which is negatively charged at physiological pH; an aromatic group having 0, 1, 2 or 3 carbon between the aromatic group and the terminal group; an aliphatic chain having at least 4 $CH_2$ groups; and a linker, wherein the aliphatic chain is bound to the parent insulin through the linker, with the proviso that 1) if the aromatic group is arylene or heteroarylene, then it is not linked via oxygen and 2) if the aromatic group is $C_6H_4$ then it is not linked via sulphur.

2a. Insulin derivative according to paragraph 1a, wherein the aromatic group is arylene, heteroarylene or a polycyclic system.

3a. Insulin derivative according to paragraph 1a or 2a, wherein the substituent comprises more than one aromatic group.

4a. Insulin derivative according to paragraph 2a, wherein the terminal group is —COOH.

5a. Insulin derivative according to paragraph 2a, wherein the arylene may be substituted with one or two groups selected from —COOH, —$CH_3$, —$SO_3H$, —$(CH_2)_{1-6}$—$SO_3H$, —$PO_3H_2$, —$(CH_2)_{1-6}$—O—$PO_3H_2$, tetrazo-5-lyl or $CONH_2$, $C_{1-6}$-alkyl, $C_{2-6}$-alkenyl, $C_{2-6}$-alkynyl, hydrogen, halogen, —CN, —$CF_3$, —$OCF_3$, —$S(O)_2CF_3$, —$SCF_3$, —$NO_2$, —$OR^2$, —$NR^2R^3$, —$SR^2$, —$NR^2S(O)_2R^3$, —$S(O)_2NR^2R^3$, —$S(O)NR^2R^3$, —$S(O)R^2$, —$S(O)_2R^2$, —$C(O)NR^2R^3$, —$OC(O)NR^2R^3$, —$NR^2C(O)R^3$, —$CH_2C(O)NR^2R^3$, —$OCH_2C(O)NR^2R^3$, —$OC(O)R^2$, —$OCH_2C(O)R^2$—$C(O)R^2$ or —$C(O)OR^2$ or —$OCH_2C(O)OR^2$, where $R^2$ and $R^3$ independently are hydrogen, $C_{1-6}$-alkyl, $C_{2-6}$-alkenyl or $C_{2-6}$-alkynyl.

6a. Insulin derivative according to paragraph 5a, wherein the arylene may be substituted with one or two groups selected from $C_{1-3}$-alkyl, $C_{2-3}$-alkenyl, $C_{2-3}$-alkynyl or —$OR^2$ where $R^2$ can be $C_{1-3}$-alkyl, $C_{2-3}$-alkenyl or $C_{2-3}$-alkynyl.

7a. Insulin derivative according to paragraph 2a, wherein the heteroarylene group comprises nitrogen, Sulphur or oxygen 8a. Insulin derivative according to paragraph 7a, wherein the carbon or the nitrogen may be substituted.

9a. Insulin derivative according to paragraph 8a wherein the carbon may be substituted with one or two groups selected from the group consisting of —COOH, —$CH_3$, —$SO_3H$, —$(CH_2)_{1-6}$—$SO_3H$, —$PO_3H_2$, —$(CH_2)_{1-6}$—O—$PO_3H_2$, tetrazo-5-lyl or $CONH_2$, $C_{1-6}$-alkyl, $C_{2-6}$-alkenyl, $C_{2-6}$-alkynyl, hydrogen, halogen, —CN, —$CF_3$, —$OCF_3$, $S(O)_2CF_3$, —$SCF_3$, —$NO_2$, —$OR^2$, —$NR^2R^3$, —$SR^2$, —$NR^2S(O)_2R^3$, —$S(O)_2NR^2R^3$, —$S(O)NR^2R^3$, —$S(O)R^2$—$S(O)_2R^2$, —$C(O)NR^2R^3$, —$OC(O)NR^2R^3$, —$NR^2C(O)R^3$, —$CH_2C(O)NR^2R^3$, —$OCH_2C(O)NR^2R^3$, —$OC(O)R^2$, —$OCH_2C(O)R^2$—$C(O)R^2$ or —$C(O)OR^2$ or —$OCH_2C(O)OR^2$, where $R^2$ and $R^3$ independently are hydrogen, $C_{1-6}$-alkyl, $C_{2-6}$-alkenyl or $C_{2-6}$-alkynyl.

10a. Insulin derivative according to paragraph 8a wherein the nitrogen may be substituted with one or two groups selected from the group consisting of hydrogen, $C_{1-6}$-alkyl, $C_{2-6}$-alkenyl, $C_{2-6}$-alkynyl, C(O)—$C_{1-6}$-alkyl, C(O)—$C_{2-6}$-alkenyl or C(O)—$C_{2-6}$-alkynyl.

11a. Insulin derivative according to paragraph 2a, wherein the polycyclic system may be substituted with one or two groups selected from —COOH, —$CH_3$, —$SO_3H$, —$(CH_2)_{1-6}$—$SO_3H$, —$PO_3H_2$, —$(CH_2)_{1-6}$—O—$PO_3H_2$, tetrazo-5-lyl or $CONH_2$, $C_{1-6}$-alkyl, $C_{2-6}$-alkenyl, $C_{2-6}$-alkynyl, hydrogen, halogen, —CN, —$CF_3$, —$OCF_3$, —$S(O)_2CF_3$, —$SCF_3$, —$NO_2$, —$OR^2$, —$NR^2R^3$, —$SR^2$, —$NR^2S(O)_2 R^3$, —$S(O)_2 NR^2R^3$, —$S(O)NR^2R^3$, —$S(O)R^2$, —$S(O)_2 R^2$, —$C(O)NR^2R^3$, —$OC(O)NR^2R^3$, —$NR^2C(O)R^3$, —$CH_2C(O)NR^2R^3$, —$OCH_2C(O)NR^2R^3$, —$OC(O)R^2$, —$OCH_2C(O)R^2$, —$C(O)R^2$ or —$C(O)OR^2$ or —$OCH_2C(O)OR^2$, where $R^2$ and $R^3$ independently are hydrogen, $C_{1-6}$-alkyl, $C_{2-6}$-alkenyl or $C_{2-6}$-alkynyl.

12a. Insulin derivative according to paragraphs 1a-11a, wherein the linker comprises 1-4 amino acid residues linked together via amide bonds.

13a. Insulin derivative according to paragraph 12a, wherein the linker has at least one free carboxylic acid group or a group which is negatively charged at neutral pH.

14a. Insulin derivative according to paragraphs 1a-11a, wherein the linker comprises 1-4 amino acid amide residues linked together via amide bonds.

15a. Insulin derivative according to paragraph 1a-11a, wherein the linker comprises an amide.

16a. Insulin derivative according to any of paragraphs 1a-11a, wherein the linker comprises an amide or a N-substituted amide of the formula —$CONR^4R^5$, —$SONR^4R^5$ or —$SO_2NR^4R^5$ where $R^4$ and $R^5$ independently of each other can be hydrogen, —$CH_3$—$CH_{1-6}CH_3$, —$(CH_2)_{1-6}$—O—$PO_3H_2$, $CONH_2$, $C_{1-6}$-alkyl, $C_{2-6}$-alkenyl or $C_{2-6}$-alkynyl and when $R^4$ and $R^5$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds.

17a. Insulin derivative according to paragraph 16a, where $R^4$ and $R^5$ are hydrogen.

18a. An insulin derivative according to any of the preceeding paragraphs, wherein the substituent is attached to the ε-amino group of LysB29.

19a. Insulin derivative according to paragraph 1a having the formula

wherein Ins is the parent insulin moiety which via the α-amino group of the N-terminal amino acid residue of the B chain or an ε-amino group of a Lys residue present in the B-chain of the insulin moiety is bound to the CO— group in the substituent via an amide bond;

$X_1$ is

—CO—$(CH_2)_n$ where n is 1, 2, 3, 4, 5 or 6;

—CO—$((CR^6R^7)_q$—NR—CO$)_{1-4}$—, where $R^6$ and $R^7$ independently of each other and independently for each value of q can be hydrogen, —COOH, or OH, q is 1-6 and R is hydrogen, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H$_2$; $C_{1-6}$-alkyl, $C_{2-6}$-alkenyl; $C_{2-6}$-alkynyl or arylene, which arylene may be substituted with 1 or 2 groups selected from group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$—NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where $R^2$ and $R^3$ independently are hydrogen, $C_{1-6}$-alkyl, $C_{2-6}$-alkenyl or $C_{2-6}$-alkynyl.

an α-amino acid residue or an α-amino acid amide residue having a carboxylic acid group in the substituent which residue forms, with one of its carboxylic acid groups, an amide group together with the α-amino group of the N-terminal amino acid residue of the B chain or together with the ε-amino group of a Lys residue present in the B chain of the parent insulin;

a chain composed of two, three or four α-amino acid residues or α-amino acid amide residues linked together via amide bonds, which chain—via an amide bond—is linked to the α-amino group of the N-terminal amino acid residue of the B chain or to the ε-amino group of a Lys residue present in the B chain of the parent insulin or a bond $X_2$ is:
—CO—
—COCH(R$^8$)—;
—COCH$_2$N(CH$_2$R$^8$)—;
—COCH$_2$N(CH$_2$R$^8$)COCH$_2$N(CH$_2$R$^8$)—;
—COCH$_2$CH$_2$N(CH$_2$CH$_2$R$^8$)—;
—COCH$_2$CH$_2$N(CH$_2$CH$_2$R$^8$)—COCH$_2$CH$_2$N(CH$_2$CH$_2$R$^8$)—;
—COCH$_2$N(CH$_2$CH$_2$R$^8$)—;
—COCH$_2$CH$_2$N(CH$_2$R$^8$)—; where $R^8$ can be COOH or CONH$_2$
—(CO—$(CH_2)_{2-6}$—NH—CO$)_{1-4}$—;
—(CO—$(CH_2)_{2-6}$—CO—NH$)_{1-4}$—;
—(CO—$(CR^9R^{10})_{1-6}$—CO—NH$)_{1-4}$—, where $R^9$ and $R^{10}$, independently of each other can be H, —COOH, —$(CH_2)_{1-6}$COOH, CH$_3$, —$(CH_2)_{1-6}$CH$_3$ or CONH$_2$; or a bond W is:

arylene, which may be substituted with one or two groups selected from the group consisting —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where $R^2$ and $R^3$ independently are hydrogen, $C_{1-6}$-alkyl, $C_{2-6}$-alkenyl or $C_{2-6}$-alkynyl; and when $R^2$ and $R^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;

heteroarylene, wherein the carbon may be substituted with one or two groups selected from the group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$—NR$^2$R$^3$, —SR$^2$, —NR$^2$S(O)$_2$R$^3$, —S(O)$_2$NR$^2$R$^3$, —S(O)NR$^2$R$^3$, —S(O)R$^2$—S(O)$_2$R$^2$—C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where $R^2$ and $R^3$ independently are hydrogen, $C_{1-6}$-alkyl $C_{2-6}$-alkenyl or $C_{2-6}$-alkynyl; and when $R^2$ and $R^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;

heteroarylene, wherein the nitrogen may be substituted with a group selected from the group consisting of hydrogen, $C_{1-6}$-alkyl $C_{2-6}$-alkenyl or $C_{2-6}$-alkynyl; or a bond m is 0, 1, 2, 3, 4, 5 or 6;

X is
—O—;
—C=O;
—S—
—S(O)—
—S(O)$_2$

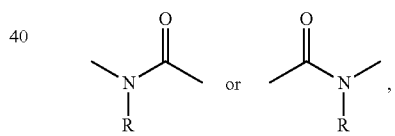

where R hydrogen, $C_{1-6}$-alkyl $C_{2-6}$-alkenyl or $C_{2-6}$-alkynyl; or a bond;

Y is

—$(CR^6R^7)_q$—NR$^1$—CO$)_{1-4}$—, where $R^6$ and $R^7$ independently of each other can be H, —COOH, or OH, q is 1-6 and $R^1$ is hydrogen, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H$_2$; $C_{1-6}$-alkyl $C_{2-6}$-alkenyl; $C_{2-6}$-alkynyl or arylene, which arylene may be substituted with 1 or 2 groups selected from group consisting of —COOH, —CH$_3$, —SO$_3$H, —$(CH_2)_{1-6}$—SO$_3$H, —PO$_3$H$_2$, —$(CH_2)_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—

$C(O)R^2$ or —$C(O)OR^2$ or —$OCH_2C(O)OR^2$, where $R^2$ and $R^3$ independently are hydrogen, $C_{1-6}$-alkyl, $C_{2-6}$-alkenyl or $C_{2-6}$-alkynyl;
—$NR^1R^2$, where $R^1$ and $R^2$ are defined as above; or
a bond;

Q is
a divalent hydrocarbon chain of the formula —$(CH_2)_{s1}$-$Q_1$-$(CH_2)_{s2}$-$Q_2$-$(CH_2)_{s3}$-$Q_3$-$(CH_2)_{s4}$-$Q_4$-$(CH_2)_{s5}$—; wherein $Q_1$-$Q_3$ independently of each other can be O, S, S(O), S(O)$_2$, P(O$_2$H), —O—P(O$_2$H)—O—, NH, NR$^2$; —N(COR$^2$)— or a bond; where $R^2$ is hydrogen, $C_{1-6}$-alkyl, $C_{2-6}$-alkenyl, $C_{2-6}$-alkynyl, where $Q_4$ can be
   arylene, which may be substituted with one or two groups selected from the group consisting —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where $R^2$ and $R^3$ independently are hydrogen, $C_{1-6}$-alkyl, $C_{2-6}$-alkenyl or $C_{2-6}$-alkynyl; and when $R^2$ and $R^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;
   heteroarylene, wherein the carbon may be substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where $R^2$ and $R^3$ independently are hydrogen, $C_{1-6}$-alkyl, $C_{2-6}$-alkenyl or $C_{2-6}$-alkynyl; and when $R^2$ and $R^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;
   heteroarylene, wherein the nitrogen may be substituted with one or two groups selected from the group consisting of hydrogen, $C_{1-6}$-alkyl, $C_{2-6}$-alkenyl or $C_{2-6}$-alkynyl; or
   a polycyclic system
and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that $Q_1$, $Q_2$ and $Q_3$ may not form bonds to each other and if s1, s2 and s3 are zero or 1, then no —CH$_2$— may be bound to 2 of the following atoms: O, N, S, or P and Z is:
—COOH;
—CO-Asp;
—CO-Glu;
—CO-Gly;
—CO-Sar;
—CH(COOH)$_2$;
—N(CH$_2$COOH)$_2$;
—SO$_3$H
—PO$_3$H$_2$;
O—SO$_3$H;
O—PO$_3$H$_2$;
tetrazo-5-lyl; or
a bicyclic system consisting of a 6 membered and a 5 membered ring which has a negative charge at physiological pH values and any Zn$^{2+}$ complex thereof.

20a. Insulin derivative according to paragraph 19a, wherein $X_1$ is an amino acid amide residue having from 4 to 10 carbon atoms.

21a. Insulin derivative according to any of paragraphs 19a-20a, wherein $X_1$ is selected from the group consisting of β-D-Asp-amide, β-L-Asp-amide, γ-L-Glu-amide and γ-D-Glu-amide.

22a. Insulin derivative according to paragraph 19a, wherein $X_1$ is a chain of amino acid amide residues.

23a. Insulin derivative according to paragraphs 19a or 22a, wherein $X_1$ is a chain of two amino acid amide residues selected from the group consisting of β-L-Asp-amide-β-L-Asp-amide, β-L-Asp-amide-γ-L-Glu-amide, γ-L-Glu-amide-γ-L-Glu-amide, γ-L-Glu-amide-β-L-Asp-amide, β-L-Asp-amide-β-D-Asp-amide, β-L-Asp-amide-γ-D-Glu-amide, γ-L-Glu-amide-γ-D-Glu-amide, γ-L-Glu-amide-β-D-Asp-amide, β-D-Asp-amide-β-L-Asp-amide, β-D-Asp-amide-γ-L-Glu-amide, γ-D-Glu-amide-γ-L-Glu-amide, γ-D-Glu-amide-β-L-Asp-amide, β-D-Asp-amide-β-D-Asp-amide, β-D-Asp-amide-γ-D-Glu-amide, γ-D-Glu-amide-γ-D-Glu-amide, γ-D-Glu-amide-β-D-Asp-amide.

24a. Insulin derivative according to paragraph 19a, wherein $X_1$ is an amino acid residue having from 4 to 10 carbon atoms.

25a. Insulin derivative according to paragraph 24a, wherein $X_1$ is selected from the group consisting of α-Asp, G-Asp, α-Glu, γ-Glu, α-hGlu and δ-hGlu.

26a. Insulin derivative according to paragraph 25a, wherein $X_1$ is γ-Glu. 27a. Insulin derivative according to paragraph 19a, wherein $X_1$ is a chain of amino acid residues 28a. Insulin derivative according to paragraph 27a, wherein $X_1$ is a chain composed of two α-amino acid residues of which one has from 4 to 10 carbon atoms and a free carboxylic acid group while the other has from 2 to 11 carbon atoms but no free carboxylic acid group.

29a. Insulin derivative according to paragraph 28a, wherein $X_1$ is selected from the group consisting of α-Asp-Gly; Gly-α-Asp; β-Asp-Gly; Gly-β-Asp; α-Glu-Gly; Gly-α-Glu; γ-Glu-Gly; Gly-γ-Glu; α-hGlu-Gly; Gly-α-hGlu; δ-hGlu-Gly; and Gly-δ-hGlu.

30a. Insulin derivative according to paragraph 27a, wherein $X_1$ is a chain composed of two α-amino acid residues independently having from 4 to 10 carbon atoms and both having a free carboxylic acid group.

31a. Insulin derivative according to paragraph 30a, wherein $X_1$ is selected from the group consisting of α-Asp-α-Asp; α-Asp-α-Glu; α-Asp-α-hGlu; α-Asp-β-Asp; α-Asp-γ-Glu; α-Asp-δ-hGlu; β-Asp-α-Asp; β-Asp-α-Glu; β-Asp-α-hGlu; β-Asp-β-Asp; β-Asp-γ-Glu; β-Asp-δ-hGlu; α-Glu-α-Asp; α-Glu-α-Glu; α-Glu-α-hGlu; α-Glu-β-Asp; α-Glu-γ-Glu; α-Glu-δ-hGlu; γ-Glu-α-Asp; γ-Glu-α-Glu; γ-Glu-α-hGlu; γ-Glu-β-Asp; γ-Glu-γ-Glu; γ-Glu-δ-hGlu; α-hGlu-α-Asp; α-hGlu-α-Glu; α-hGlu-α-hGlu; α-hGlu-β-Asp;

α-hGlu-γ-Glu; α-hGlu-δ-hGlu; δ-hGlu-α-Asp; δ-hGlu-α-Glu; δ-hGlu-α-hGlu; δ-hGlu-β-Asp; δ-hGlu-γ-Glu; and δ-hGlu-δ-hGlu.

32a. Insulin derivative according to paragraph 19a, wherein $X_1$ is —CO—$((CR^6R^7)_q$—NR—CO$)_{1-4}$—, where $R^6$ and $R^7$ independently of each other and independently for each value of q can be H, —COOH, or OH, q is 1-6 and R is hydrogen, —$(CH_2)_{1-6}$—COOH; —$(CH_2)_{1-6}$—$CONH_2$; —$(CH_2)_{1-6}$—$SO_3H$; —$(CH_2)_{1-6}$—$PO_3H_2$; —$(CH_2)_{1-6}$—O—$SO_3H_2$; —$(CH_2)_{1-6}$—O—$PO_3H_2$; $C_{1-6}$-alkyl, $C_{2-6}$-alkenyl; $C_{2-6}$-alkynyl or arylene, which arylene may be substituted with 1 or 2 groups selected from group consisting of —COOH, —$CH_3$, —$SO_3H$, —$(CH_2)_{1-6}$—$SO_3H$, —$PO_3H_2$, —$(CH_2)_{1-6}$—O—$PO_3H_2$, tetrazo-5-lyl or $CONH_2$, $C_{1-6}$-alkyl, $C_{2-6}$-alkenyl, $C_{2-6}$-alkynyl, hydrogen, halogen, —CN, —$CF_3$, —$OCF_3$, —$S(O)_2CF_3$, —$SCF_3$, —$NO_2$, —$OR^2$, —$NR^2R^3$, —$SR^2$, —$NR^2S(O)_2R^3$, —$S(O)_2NR^2R^3$, —$S(O)NR^2R^3$, —$S(O)R^2$, —$S(O)_2R^2$, —$C(O)NR^2R^3$, —$OC(O)NR^2R^3$, —$NR^2C(O)R^3$, —$CH_2C(O)NR^2R^3$, —$OCH_2C(O)NR^2R^3$, —$OC(O)R^2$, —$OCH_2C(O)R^2$, —$C(O)R^2$ or —$C(O)OR^2$ or —$OCH_2C(O)OR^2$, where $R^2$ and $R^3$ independently are hydrogen, $C_{1-6}$-alkyl, $C_{2-6}$-alkenyl or $C_{2-6}$-alkynyl.

33a. Insulin derivative according to paragraph 32a, wherein $R^6$ and $R^7$ is H for q=1 and q=2; $R^6$ is H and $R^7$ is —COOH for q=3; q is 3 and R is hydrogen.

34a. Insulin derivative according to any of paragraphs 19a-34a, wherein $X_2$ is a bond 35a. Insulin derivative according to paragraph 19a, wherein $X_2$ is:
—CO—
—$COCH(R^8)$—;
—$COCH_2N(CH_2R^8)$—;
—$COCH_2N(CH_2R^8)COCH_2N(CH_2R^8)$—;
—$COCH_2CH_2N(CH_2CH_2R^8)$—;
—$COCH_2CH_2N(CH_2CH_2R^8)$—$COCH_2CH_2N(CH_2CH_2R^8)$—;
—$COCH_2N(CH_2CH_2R^8)$—;
—$COCH_2CH_2N(CH_2R^8)$—; where $R^8$ can be COOH or $CONH_2$
—(CO—$(CH_2)_{2-6}$—NH—CO$)_{1-4}$—;
—(CO—$(CH_2)_{2-6}$—CO—NH$)_{1-4}$—;
—(CO—$(CR^9R^{10})_{1-6}$—CO—NH$)_{1-4}$—, where $R^9$ and $R^{10}$, independently of each other can be H, —COOH, —$(CH_2)_{1-6}$COOH, $CH_3$, —$(CH_2)_{1-6}CH_3$ or $CONH_2$; or a bond 36a. Insulin derivative according to paragraph 35a, wherein $X_2$ is selected from the group consisting of —(CO—$(CH_2)_2$—NH—CO) 1- or —(CO—$(CH_2)_3$—NH—CO$)_1$—

37a. Insulin derivative according to paragraphs 35a, wherein $X_2$ is —CO— or —COCH(COOH)—.

38a. Insulin derivative according to paragraphs 35a-37a, wherein $X_1$ is a bond.

39a. Insulin derivative according to paragraphs 19a-38a, wherein W is phenylene.

40a. Insulin derivative according to paragraph 39a, wherein W is 5-7 membered heterocyclic ring system comprising nitrogen, oxygen or sulphur.

41a. Insulin derivative according to paragraph 40a, wherein W is a 5 membered heterocyclic ring system comprising at least one oxygen or sulphur.

42a. Insulin derivative according to paragraphs 19a-38a, wherein W is a bond

43a. Insulin derivative according to paragraphs 19a-42a, wherein m is 0, 1 or 2.

44a. Insulin derivative according to paragraphs 19a-43a, wherein X is —CO— or a bond and Y is a bond 45a. Insulin derivative according to any of paragraphs 19a-44a, wherein Q is a divalent hydrocarbon chain of the formula —$(CH_2)_{s1}$-$Q_1$-$(CH_2)_{s2}$-$Q_2$-$(CH_2)_{s3}$-$Q_3$-$(CH_2)_{s4}$-$Q_4$-$(CH_2)_{s5}$—; wherein $Q_1$-$Q_3$ independently of each other can be O, S, S(O), $S(O)_2$, $P(O_2H)$, —O—$P(O_2H)$—O—, NH, $NR^2$; —$N(COR^2)$— or a bond; where $R^2$ is hydrogen, $C_{1-6}$-alkyl, $C_{2-6}$-alkenyl, $C_{2-6}$-alkynyl, where $Q_4$ can be arylene, which may be substituted with one or two groups selected from the group consisting —COOH, —$CH_3$, —$SO_3H$, —$(CH_2)_{1-6}$—$SO_3H$, —$PO_3H_2$, —$(CH_2)_{1-6}$—O—$PO_3H_2$, tetrazo-5-lyl or $CONH_2$, $C_{1-6}$-alkyl, $C_{2-6}$-alkenyl, $C_{2-6}$-alkynyl, hydrogen, halogen, —CN, —$CF_3$, —$OCF_3$, —$S(O)_2CF_3$, —$SCF_3$, —$NO_2$, —$OR^2$, —$NR^2R^3$, —$SR^2$, —$NR^2S(O)_2R^3$, —$S(O)_2NR^2R^3$, —$S(O)NR^2R^3$, —$S(O)R^2$, —$S(O)_2R^2$, —$C(O)NR^2R^3$, —$OC(O)NR^2R^3$, —$NR^2C(O)R^3$, —$CH_2C(O)NR^2R^3$, —$OCH_2C(O)NR^2R^3$, —$OC(O)R^2$, —$OCH_2C(O)R^2$, —$C(O)R^2$ or —$C(O)OR^2$ or —$OCH_2C(O)OR^2$, where $R^2$ and $R^3$ independently are hydrogen, $C_{1-6}$-alkyl, $C_{2-6}$-alkenyl or $C_{2-6}$-alkynyl; and when $R^2$ and $R^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;

heteroarylene, wherein the carbon may be substituted with one or two groups selected from the group consisting of —COOH, —$CH_3$, —$SO_3H$, —$(CH_2)_{1-6}$—$SO_3H$, —$PO_3H_2$, —$(CH_2)_{1-6}$—O—$PO_3H_2$, tetrazo-5-lyl or $CONH_2$, $C_{1-6}$-alkyl, $C_{2-6}$-alkenyl, $C_{2-6}$-alkynyl, hydrogen, halogen, —CN, —$CF_3$, —$OCF_3$, —$S(O)_2CF_3$, —$SCF_3$, —$NO_2$, —$OR^2$, —$NR^2R^3$, —$SR^2$, —$NR^2S(O)_2R^3$, —$S(O)_2NR^2R^3$, —$S(O)NR^2R^3$, —$S(O)R^2$—$S(O)_2R^2$, —$C(O)NR^2R^3$, —$OC(O)NR^2R^3$, —$NR^2C(O)R^3$, —$CH_2C(O)NR^2R^3$, —$OCH_2C(O)NR^2R^3$, —$OC(O)R^2$, —$OCH_2C(O)R^2$—$C(O)R^2$ or —$C(O)OR^2$ or —$OCH_2C(O)OR^2$, where $R^2$ and $R^3$ independently are hydrogen, $C_{1-6}$-alkyl, $C_{2-6}$-alkenyl or $C_{2-6}$-alkynyl; and when $R^2$ and $R^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds;

heteroarylene, wherein the nitrogen may be substituted with one or two groups selected from the group consisting of hydrogen, $C_{1-6}$-alkyl, $C_{2-6}$-alkenyl or $C_{2-6}$-alkynyl; or a polycyclic system and s1, S2, S3 and s4 independently of each other can be zero or an integer from 1 to 10 so that the sum of s1, S2, S3 and s4 is in the range from 4 to 22; and s5 is zero or an integer from 1 to 3, with the proviso that $Q_1$, $Q_2$ and $Q_3$ may not form bonds to each other and if s1, s2 and s3 are zero or 1, then no —$CH_2$— may be bound to 2 of the following atoms: O, N, S, or P and 46a. Insulin derivative according to paragraph 45a, wherein $Q_4$ is arylene.

47a. Insulin derivative according to paragraphs 45a or 46a, wherein $Q_4$ is $C_6H_4$.

48a. Insulin derivative according to paragraphs 45a or 46a, wherein $Q_4$ is arylene, which may be substituted with one or two groups selected from the group consisting —COOH, —$CH_3$, —$SO_3H$, —$(CH_2)_{1-6}$—$SO_3H$, —$PO_3H_2$, —$(CH_2)_{1-6}$—O—$PO_3H_2$, tetrazo-5-lyl or $CONH_2$, $C_{1-6}$- alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$, —NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$—C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, $C_{1-6}$-alkyl, $C_{2-6}$-alkenyl or $C_{2-6}$-alkynyl; and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds.

49a. Insulin derivative according to paragraph 45a, wherein Q$_4$ is heteroarylene 50a. Insulin derivative according to paragraph 49a, wherein the heteroarylene group comprises nitrogen, Sulphur or oxygen 51a. Insulin derivative according to paragraph 50a, wherein the heteroarylene comprises nitrogen, wherein the nitrogen may be substituted with one or two groups selected from the group consisting of hydrogen, $C_{1-6}$-alkyl, $C_{2-6}$-alkenyl or $C_{2-6}$-alkynyl.

52a. Insulin derivative according to paragraph 50a, wherein the heteroarylene comprises carbon, wherein the carbon may be substituted with one or two groups selected from the group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$, —OR$^2$—NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, $C_{1-6}$-alkyl, $C_{2-6}$-alkenyl or $C_{2-6}$-alkynyl and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds.

53a. Insulin derivative according to paragraphs 45a-46a, wherein Q$_4$ is a 5-7 membered ring system 54a. Insulin derivative according to paragraphs 53a, wherein Q$_4$ is a 5 membered ring system 55a. Insulin derivative according to paragraph 45a, wherein Q$_4$ is a polycyclic system 56a. Insulin derivative according to paragraph 55a, wherein the polycyclic system may be substituted with one or two groups selected from —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazo-5-lyl or CONH$_2$, $C_{1-6}$-alkyl, $C_{2-6}$-alkenyl, $C_{2-6}$-alkynyl, hydrogen, halogen, —CN, —CF$_3$, —OCF$_3$, —S(O)$_2$CF$_3$, —SCF$_3$, —NO$_2$—OR$^2$—NR$^2$R$^3$, —SR$^2$, —NR$^2$S(O)$_2$R$^3$, —S(O)$_2$NR$^2$R$^3$, —S(O)NR$^2$R$^3$, —S(O)R$^2$, —S(O)$_2$R$^2$—C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$—C(O)R$^2$ or —C(O)OR$^2$ or —OCH$_2$C(O)OR$^2$, where R$^2$ and R$^3$ independently are hydrogen, $C_{1-6}$-alkyl $C_{2-6}$-alkenyl or $C_{2-6}$-alkynyl and when R$^2$ and R$^3$ are attached to the same nitrogen atom they may, together with the said nitrogen atom, form a 3 to 8 membered heterocyclic ring optionally containing one or two further heteroatoms selected from nitrogen, oxygen and sulfur, and optionally containing one or two double bonds.

57a. Insulin derivative according to paragraphs 55a-56a, wherein Q$_4$ is a bicyclic system.

58a. Insulin derivative according to paragraph 57a, wherein the bicyclic system contains two 5-7 membered ring system.

59a. Insulin derivative according to paragraphs 57a-58a, wherein the bicyclic system contains one 6 membered ring and one 5 membered ring.

60a. Insulin derivative according to paragraph 59a, wherein the 5 membered ring comprises nitrogen, oxygen or sulphur.

61a. Insulin derivative according to paragraphs 45a-60a, wherein Q$_1$, Q$_2$ and Q$_3$ are all bonds.

62a. Insulin derivative according to paragraphs 45a-61a, wherein s2, S3 and s4 are one.

63a. Insulin derivative according to paragraphs 45a-62a, wherein s1 is 5, 6, 7 or 8 and s5 is 0, 1 or 2.

64a. Insulin derivative according to paragraphs 45a-63a, wherein s5 is 0.

65a. Insulin derivative according to paragraphs 45a-63a, wherein s5 is 2.

66a. Insulin derivative according paragraphs 45a-60a and paragraphs 62a-65a, wherein Q$_1$ and Q$_2$ are oxygen.

67a. Insulin derivative according paragraphs 19a-66a, wherein Z is —COOH.

68a. Insulin derivative according paragraphs 19a-66a, wherein Z is —CO-Asp;

69a. Insulin derivative according paragraphs 19a-66a, wherein Z is —CO-Glu.

70a. Insulin derivative according paragraphs 19a-66a, wherein Z is —CO-Gly;

71a. Insulin derivative according paragraphs 19a-66a, wherein Z is —CO-Sar.

72a. Insulin derivative according paragraphs 19a-66a, wherein Z is —CH(COOH)$_2$.

73a. Insulin derivative according paragraphs 19a-66a, wherein Z is —N(CH$_2$COOH)$_2$.

74a. Insulin derivative according paragraphs 19a-66a, wherein Z is —SO$_3$H.

75a. Insulin derivative according paragraphs 19a-66a, wherein Z is —PO$_3$H$_2$.

76a. Insulin derivative according paragraphs 19a-66a, wherein Z is O—SO$_3$H.

77a. Insulin derivative according paragraphs 19a-66a, wherein Z is O—PO$_3$H$_2$.

78a. Insulin derivative according paragraphs 19a-66a, wherein Z is tetrazo-5-lyl.

79a. Insulin derivative according paragraphs 19a-66a, wherein Z is a bicyclic system consisting of a 6 membered and a 5 membered ring, where Z is bound via the 6 membered ring.

80a. Insulin derivative according paragraph 79a, where the 5 membered ring contains three nitrogen, which are not shared with the 6 membered ring.

81a Insulin derivative according to any of the paragraphs 1a-80a, wherein the parent insulin is human insulin or porcine insulin 82a Insulin derivative according to any of the paragraphs 1a-80a, wherein the parent insulin is an insulin analogue.

83a. Insulin derivative according to any of paragraphs 81a-82a, wherein the amino acid residue at position B30 of the parent insulin is Lys or has been deleted.

84a. Insulin derivative according to paragraph 83a, wherein the parent insulin is desB30 human insulin.

85a. Insulin derivative according to any of paragraphs 81a-84a, wherein the amino acid residue at position B1 of the parent insulin has been deleted.

86. Insulin derivative according to any of paragraphs 81-85, wherein the amino acid residue in position A21 of the parent insulin is Gly or Asn.

87a. Insulin derivative according to any of paragraphs 81a-86a, wherein the amino acid residue at position B3 of the parent insulin is Lys 88a. Insulin derivative according to any of paragraphs 81a-87a, wherein the amino acid residue at position B28 of the parent insulin is Asp or Lys.

89a. Insulin derivative according to any of paragraphs 81a-88a, wherein the amino acid residue at position B29 of the parent insulin is Pro or Thr.

90a. Insulin derivative according to paragraph 88a, wherein the parent insulin is AspB28 human insulin 91a. Insulin derivative according to paragraph 86a, wherein the parent insulin is GlyA21 human insulin or GlyA21desB30 human insulin or GlyA21ArgB31ArgB32 human insulin.

92a. Insulin derivative according to paragraph 87a, wherein the parent insulin is LysB3GluB29 human insulin.

93a. Insulin derivative according to paragraph 88a-89a, wherein the parent insulin is LysB28ProB29 human insulin 94a. Insulin derivative according to paragraph 83a and 89a, wherein the parent insulin is ThrB29LysB30 human insulin 95a. A zinc complex of an insulin derivative according to any one of the preceding paragraphs wherein each insulin hexamer binds two zinc ions, three zinc ions four zinc ions, five zinc ions or six zinc ions.

96a. A pharmaceutical composition for the treatment of diabetes in a patient in need of such treatment, comprising a therapeutically effective amount of an insulin derivative according to any of the preceeding paragraphs together with a pharmaceutically acceptable carrier.

97a. A pharmaceutical composition for the treatment of diabetes in a patient in need of such treatment, comprising a therapeutically effective amount of an insulin derivative according to any of the preceeding paragraphs in mixture with an insulin or an insulin analogue which has a rapid onset of action, together with a pharmaceutically acceptable carrier.

98a. A method of treating diabetes in a patient in need of such a treatment, comprising administering to the patient a therapeutically effective amount of an insulin derivative according to any of the preceeding paragraphs together with a pharmaceutically acceptable carrier.

99a. A method of treating diabetes in a patient in need of such a treatment, comprising administering to the patient a therapeutically effective amount of an insulin derivative according to any of the preceeding paragraphs in mixture with an insulin or an insulin analogue which has a rapid onset of action, together with a pharmaceutically acceptable carrier.

100a. A method according to paragraphs 98a or 99a for pulmonary treatment of diabetes 101a. A mixture of an insulin derivative according to any of paragraphs 1a-95a and a rapid acting insulin analogue selected group consisting of AspB28 human insulin; LysB28ProB29 human insulin and LysB3GluB29 human insulin.

102a. Insulin derivative according to any of paragraphs 1a-95a selected from the group consisting of $N^{\epsilon B29}$-(12-(4-carboxyphenyl) dodecanoyl-gamma-Glu) desB30 insulin, $N^{\epsilon B29}$-(11-(4-Carboxyphenyl) undecanoyl gamma-Glu) desB30 insulin, $N^{\epsilon B29}$-(12-(3-Carboxyphenyl) dodecanoyl gamma-Glu desB30 insulin, $N^{\epsilon B29}$-(9-[4-(2-Carboxyethyl)phenyl]nonanoyl) gamma-Glu) desB30 insulin, or $N^{\epsilon B29}$-(4-[11-(4-Carboxyphenyl) undecanoylamino]butyryl) desB30 insulin 103a. Insulin derivative as described in the examples.

The present invention is further illustrated by the following examples which, however, are not to be construed as limiting the scope of protection.

EXAMPLES

HPLC-MS

Method A

The following instrumentation was used:

Hewlett Packard series 1100 G1312A Bin Pump

Hewlett Packard series 1100 Column compartment

Hewlett Packard series 1100 G1315A DAD diode array detector

Hewlett Packard series 1100 MSD

Sedere 75 Evaporative Light Scattering detector

The instrument was controlled by HP Chemstation software. The HPLC pump was connected to two eluent reservoirs containing:

| A: | 0.05% TFA in water |
| B: | 0.05% TFA in acetonitrile |

The analysis is performed at 40° C. by injecting an appropriate volume of the sample (preferably 1 µl) onto the column which is eluted with a gradient of acetonitrile.

The analysis is performed at by 40° C. injecting an appropriate volume of the sample (1 µl) onto the column which is eluted with a gradient of acetonitrile.

The HPLC conditions, detector settings and mass spectrometer settings used are giving in the following:

| Column: | Waters Xterra MS C-18 × 3 mm id 5 µm |
| Gradient: | 5%-95% acetonitrile linear during 3 min at 2.7 ml/min |
| Detection: | 210 nm (analogue output from DAD) |
| | ELS (analogue output from ELS) |

After the DAD the flow was divided yielding approx 1 ml/min to the ELS and 0.5 ml/min to the MS.

HPLC-MS

Method B

This method is the same as for the HPLC-MS (Method A) method, except the gradient runs from 50-99% acetonitrile.

HPLC-MS

Method C

The following instrumentation is used:

Hewlett Packard series 1100 G1312A Bin Pump

Hewlett Packard series 1100 G13 15A DAD diode array detector

Sciex3000 triplequadropole mass spectrometer

Gilson 215 micro injector

Sedex55 evaporative light scattering detector

Pumps and detectors are controlled by MassChrom 1.1.1 software running on a Macintosh G3 computer. Gilson Unipoint Version 1.90 controls the auto-injector.

The HPLC pump is connected to two eluent reservoirs containing:

| | |
|---|---|
| A: | 0.01% TFA in water |
| B: | 0.01% TFA in acetonitrile |

The analysis is performed at room temperature by injecting an appropriate volume of the sample (preferably 10 μl) onto the column, which is eluted, with a gradient of acetonitrile. The eluate from the column passed through the UV detector to meet a flow splitter, which passed approximately 30 μl/min (1/50) through to the API Turbo ion-spray interface of API 3000 spectrometer. The remaining 1.48 ml/min (49/50) is passed through to the ELS detector.

The HPLC conditions, detector settings and mass spectrometer settings used are giving in the following table.

| | |
|---|---|
| Column | Waters X-Terra C18, 5μ, 50 mm × 3 mm id |
| Gradient | 5%-90% acetonitrile linearly during 7.5 min at 1.5 ml/min |
| Detection | 210 nm (analogue output from DAD) |
| MS | ionisation mode API Turbo ion-spray |
| ELS | Gain 8 and 40° C. |

HPLC

Method A

Buffer A: 10 mM tris, 15 mM $(NH_4)_2SO_4$, pH adjusted to 7.3 with $4NH_2SO_4$, 20% v/v acetonitrile
Buffer B: 80% v/v acetonitrile
Flow: 1.5 ml/min
Gradient: 0-20 min 10-50% B
Column: Phenomerex, Jupiter 4.6 mm×150 mm, $C_4$, 5μ, 300 Å
Column temperature: 40° C.

Example 1

$N^{\epsilon B29}$-(12-(4-carboxyphenyl) dodecanoyl-γ-Glu) desB30 Insulin

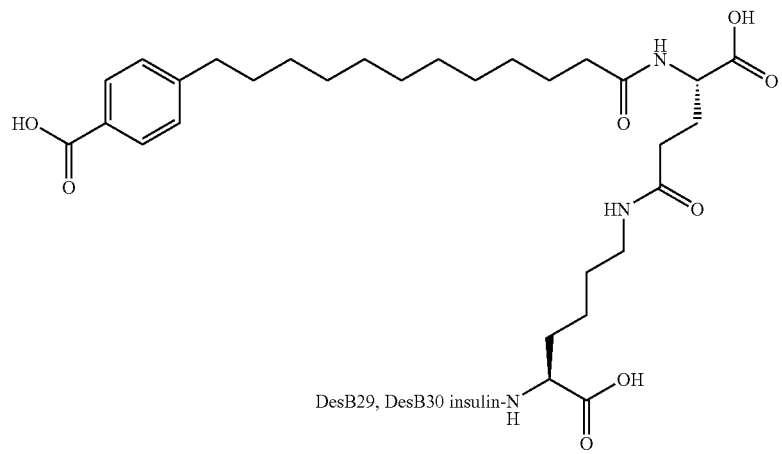

General Procedure (A): Tert-Butyl Protection of Carboxylic Acids

Step 1: 4-Iodobenzoic Acid tert-butyl Ester

4-Iodobenzoic acid (10 g, 40.3 mmol) was dissolved in dry toluene (100 ml, dried over mol. sieves). The solution was heated to 70° C. under a flow of nitrogen. A solution of N,N'-dimethylformamide di-tert-butyl acetal (24.6 g, 121 mmol) in toluene (25 ml) was added over ca. 30 min. The reaction was mixed for 16 h. At some point the heating unit failed, So the reaction cooled from 70° C. to rt. The solution was heated to 70° C. for and mixed for 5 h. The sample was concentrated under vacuum, and AcOEt (400 ml) was added. The solution was then washed with 1:1 sat. $NaHCO_3$/water (150 ml), and sat. $NaHCO_3$, water and sat. NaCl (75 ml each). The organic phase was dried ($MgSO_4$) and concentrated under vacuum to yield a light brown oil.

HPLC-MS (Method A): m/z: 327 (M+23), $R_t$=2.43 min.
$^1$H-NMR ($CDCl_3$, 400 MHz) δ 7.77 (d, 2H), 7.69 (d, 2H), 1.58 (s, 9H).

General Procedure (B): Methyl Ester Protection of Carboxylic Acids

Step 2: 12-Bromododecanoic Acid Methyl Ester

12-Bromododecanoic acid (10 g, 35.8 mmol) was stirred with methanol (60 ml) and Toluene (180 ml). Trimethyl orthoformate (38 g, 358 mmol) and Amberlyst A-15 (ca. 1 g) were added. The reaction was mixed for 16 h. At some point the heating unit failed, So the reaction cooled from 70° C. to rt. The solution was heated to 70° C. and mixed for 24 h. TLC (2:1 heptane/AcOEt) indicated the reaction was incomplete. Trimethyl orthoformate (38 g, 358 mmol) and Amberlyst A-15 (1.4 g) were added, and the solution was stirred at 70° C. for 16 h. The sample was concentrated under vacuum to yield a brown oil (9.87 g). Vacuum distillation at 0.09 torr yielded two fractions of colorless oil (109-117° C., 6.95 g; 117-129° C., 1.17 g). These were combined and dissolved in AcOEt (100 ml) and washed with Sat. $NaHCO_3$ (2×40 ml), dried over $MgSO_4$ and concentrated under vacuum. The oil was dissolved in 20:1 AcOEt/TEA (10 ml) and added to a bed of silica (3 cm×7.5 cm dia). The column was eluted with AcOEt/ TEA 20:1 (200 ml), and the filtrate was concentrated under vacuum. The oil was dissolved in AcOEt (100 ml) and washed with 1 N HCl (2×40 ml), dried over $MgSO_4$ and concentrated under vacuum to yield a colorless oil (7.52 g, 72% yield).

HPLC-MS (Method B): m/z: 293 and 295 (M, M+2), $R_t$=1.64 min.
$^1$H-NMR ($CDCl_3$, 300 MHz) δ 3.67 (s, 3H), 3.41 (t, 2H), 2.30 (t, 2H), 1.80-1.90 (m, 2H), 1.52-1.71 (m, 2H), 1.37-1.52 (m, 2H), 1.28 (s, 12H).

General Procedure (C): Br—I Exchange

Step 3: 12-Iodododecanoic Acid Methyl Ester

12-Bromododecanoic acid methyl ester (5.65 g, 19.3 mmol) was dissolved in acetone (50 ml). Sodium iodide (14.4 g, 96 mmol) was added and the reaction was refluxed under nitrogen for 20 h. The sample was concentrated under vacuum. Water (100 ml) was added, and the mixture was extracted with AcOEt (2×100 ml). The organic extracts were pooled and washed with water plus a small amount of sat. NaCl and sat. NaCl (100 ml each), dried over $MgSO_4$, and concentrated to yield a light yellow oil (6.37 g, 97%).

HPLC-MS (Method B): m/z: 341 (M+1), $R_t$=1.88 min.
$^1$H-NMR ($CDCl_3$, 300 MHz) δ 3.67 (s, 3H), 3.19 (t, 2H), 2.30 (t, 2H), 1.77-1.87 (m, 2H), 1.53-1.68 (m, 2H), 1.18-1.45 (m, 14H).

General Procedure (D): C—C Coupling

Step 4: 4-(11-Methoxycarbonylundecyl)benzoic Acid tert-butyl Ester

All glassware was dried prior to use. THF was dried over molecular sieves. LiCl was dried at 150° C. for 1 h, then stored in a closed bottle. All reaction solutions were made under nitrogen, and the solutions were transferred via syringe. 4-Iodobenzoic acid tert-butyl ester (3 g, 9.9 mmol) was dissolved in THF (7.5 ml), and cooled to −20 to −30° C. Isopropyl magnesium chloride (10.9 mmol, 2M in THF) was added over 5 min, and the solution was stirred for 30 min. A solution of CuCN (0.97 g, 10.9 mmol) and LiCl (0.92 g, 21.7 mmol) in 7.5 ml THF was added. The reaction was removed from the cold bath and allowed to warm to rt. After 15 min, trimethylphosphite (0.62 ml) was added. After stirring for 5 min—iodododecanoic acid methyl ester (2.69 g, 7.89 mmol) was added in a solution of THF (5 ml). After stirring for 16 h, the reaction was quenched with sat. $NH_4Cl$ (6 ml). Water (100 ml) was added and the solution was extracted with AcOEt (3×100 ml). The organic extracts were pooled ant washed with water (100 ml) (some sat. NaCl and MeOH was added to aid phase separation) and sat. NaCl (100 ml), dried over $MgSO_4$ and concentrated under vacuum to yield a two-phased residue (5.85 g). The residue was dissolved in AcOEt and added drop wise to a bed of silica in a glass filter (7.5 cm dia×3 cm). 200 ml of AcOEt was washed through the silica, and the filtrate was concentrated to yield a residue. This was dissolved in DCM (10 ml) and purified by flash chromatography (15 cm×40 mm, eluant 9:1 heptane/AcOEt). The relevant fractions were pooled and concentrated under vacuum. This was dissolved in 9:1 heptane/AcOEt (7 ml) and purified again by flash chromatography (15 cm×40 mm, eluant 9:1 heptane/AcOEt) to yield a colorless oil (185 mg).

$^1$H-NMR ($CDCl_3$, 300 MHz) δ 7.90 (d, 2H), 7.21 (d, 2H), 3.66 (s, 3H), 2.64 (t, 2H), 2.30 (t, 2H), 1.53-1.68 (m, 13H), 1.12-1.37 (m, 14H).

General Procedure (E): Saponification

Step 5: 4-(11-Methoxycarbonylundecyl)benzoic Acid 4-(11-Methoxycarbonylundecyl)benzoic acid tert-butyl ester (185 mg, 0.47 mmol) was dissolved in THF (2 ml), and 1 N NaOH (0.497 mmol) was added over 1 min. The mixture was stirred for 16 h at rt. AcOEt (50 ml) was added and the solution was washed with 5% AcOH (2×25 ml), dried over $MgSO_4$ and concentrated under vacuum to the product (153 mg).

HPLC-MS (Method A): m/z: 399 (M+23), $R_t$=2.86 min.
$^1$H-NMR ($CDCl_3$, 300 MHz) δ 7.90 (d, 2H), 7.21 (d, 2H), 2.64 (t, 2H), 2.35 (t, 2H), 1.54-1.70 (m, 13H), 1.15-1.40 (m, 16H (14H theoret.)).

General Procedure (F): Amide Formation with EDAC

Step 6: (S)-2-[12-(4-tert-Butoxycarbonylphenyl) dodecanoylamino]pentanedioic Acid 5-benzyl Ester 1-tert-butyl Ester 4-(11-Methoxycarbonylundecyl)benzoic acid (153 mg, 0.41 mmol) was dissolved DMF (3 ml). HOBt (60 mg, 0.45 mmol), EDAC (86 mg, 0.45 mmol) and DIEA (172 mg, 1.34 mmol) were added, and the solution was stirred at rt for 30 min under nitrogen. H-Glu-(OBzl)-OtBu hydrogen chloride (141 mb, 0.43 mmol) was added at the solution was stirred at rt for 16 h. The sample was concentrated under vacuum. AcOEt (50 ml) was added and the solution was washed once with water and twice with 5% AcOH and sat. NaHCO$_3$ (25 ml each), dried over MgSO$_4$ and concentrated under vacuum to yield a slightly yellow oil (249 mg). The product was purified by flash chromatography (7.5 cm×40 mm, eluant 1:2 AcOEt/heptane) to yield a colorless residue (177 mg).

HPLC-MS (Method B): m/z: 652 (M+1), $R_t$=2.68 min.

$^1$H-NMR (CDCl$_3$, 400 MHz) δ 7.89 (d, 2H), 7.35 (s, 5H), 7.21 (d, 2H), 6.06 (d, 1H), 5.11 (s, 2H), 4.52 (m, 1H), 2.64 (t, 2H), 2.30-2.54 (m, 2H), 2.13-2.27 (m, 3H), 1.90-2.03 (m, 1H), 1.53-1.67 (m, 19H (13H+water), 1.46 (s, 9H), 1.18-1.36 (m, 14H).

General Procedure (G): Removal of Benzyl Ester

Step 7: (S)-2-[12-(4-tert-Butoxycarbonylphenyl) dodecanoylamino]pentanedioic Acid 1-tert-butyl Ester (S)-2-[12-(4-tert-Butoxycarbonylphenyl) dodecanoylamino]pentanedioic acid 5-benzyl ester 1-tert-butyl ester (175 mg, 0.27 mmol) was dissolved in THF and placed under nitrogen. 10% palladium on carbon (ca. 20 mg) was added, and the flask was evacuated and filled with nitrogen three times. The flask was equipped with balloon filled with hydrogen, and stirred at rt overnight. The solution was filtered through celite, washing with THF. The filtrate was concentrated under vacuum to yield an oil (0.15 g).

HPLC-MS (Method B): m/z: 584 (M+23), $R_t$=1.95 min.

General Procedure (H): HSTU Activation of Carboxylic Acid

Step 8: (S)-2-[12-(4-tert-Butoxycarbonylphenyl) dodecanoylamino]pentanedioic Acid 5-tert-butyl Ester 1-(2,5-dioxopyrrolidin-1-yl) Ester (S)-2-[12-(4-tert-Butoxycarbonylphenyl) dodecanoylamino]pentanedioic acid 1-tert-butyl ester (158 mg, 0.28 mmol) was dissolved in THF (6 ml). DIEA (48 µl, 0.28 mmol) was added, and the solution was placed in an ice bath. HSTU (101 mg, 0.28 mmol) was added, and the solution was stirred for 16 h, warming to rt slowly. The solvent was removed under vacuum, and the residue was partitioned between AcOEt (25 ml) and 5% AcOH (15 ml). The organic phase was washed with 5% AcOH (2×15 ml), and saturated NaHCO$_3$, dried, and concentrated under vacuum to yield an oil (0.16 g).

HPLC-MS (Method B): m/z: 681 (M+23), $R_t$=2.17 min.

General Procedure (I): Modification of Insulin and Deprotection of Functional Groups

Step 9: B29N(eps)-12-(4-carboxyphenyl) dodecanoyl-gamma-Glu desB30 Insulin

Des-B30 insulin (126 mg, 0.022 mmol) was dissolved by adding 100 mM Na$_2$CO$_3$ (1.5 ml) and acetonitrile (1.5 ml) in a 10 ml round bottom-flask. (S)-2-[12-(4-tert-Butoxycarbonylphenyl) dodecanoylamino]pentanedioic acid 5-tert-butyl ester 1-(2,5-dioxopyrrolidin-1-yl) ester (17 mg, 0.026 mmol) was added in acetonitrile (750 ul) and Na$_2$CO$_3$ (750 ul) was added so the final solution was 50:50 100 mM Na$_2$CO$_3$/acetonitrile. The solution was stirred at rt for 1 h. The solution was transferred to a 15 ml centrifuge tube, washing with Milli-Q water (6 ml). The solution was cooled on ice, and the pH was adjusted to 5.1 by adding 1N HCl, which lead to precipitation. The tube was centrifuged at 5000 rpm for 10 min at 10° C. The solvent was decanted from the solid. 95:5 TFA/water (2.5 ml) was added to the solid. The solution was poured into a RB-flask, washing with more 95:5 TFA/water (2.5 ml). The solution was stirred for 30 min at rt, and concentrated under vacuum. DCM was added and removed twice, and the flask was dried under vacuum at rt. The product was purified by preparative HPLC (2 cm dia. C$_{18}$ column, acetonitrile/water/0.05% TFA). The relevant fractions were pooled (two batches) and diluted 1:1 with water. The solutions were cooled on ice, and the precipitation was induced by adjusting the pH to ca. 5 with 1 N NaOH. The samples were centrifuged (5000 rpm, 10 min, 5° C.). The liquid was decanted off and the pellets were lyophilized to yield a white solid (25.9 mg+6.7 mg). The 25.9 mg was further purified using preparative HPLC (1 cm dia. C$_4$ column, acetonitrile/water/0.05% TFA) to yield a white solid (13 mg).

HPLC (Method A): $R_t$=4.62 min.

MALDI-MS: (CHCA) m/z: 6140 (M=6138).

Example 2

$N^{\epsilon B29}$-(11-(4-Carboxyphenyl) undecanoyl γ-Glu) desB30 Insulin

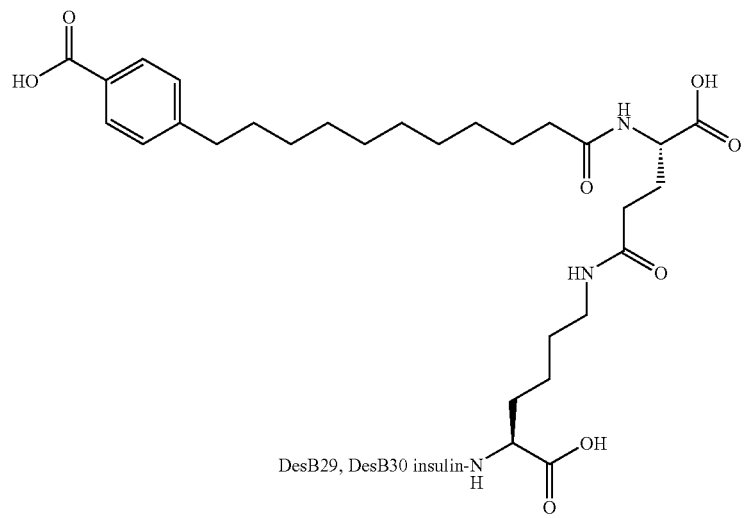

Step 1: 11-Iodo Undecanoic Acid Methyl Ester

11-Bromo undecanoic acid methyl ester (20.2 g, 72.3 mmol) was dissolved in acetone (200 ml). Sodium iodide (54 g, 361 mmol) was added and reaction was refluxed under nitrogen for 16 h. After cooling to rt the salts were filtered off. The filtrate was concentrated under vacuum and water (200 ml) was added. The solution was extracted with AcOEt (2×100 ml) adding some sat. NaCl to aid phase separation. The organic extracts were pooled and washed with water (100 ml) plus a little sat. NaCl, and sat. NaCl (50 ml). Dry over $MgSO_4$. The solution was a red-orange color. Three teaspoons of activated charcoal were added. After mixing, the solution was filtered through a bed of celite. The filtrate was concentrated under vacuum to yield a light yellow oil (20.96 g, 89%).

HPLC-MS (Method B): m/z: 327 (M+1), $R_t$=1.59 min.

$^1$H-NMR (CDCl$_3$, 300 MHz) δ 3.67 (s, 3H), 3.19 (t, 2H), 2.30 (t, 2H), 1.74-1.89 (m, 2H), 1.53-1.70 (m, 2H), 1.34-1.46 (m, 2H), 1.28 (br, 10H).

General Procedure (D2): C—C Coupling with Piperidine Work Up

Step 2: 4-(10-Methoxycarbonyldecyl)benzoic Acid tert-butyl Ester

All glassware was dried prior to use. THF was dried over molecular sieves. LiCl was dried at 150° C. for 1 h, then stored in a closed bottle. All reaction solutions were made under nitrogen, and the solutions were transferred via syringe. 4-Iodobenzoic acid tert-butyl ester (1.2 g, 3.95 mmol) was dissolved in THF (3 ml) and cooled to −30° C. Isopropyl magnesium chloride (4.34 mmol, 2M in THF) was added over 5 minutes, and the solution was stirred for 1 hr at a temperature between −18° C. to −25° C. The solution was cooled to −22° C., and a mixture of CuCN (0.389 g, 4.34 mmol) and LiCl (0.368 g, 8.68 mmol) in THF (4.2 ml) was then added. The reaction vessel was removed from cooling and allowed to warm to RT (ca. 10 min). Trimethylphosphite (0.95 ml) was added, and after stirring for 5 min at rt, a solution of 11-iodo undecanoic acid methyl ester (1.0 g, 3.16 mmol) in THF (3 ml) was added. The solution was mixed at rt for 16 h. Sat. NH$_4$Cl (3 ml) was added, and the solution was poured into water (60 ml). The solution was extracted with AcOEt (3×35 ml). The organic extracts were pooled and washed with water (30 ml) using some Sat. NaCl to aid phase separation. The solvent was removed under vacuum to yield a biphasic residue. AcOEt (ca 2 ml) was added and the flask was swirled gently. Not all of the thick white residue dissolved. The portion which dissolved was added to a column of silica (50 g) and eluted with AcOEt:heptane 1:11. The appropriate fractions were concentration under vacuum to yield an oil (1.25 g). The oil was dissolved in acetone (30 ml), and piperidine (1 ml) was added. NaI (0.8 g) was added and the mixture was stirred and refluxed for 16 h. The mixture was concentrated under vacuum and partitioned between AcOEt (50 ml) and 1 N HCl (25 ml). The organic phase was washed with 1 N HCl (2×25 ml), dried over MgSO$_4$, and concentrated under vacuum to yield a colorless oil (1.1 g). The product was purified by flash chromatography (eluant: AcOEt:heptane 1:11, 150 g silica) to yield a colorless oil (0.72 g, 61%).

HPLC-MS (Method B): m/z: 399 (M+23), $R_t$=2.46 min.

$^1$H-NMR (CDCl$_3$, 300 MHz) δ 7.90 (d, 2H), 7.21 (d, 2H), 3.66 (s, 3H), 2.64 (t, 2H), 2.30 (t, 2H), 1.48-1.70 (m, 13H), 1.27 (br, 12H).

The remaining steps were performed in analogous fashion to Example 1.

Step 3: 4-(10-Carboxydecyl)benzoic Acid tert-butyl Ester

The compound was prepared in analogous fashion to general procedure (E) to yield a white solid (0.68 g).

HPLC-MS (Method B): m/z: 385 (M+23), $R_t$=2.02 min.

$^1$H-NMR (CDCl$_3$, 300 MHz) δ 7.90 (d, 2H), 7.21 (d, 2H), 2.64 (t, 2H), 2.34 (t, 2H), 1.53-1.71 (m, 13H), 1.28 (br, 12H).

Step 4: (S)-2-[11-(4-tert-Butoxycarbonylphenyl) undecanoylamino]pentanedioic Acid 5-benzyl Ester 1-tert-butyl Ester The compound was prepared in analogous fashion to general procedure (F) to yield a colorless oil (303 mg).

HPLC-MS (Method B): m/z: 660 (M+23), $R_t$=2.44 min.

$^1$H-NMR (CDCl$_3$, 400 MHz) δ 7.89 (d, 2H), 7.35 (m, 5H), 7.21 (d, 2H), 6.05 (d, 1H), 5.11 (s, 2H), 4.52 (m, 1H), 2.63 (t, 2H), 2.30-2.53 (m, 2H), 2.12-2.26 (m, 3H), 1.89-2.03 (m, 1H), 1.52-1.67 (m, 13H), 1.46 (s, 9H), 1.26 (br, 12H).

Step 5: (S)-2-[11-(4-tert-Butoxycarbonylphenyl) undecanoylamino]pentanedioic acid 1-tert-butyl Ester The compound was prepared in analogous fashion to general procedure (G) to yield a colorless oil (260 mg).

HPLC-MS (Method B): m/z: 570 (M+23), $R_t$=1.71 min.

Step 6: (S)-2-[11-(4-tert-Butoxycarbonylphenyl) undecanoylamino]pentanedioic Acid 5-tert-butyl Ester 1-(2,5-dioxopyrrolidin-1-yl) ester The compound was prepared in analogous fashion to general procedure (H).

HPLC-MS (Method B): m/z: 667 (M+23), $R_t$=1.93 min.

$^1$H-NMR (CDCl$_3$, 400 MHz) δ 7.89 (d, 2H), 7.21 (d, 2H), 6.20 (d, 1H), 4.60 (m, 1H), 2.84 (s, 4H), 2.67-2.78 (m, 1H), 2.56-2.67 (m, 3H), 2.26-2.40 (m, 1H), 2.21 (t, 2H), 2.05-2.15 (m, 1H), 1.54-1.67 (m, 13H), 1.48 (s, 9H), 1.26 (br, 14H, theoret. 12H+AcOEt).

Step 7: $N^{\epsilon B29}$-(11-(4-Carboxyphenyl) undecanoyl gamma-Glu) desB30 Insulin The compound was prepared in analogous fashion to general procedure (I).
HPLC (Method A): $R_t$=6.19 min.
MALDI-MS: (CHCA) m/z: 6132 (M=6124, reference standard (M=5706) showed m/z=5712).
HPLC-MS (Method C): m/z: 1532.4 ((M+4)/4=1532), $R_t$=3.44 min.

Example 3

$N^{\epsilon B29}$-(12-(3-Carboxyphenyl) dodecanoyl γ-Glu desB30 Insulin

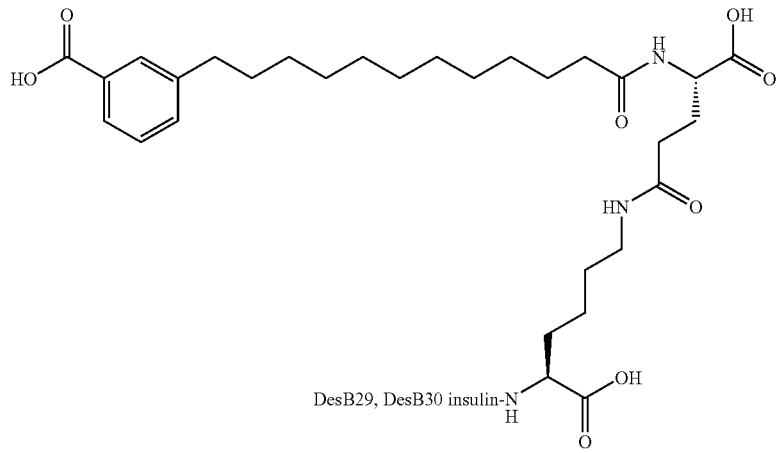

Step 1: 3-Iodobenzoic acid tert-butyl Ester

The compound was prepared in analogous fashion to general procedure (A) to yield a light brown oil (1.8 g).
HPLC-MS (Method A): m/z: 327 (M+23), $R_t$=2.42 min.
$^1$H-NMR (CDCl$_3$, 300 MHz) δ 8.31 (s, 1H), 7.95 (d, 1H), 7.85 (d, 1H), 7.16 (t, 1H), 1.59 (s, 9H).

Step 2: 3-(11-Methoxycarbonylundecyl)benzoic Acid tert-butyl Ester

The compound was prepared in analogous fashion to general procedure (D).
HPLC-MS (Method B): m/z: 413 (M+23), $R_t$=2.54 min.
$^1$H-NMR (CDCl$_3$, 400 MHz) δ 7.78-7.82 (m, 2H), 7.28-7.36 (m, 2H), 3.66 (s, 3H), 2.63 (t, 2H), 2.30 (t, 2H), 1.58-1.71 (m, 13H), 1.21-1.37 (m, 14H).

Step 3: 3-(11-Carboxy-undecyl)benzoic Acid tert-butyl Ester

The compound was prepared in analogous fashion to general procedure (E) to yield 290 mg.
HPLC-MS (Method B): m/z: 399 (M+23), $R_t$=1.89 min.
$^1$H-NMR (CDCl$_3$, 300 MHz) δ 7.73-7.88 (m, 2H), 7.27-7.38 (m, 2H), 2.64 (t, 2H), 2.35 (t, 2H), 1.54-1.70 (m, 13H), 1.20-1.41 (m, 14H).

Step 4: (S)-2-[12-(3-tert-Butoxycarbonylphenyl) dodecanoylamino]pentanedioic Acid 5-benzyl Ester 1-tert-butyl Ester The compound was prepared in analogous fashion to general procedure (F) to yield 400 mg.
HPLC-MS (Method B): m/z: 652 (M+1), $R_t$=2.56 min.
$^1$H-NMR (CDCl$_3$, 300 MHz) δ 7.74-7.85 (m, 2H), 7.27-7.41 (m, 7H), 6.06 (d, 1H), 5.11 (s, 2H), 4.45-4.58 (m, 1H), 2.63 (t, 2H), 2.30-2.55 (m, 2H), 2.12-2.27 (m, 3H), 1.89-2.04 (m, 1H), 1.52-1.67 (m, 13H), 1.46 (s, 9H), 1.15-1.37 (m, 14H).

Step 5: (S)-2-[12-(3-tert-Butoxycarbonylphenyl) dodecanoylamino]pentanedioic acid 1-tert-butyl Ester The compound was prepared in analogous fashion to general procedure (G) to yield 370 mg.
HPLC-MS (Method B): m/z: 584 (M+23), $R_t$=1.86 min.
$^1$H-NMR (CDCl$_3$, 400 MHz) δ 7.77-7.83 (m, 2H), 7.28-7.37 (m, 2H), 6.25 (d, 1H), 4.45-4.63 (m, 1H), 2.63 (t, 2H), 2.32-2.54 (m, 2H), 2.14-2.32 (m, 3H), 1.87-1.97 (m, 1H), 1.56-1.68 (m, 13H), 1.47 (s, 9H), 1.19-1.37 (m, 14H).

Step 6: (S)-2-[12-(3-tert-Butoxycarbonylphenyl) dodecanoylamino]pentanedioic acid 5-tert-butyl Ester 1-(2,5-dioxopyrrolidin-1-yl) ester The compound was prepared in analogous fashion to general procedure (H) to yield 390 mg.
HPLC-MS (Method B): m/z: 681 (M+23), $R_t$=2.06 min.

Step 7: $N^{\epsilon B29}$-(11-(4-Carboxyphenyl) undecanoyl gamma-Glu) desB30 Insulin The compound was prepared in analogous fashion to general procedure (I) to yield 51 mg.
HPLC (Method A): $R_t$=6.25 min.
MALDI-MS: (CHCA) m/z: 6142 (M=6138, reference standard (M=5706) showed m/z=5711).
HPLC-MS (Method C): m/z: 1535.7 ((M+4)/4=1535.5), $R_t$=3.22 min.

Example 4

N$^{εB29}$-(9-[4-(2-Carboxyethyl)phenyl]nonanoyl) γ-Glu) desB30 Insulin

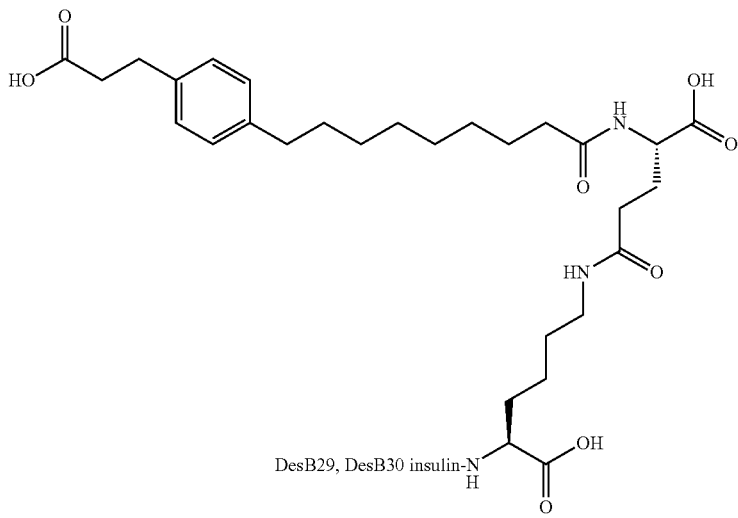

HPLC-MS (Method B): m/z: 299 (M+1), R$_t$=1.19 min.
$^1$H-NMR (CDCl$_3$, 300 MHz) δ 3.67 (s, 3H), 3.18 (t, 2H), 2.31 (t, 2H), 1.73-1.93 (m, 2H), 1.54-1.72 (m, 2H), 1.24-1.47 (m, 8H).

Step 1: 3-(4-Iodophenyl) propionic Acid tert-butyl Ester

The compound was prepared in analogous fashion to general procedure (A) to yield to yield 3.97 g.

HPLC-MS (Method A): m/z: 355 (M+23), R$_t$=2.39 min.
$^1$H-NMR (CDCl$_3$, 300 MHz) δ 7.60 (d, 2H), 6.96 (d, 2H), 2.84 (t, 2H), 2.50 (t, 2H), 1.41 (s, 9H).

Step 2: 9-Bromononanoic Acid Methyl Ester

The compound was prepared in analogous fashion to general procedure (B) to yield a colorless oil (6.56 g).

$^1$H-NMR (CDCl$_3$, 300 MHz) δ 3.67 (s, 3H), 3.40 (t, 2H), 2.31 (t, 2H), 1.78-1.93 (m, 2H), 1.56-1.70 (m, 2H), 1.36-1.50 (m, 2H), 1.26-1.36 (m, 6H).

Step 3: 9-Iodo-nonanoic Acid Methyl Ester

The compound was prepared in analogous fashion to general procedure (C) to yield a oil (5.48 g).

Step 4: 9-[4-(2-tert-Butoxycarbonylethyl)phenyl]nonanoic Acid Methyl Ester

The compound was prepared in analogous fashion to general procedure (D2) to yield 590 mg.
HPLC-MS (Method B): m/z: 399 (M+23), R$_t$=2.10 min.
$^1$H-NMR (CDCl$_3$, 300 MHz) δ 7.09 (m, 4H), 3.66 (s, 3H), 2.87 (t, 2H), 2.47-2.60 (m, 4H), 2.29 (t, 2H), 1.50-1.68 (m, 4H), 1.42 (s, 9H), 1.26-1.36 (s-br, 8H).

Step 5: 9-[4-(2-tert-Butoxycarbonylethyl)phenyl]nonanoic Acid

The compound was prepared in analogous fashion to general procedure (E) to yield a white residue (270 mg).
HPLC-MS (Method B): m/z: 385 (M+23), R$_t$=1.44 min.
$^1$H-NMR (CDCl$_3$, 300 MHz) δ 7.09 (m, 4H), 2.87 (t, 2H), 2.47-2.61 (m, 4H), 2.34 (t, 2H), 1.49-1.73 (m, 4H), 1.41 (s, 9H), 1.23-1.37 (s-br, 8H).

Step 6: (S)-2-{9-[4-(2-tert-Butoxycarbonylethyl)phenyl]nonanoylamino}pentanedioic Acid 5-benzyl Ester 1-tert-butyl Ester The compound was prepared in analogous fashion to general procedure (F) to yield 340 mg.

HPLC-MS (Method B): m/z: 660 (M+23), $R_t$=2.28 min.
$^1$H-NMR (CDCl$_3$, 300 MHz) δ 7.29-7.42 (m, 5H), 7.09 (m, 4H), 6.06 (d, 1H), 5.11 (s, 2H), 4.45-4.61 (m, 1H), 2.87 (t, 2H), 2.30-2.61 (m, 6H), 2.10-2.28 (m, 3H), 1.88-2.03 (m, 1H), 1.49-1.74 (m, 5H, Theoret. 4H+water), 1.46 (s, 9H), 1.42 (s, 9H), 1.22-1.36 (s-br, 8H).

Step 7: (S)-2-{9-[4-(2-tert-Butoxycarbonylethyl)phenyl]nonanoylamino}pentanedioic Acid 1-tert-butyl Ester The compound was prepared in analogous fashion to general procedure (G) to yield 330 mg.
HPLC-MS (Method B): m/z: 547 (M+1), $R_t$=1.46 min.
$^1$H-NMR (CDCl$_3$, 400 MHz) δ 7.09 (m, 4H), 6.25 (d, 1H), 4.49-4.58 (m, 1H), 2.87 (t, 2H), 2.47-2.60 (m, 4H), 2.30-2.47 (m, 2H), 2.14-2.26 (m, 3H), 1.82-1.99 (m, 1H), 1.51-1.68 (m, 4H), 1.47 (s, 9H), 1.41 (s, 9H), 1.25-1.36 (s-br, 8H).

Step 8: (S)-2-{9-[4-(2-tert-Butoxycarbonylethyl)phenyl]nonanoylamino}pentanedioic Acid 1-tert-butyl Ester 5-(2,5-dioxopyrrolidin-1-yl) Ester The compound was prepared in analogous fashion to general procedure (H) to yield 270 mg.
HPLC-MS (Method B): m/z: 667 (M+23), $R_t$=1.71 min.

Step 9: $N^{\epsilon B29}$-(9-[4-(2-Carboxyethyl)phenyl]nonanoyl) gamma-Glu) desB30 Insulin The compound was prepared in analogous fashion to general procedure (I) to yield 26 mg.
HPLC (Method A): $R_t$=5.80 min.
MALDI-MS: (CHCA) m/z: 6129 (M=6124, reference standard (M=5706) showed m/z=5711).
HPLC-MS (Method C): m/z: 1531.8 ((M+4)/4=1532), $R_t$=2.96 min.

Example 5

$N^{\epsilon B29}$-(4-[11-(4-Carboxyphenyl) undecanoylamino] butyryl) desB30 Insulin

Step 1: 4-[10-(2,5-Dioxopyrrolidin-1-yloxycarbonyl)decyl]benzoic Acid tert-butyl Ester The compound was prepared in analogous fashion to general procedure (H), but TSTU was used instead of HSTU.
HPLC-MS (Method B): m/z: 482 (M+23), $R_t$=2.22 min.
$^1$H-NMR (CDCl$_3$, 400 MHz) δ 7.89 (d, 2H), 7.21 (d, 2H), 2.76-2.93 (m, 4H), 2.54-2.68 (m, 2H), 1.67-1.81 (M, 2H), 1.52-1.66 (m, 11H), 1.35-1.43 (M, 2H), 1.19-1.35 (br, 10H).

Step 2

4-[10-(3-Carboxy-propylcarbamoyl)decyl]benzoic Acid tert-butyl Ester

4-[10-(2,5-Dioxopyrrolidin-1-yloxycarbonyl)decyl]benzoic acid tert-butyl ester (300 mg, 0.65 mmol) was dissolved in DMF (3 ml) and 4-amino butyric acid (67 mg, 0.65 mmol). The mixture was stirred for 16 h under nitrogen. The solvent was removed under vacuum and AcOEt (35 ml) was added. The solution was washed with 0.2 N HCl and water (15 ml each). Sat. NaHCO$_3$ was added (not intended) to the organic phase. DCM (50 ml) was added. Some of the organic phase was removed and DCM (100 ml) was added to the aqueous phase and allowed to stand overnight. The mixture was cooled on ice and the pH was adjusted to 1.9 with 4N HCl. The organic phase was isolated, dried over MgSO$_4$ and concentrated under vacuum to yield on oil (220 mg, 76% yield).
HPLC-MS (Method C): m/z: 470 (M+23), $R_t$=5.74 min.
$^1$H-NMR (CDCl$_3$, 400 MHz) δ 7.89 (d, 2H), 7.21 (d, 2H), 5.79 (br, 1H), 3.27-3.40 (m, 2H), 2.64 (t, 2H), 2.40 (t, 2H), 2.18 (t, 2H), 1.78-1.91 (m, 2H), 1.51-1.61 (m, 13H), 1.35-1.43 (M, 2H), 1.17-1.36 (br, 12H).

Step 3: 4-{10-[3-(2,5-Dioxo-pyrrolidin-1-yloxycarbonyl) propylcarbamoyl]decyl}benzoic Acid tert-butyl Ester The compound was prepared in analogous fashion to general procedure (H), but TSTU was used instead of HSTU. Precipitation (DCM/Heptane) yielded white crystals (180 mg, 70% yield).

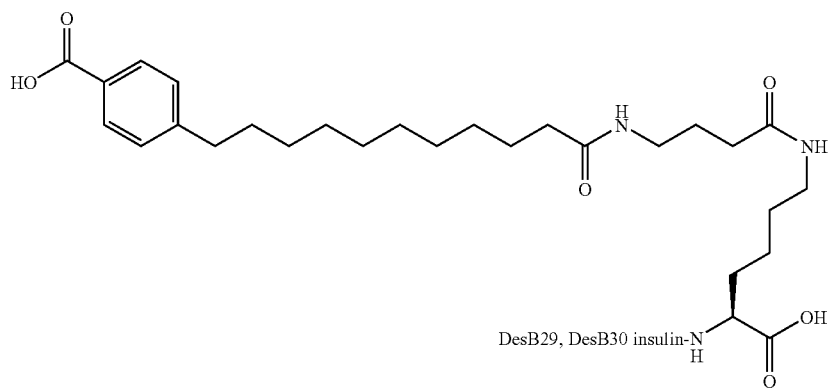

HPLC-MS (Method B): m/z: 568 (M+23), $R_t$=1.60 min.

$^1$H-NMR (CDCl$_3$, 400 MHz) δ 7.89 (d, 2H), 7.21 (d, 2H), 5.83 (br, 1H), 3.30-3.43 (m, 2H), 2.85 (br, 4H), 2.57-2.73 (m, 4H), 2.15 (t, 2H), 1.92-2.07 (m, 2H), 1.56-1.64 (m, 13H), 1.18-1.36 (br, 12H).

Step 4: N$^{εB29}$-(4-[11-(4-Carboxyphenyl) undecanoylamino]butyryl) desB30 Insulin The compound was prepared in analogous fashion to general procedure (I) to yield 30 mg.

HPLC (Method A): $R_t$=7.88 min.

MALDI-MS: (CHCA) m/z: 6067 (M=6080, reference standard (M=5706) showed M-13).

HPLC-MS (Method C): m/z: 1520.9 ((M+4)/4=1521), $R_t$=3.54 min.

Example 6

N$^{εB29}$-[12-(5-Carboxythiophen-2-yl)dodecanoyl] desB30 Insulin

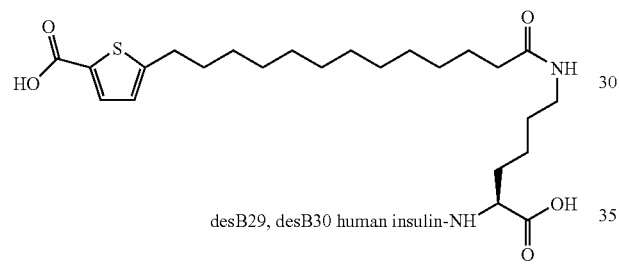

Step 1: Synthesis of 5-Methyl-thioph-ene-2-carboxylic Acid tert-butyl Ester

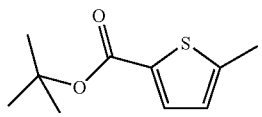

To 5-methylthiophene-2-carboxylic acid (2 g, 14 mmol) was added toluene (60 mL) and the suspension was heated to 80° C. N,N-dimethylformamid-ditertbutylacetal (16.8 mL, 70.3 mmol) was added and the mixture was heated at 80° C. overnight. The mixture was concentrated in vacuo to around 10 mL of total volume and added to diethyl ether (100 mL). The organic phase was washed with water (2×50 mL) followed by washing with aqueous NaHCO3 (10%, 2×50 mL). The organic phase was dried (MgSO$_4$) and the solvent removed in vacuo to yield 1.3 g of 5-methyl-thiophene-2-carboxylic acid tert-butyl ester.

$^1$H NMR (CDCl$_3$): δ 7.52 (d, 1H), 6.73 (d, 1H), 2.50 (s, 3H), 3.60 (q, 2H), 1.56 (s, 9H)

Step 2: Synthesis of 5-Bromomethylthiophene-2-carboxylic Acid tert-butyl Ester

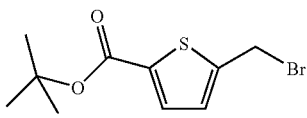

To 5-Methyl-thiophene-2-carboxylic acid tert-butyl ester (10.8 g, 54.5 mmol) was added cyclohexan (100 mL) and N-bromosuccinimide (9.7 g, 54.5 mmol) and was heated at reflux overnight. The suspension was to added ethylacetate (200 mL) and the organic solution was washed with water (4×100 mL). The solvent was removed in vacuo to yield 14.9 g of 5-bromomethylthiophene-2-carboxylic acid tert-butyl ester.

$^1$H NMR (CDCl$_3$): δ 7.61 (d, 1H), 7.02 (d, 1H), 4.66 (s, 2H), 1.67 (s, 9H).

Step 3: Synthesis of (5-tert-Butoxycarbonyl-thiophen-2-ylmethyl)-triphenylphosphonium Bromide

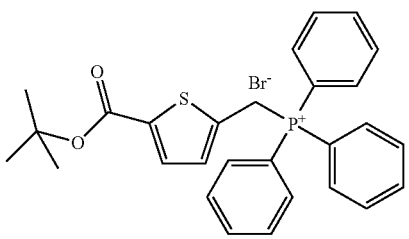 [SMILES: CC(C)(C)OC(=O)c1ccc(C[P+](c2ccccc2)(c2ccccc2)c2ccccc2)s1 ; [Br-]]

To 5-bromomethylthiophene-2-carboxylic acid tert-butyl ester (14.9 mmol, 43.8 mmol) was added toluene (300 mL) and triphenylphosphine (14.1 g, 53.8 mmol). The mixture was heated to 70° C. overnight. The solvent was remove in vacuo to give (5-tert-Butoxycarbonyl-thiophen-2-ylmethyl)-triphenylphosphonium bromide HPLC-MS (Method C): m/z=459; $R_t$=4.65 min.

Step 4: Synthesis of 12-Oxo-dodecanoic Acid Methyl Ester

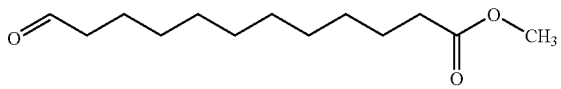 [SMILES: COC(=O)CCCCCCCCCCC=O]

12-Hydroxydecanoic acid (15.25 g, 0.07 mol) was dissolved in methanol (700 mL), aqueous HCl (1N, 10 mL) was added and the mixture was stirred under nitrogen for 16 h, the pH was adjusted to 7.2 with aqueous NaOH (1N). The solvent was removed in vacuo and the remaining compound was separated between ethyl acetate (150 mL) and aqueous NaHCO$_3$ (5%, 150 mL). The organic phase was isolated, dried and the solvent was removed in vacuo to give 12-hydroxydecanoic acid methyl ester as a solid compound. Oxalyl chloride (6.5 mL, 75 mmol) was mixed with in DCM (160 mL), cooled to −60° C. with dry ice/acetone. DMSO (10.7 mL, 151 mmol) was mixed with DCM (20 mL) and added dropwise over 10 minutes. 12-hydroxydecanoic acid methyl ester was dissolved in DCM (50 mL) and added dropwise over 45 minutes. Triethyl amine (47.8 mL, 343 mmol) was added dropwise and a precipitation was observed. After addition of triethylamine the reaction mixture was allowed to reach room temperature. The reaction mixture was washed with water (200 mL) and the water-phase was washed with DCM (3×200 mL) all the organic phases were collected and washed with saturated aqueous NaCl (300 mL), dried (MgSO$_4$) and the solvent was removed in vacuo. The remaining oil was purified on silica eluted with ethyl acetate/heptane (20:80) to yield 11.7 g of 12-oxo-dodecanoic acid methyl ester.

$^1$H NMR (CDCl$_3$): δ 9.76 (s, 1H), 3.66 (s, 3H), 2.42 (t, 2H), 2.30 (t, 2H), 1.66-1.54 (m, 4H), 1.37-1.24 (br s, 14H).

Step 5: Synthesis of 5-(12-Methoxycarbonyl-dodecyl)-thiophene-2-carboxylic Acid tert-butyl ester

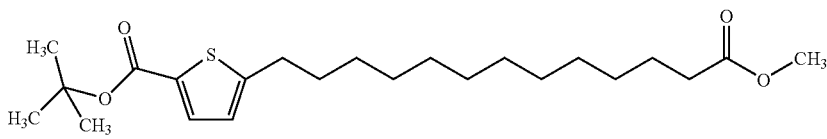 [SMILES: COC(=O)CCCCCCCCCCCCc1ccc(C(=O)OC(C)(C)C)s1]

12-Oxo-dodecanoic acid methyl ester (14.5 g, 63.4 mmol) and (5-tert-butoxycarbonyl-thiophen-2-ylmethyl)-triphenylphosphonium bromide (29.1 g, 63.4 mmol) were dissolved in DMF (350 mL). DBU was added and the mixture was heated to 80° C. for 35 minutes. The reaction mixture was allowed to cool to room temperature and separated between diethyl ether (3×500 mL) and water (2000 mL). The organic phases were collected and washed with water (1×500 mL). The organic phase was dried (MgSO$_4$) and the solvent was removed in vacuo. The remaining crude material was added heptane (300 mL) and stirred for 30 minutes, filtered and the solvent was removed in vacuo to yield 13.6 g of crude material of an E/Z mixture of 5-(12-methoxycarbonyl-dodec-1-enyl)thiophene-2-carboxylic acid tert-butyl ester. This mixture was dissolved in methanol (200 mL). 2 g of 10% Palladium on carbon (50% wet with water) was added and the mixture was stirred under a hydrogen atmosphere with 10 bar pressure for 90 minutes, filtered and the solvent was removed in vacuo to yield 11.6 g of 5-(12-methoxycarbonyl-dodecyl)-thiophene-2-carboxylic acid tert-butyl ester.

$^1$H NMR (CDCl$_3$): δ 7.54 (d, 1H), 6.74 (d, 1H), 3.66 (s, 3H), 2.80 (t, 2H), 2.30 (t, 2H), 1.63 (m, 4H), 1.56 (s, 9H), 1.27 (m, 16H).

Step 6: Synthesis of 5-(12-carboxydodecyl)-thiophene-2-carboxylic acid tert-butyl Ester

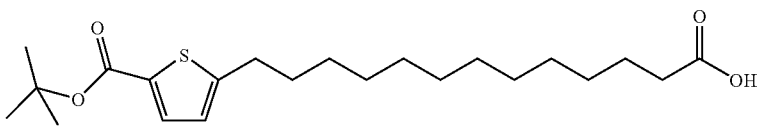 [SMILES: CC(C)(C)OC(=O)c1ccc(CCCCCCCCCCCCC(=O)O)s1]

5-(12-Methoxycarbonyl-dodecyl)-thiophene-2-carboxylic acid tert-butyl ester (75 mg, 0.13 mmol) was dissolved in methanol (2 mL). A 20% solution of NaOH in water (0.36 mL) was added and the mixture was stirred at room temperature for 1 hour. Water (10 mL) was added and the mixture was acidified by the addition of 2 mL of a 10% solution of $NaHSO_4$ in water. The precipitate was isolated by centrifuge and dried in vacuo, to yield 5-(12-carboxydodecyl)-thiophene-2-carboxylic acid tert-butyl ester, which was contaminated with some starting material was used in the subsequent step without any further purification.

HPLC-MS (Method C): m/z=396; $R_t$=6.77 min.

Step 7: Synthesis of B29N(esp)[12-(5-Carboxythiophen-2-yl)dodecanoyl] desB30 Insulin 5-(12-Carboxydodecyl)-thiophene-2-carboxylic acid tert-butyl ester was activated by TSTU and acylated on DesB30 human insulin followed by removal of the tert-butyl protecting group with TFA and subsequent purification using procedures similar to what has been described in example 7.

HPLC-MS (Method C): m/z=1508 (m/4); $R_t$=4.88 min.

Example 7

$N^{\epsilon 29}$-[12-(5-Carboxythiophen-2-yl)dodecanoyl-γGlu] desB30 Insulin 5-(12-carboxydodecyl)-thiophene-2-carboxylic acid tert-butyl ester (31 mg, 0.078 mmol) was treated with TSTU (28.2 mg, 0.094 mmol) and DIPEA (0.016 mL, 0.094 mmol) in THF (1.3 mL) for 2½ hours at room temperature under nitrogen. The solvent was removed in vacuo and the mixture added NMP (1 mL) and H-Glu-OtBu (31.3 mg, 0.154 mmol) and DIPEA (0.027 mL). The mixture was stirred overnight at room temperature. The mixture was separated between diethyl ether (10 mL) and 10% aqueous NaHSO4 (2×10 mL) and the organic phase isolated and solvent removed in vacuo to give the crude (S)-2-[13-(5-tert-Butoxycarbonylthiophen-2-yl)-tridecanoylamino]-pentanedioic acid 1-tert-butyl ester which was subsequently in the next step without any further purification.

HPLC-MS (Method C): m/z=582; $R_t$=8.1 min.

Step 2: Synthesis of $N^{\epsilon B29}$-[12-(5-Carboxythiophen-2-yl)dodecanoyl-Y-Glu] desB30 Insulin Human DesB30 insulin (294 mg, 0.051 mmol) was dissolved in DMSO (3.5 mL). Triethyl amine (0.071 mL, 0.51 mmol) was added.

The (S)-2-[13-(5-tert-Butoxycarbonylthiophen-2-yl)-tridecanoylamino]-pentanedioic acid 1-tert-butyl ester (45.4 mg, 0.078 mmol) was activated with TSTU similar as described above. Dissolved in DMSO (0.5 mL) and added to the insulin solution. This mixture was stirred carefully for 30 minutes at room temperature. Cooled with an icebath (solu-

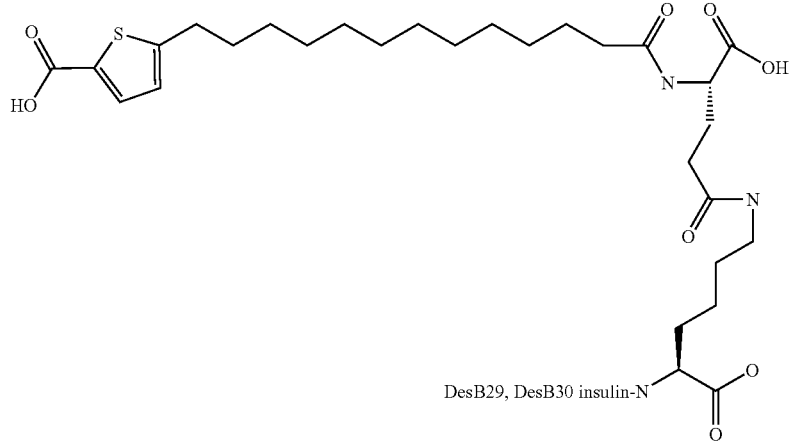

tion freezes). 8 mL of water is added and the solution stand until the frozen mixture has dissolved. The pH is adjusted to 5.3 with 1N aqueous HCl and the precipitate isolated by centrifuge. The isolated compound is treated with a mixture if

Step 1: Synthesis of (S)-2-[13-(5-tert-Butoxycarbonylthiophen-2-yl)-tridecanoylamino]-pentanedioic Acid 1-tert-butyl Ester

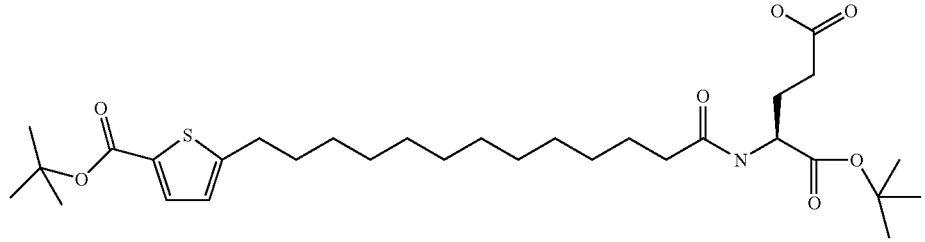 [SMILES: CC(C)(C)OC(=O)c1ccc(CCCCCCCCCCCCC(=O)N[C@@H](CCC(=O)O)C(=O)OC(C)(C)C)s1]

97.5% TFA and 2.5% thiophene for 30 minutes, poured into diethyl ether (50 mL). The crude product was isolated by filtration and purified similar as described above.

HPLC-MS (Method C): m/z=1549 (m/4); 1232 (m/5) $R_t$=3.5 min.

Example 8

Hydrophobicity Receptor Affinity, Albumin Affinity and Self-Association

Analysis of self-associating properties of the insulin derivatives of the invention The ability of the insulin derivatives of the invention to self-associate into large, but soluble complexes is analysed using SEC (size exclusion chromatography):

| | |
|---|---|
| Column: | Superose ™ 6 PC 3.2/30, CV = 2.4 ml (Amerham Biosciences) |
| Temperature: | 37° C. |
| SEC buffer: | 140 mM NaCl, 10 mM TrisHCl, 0.01% NaN$_3$, pH 7.5 |
| Injection volume: | 20 µl |
| Flow: | 0.05 ml/min |
| Runtime: | 60 min and equillibration of additional 100 min |

For this analysis the insulin derivatives of the invention are in a solution consisting of 0.6 mM derivative, 2.1 Zn$^{2+}$/hexamer, 16 mM phenol, 7 mM phosphate pH 7.8. The retention time of the derivative is then compared to the retention times of the following standard molecules:

| | | |
|---|---|---|
| Standard I: | HSA + HSA dimer | (66.4 kDa + 133 kDa) |
| | Co(III)insulin hexamer | (35.0 kDa) |
| | X2 insulin monomer | (5.9 kDa) |
| Standard II: | Blue dextran | (1.5 MDa) |
| | Thyroglobulin | (669 kDa) |
| | Ferritin | (440 kDa) |
| | Aldolase | (158 kDa) |
| | Ovalbumin | (44.5 kDa) |
| | Ribonuclease | (13.7 kDa) |

The following equation is used to determine the $K_{av}$ for the derivative:

$$K_{av} = (t-t_0)/(V_t/(f+t_d-t_0))$$

Where t is the retention time for a given peak, $t_0$ is the retention time for Blue dextran, $V_t$ is the total column volume (here 2.4 ml), f is the flow (here 0.04 ml/min), and $t_d$ is the retention time for Blue dextran without the column in the system. The $K_{av}$ value indicates the degree of self-association of a derivative, i.e. a large $K_{av}$ similar to the $K_{av}$ for the Co(III) insulin hexamer and X2 insulin monomer shows low or no propensity of the derivative to form large, Self-associated complexes, while very small $K_{av}$ close to zero or even negative shows great propensity of the derivative for self-association into large, soluble complexes.

Hydrophobicity Data on Insulin Derivatives According to the Invention

The hydrophobicity (hydrophobic index) of the insulin derivatives of the invention relative to human insulin, $k'_{rel}$, was measured on a LiChrosorb RP18 (5 µm, 250×4 mm) HPLC column by isocratic elution at 40° C. using mixtures of A) 0.1 M sodium phosphate buffer, pH 7.3, containing 10% acetonitrile, and B) 50% acetonitrile in water as eluents. The elution was monitored by following the UV absorption of the eluate at 214 nm. Void time, $t_0$, was found by injecting 0.1 mM sodium nitrate. Retention time for human insulin, $t_{human}$, was adjusted to at least 2 $t_0$ by varying the ratio between the A and B solutions. $k'_{rel}=(t_{derivative}-t_0)/(t_{human}-t_0)$. $k'_{rel}$ found for a number of insulin derivatives according to the invention are given in Table 1.

Human Serum Albumin Affinity Assay

Relative binding constant of 125I-TyrA14-analogue to human serum albumin immobilised on Minileak particles and measured at 23° C. (detemir=1 in saline buffer)

| Compound | Hydrophobicity relative to human insulin | Insulin receptor affinity relative to human insulin | Human serum albumin affinity relative to insulin detemir | Self-association: $K_{av}$ (% area of peak) |
|---|---|---|---|---|
| Example 1 | +++<br>0.73 | ++<br>17% | n.a. | +++<br>0 (95%) |
| Example 2 | +++<br>0.52 | ++<br>44% | +<br>0.21 | +++<br>0.02 (58%) |
| Example 3 | +++<br>0.72 | ++<br>18% | ++<br>0.82 | ++<br>0.15 (64%) |
| Example 4 | +++<br>0.44 | ++<br>37% | ++<br>0.84 | +++<br>0.04 (76%) |
| Example 5 | ++<br>1.8 | ++<br>43 | +<br>0.33 | ++<br>0.26 (48%) |
| Example 6 | ++<br>2.8 | ++<br>29 | n.a. | n.a. |

Hydrophobicity relative to human insulin: k'rel <1: +++, 1-10: ++, >10: + (HI = 1)
Insulin receptor affinity relative to human insulin: <5%: +, 5-50%: ++, >50%: +++
Human serum albumin affinity relative to insulin detemir: <0.5: +, 0.5-2: ++, >2: +++
Self-association: $K_{av}$ < 0.1: +++, $K_{av}$ < 0.55: ++ and $K_{av}$ ≥ 0.55: +
$K_{av}$ = 0.55 for human serum albumin, $K_{av}$ = 0.63 for human insulin Co(III)hexamer, $K_{av}$ = 0.72 for the monomeric insulin analogue X2.
n.a = not analyzed.

Pharmacological Methods

Assay (I)

Insulin Receptor Binding of the Insulin Derivatives of the Invention

The affinity of the insulin analogues of the invention for the human insulin receptor was determined by a SPA assay (Scintillation Proximity Assay) microtiterplate antibody capture assay. SPA-PVT antibody-binding beads, anti-mouse reagent (Amersham Biosciences, Cat No. PRNQ0017) were mixed with 25 ml of binding buffer (100 mM HEPES pH 7.8; 100 mM sodium chloride, 10 mM MgSO$_4$, 0.025% Tween-20). Reagent mix for a single Packard Optiplate (Packard No. 6005190) is composed of 2.4 µl of a 1:5000 diluted purified recombinant human insulin receptor—exon 11, an amount of a stock solution of A14 Tyr[$^{125}$I]-human insulin corresponding to 5000 cpm per 100 µl of reagent mix, 12 µl of a 1:1000 dilution of F12 antibody, 3 ml of SPA-beads and binding buffer to a total of 12 ml. A total of 100 µl was then added and a dilution series is made from appropriate samples. To the dilution series was then added 100 µl of reagent mix and the samples were incubated for 16 hours while gently shaken. The phases were the then separated by centrifugation for 1 min and the plates counted in a Topcounter. The binding data were fitted using the nonlinear regression algorithm in the GraphPad Prism 2.01 (GraphPad Software, San Diego, Calif.).

Preparation of Monoclonal mIR Antibodies

Specific antibodies (F12) were produced by monoclonal technique: RBF mice were immunized by injecting 50 µg of purified mIR in FCA subcutaneously followed by two injections with 20 µg of mIR in FIA. Highresponder mice were boosted intravenously with 25 µg of mIR and the spleens were harvested after 3 days. Spleen cells were fused with the myeloma Fox cell line (Köhler, G & Milstein C. (1976), European J. Immunology, 6:511-19; Taggart R T et al (1983), Science 219:1228-30). Supernatants were screened for antibody production in a mIR specific ELISA. Positive wells were cloned and tested in Western blotting.

Assay (II)

Potency of the Insulin Derivatives of the Invention Relative to Human Insulin

Sprague Dawley male rats weighing 238-383 g on the experimental day were used for the clamp experiment. The rats had free access to feed under controlled ambient conditions and were fasted overnight (from 3 μm) prior to the clamp experiment.

Experimental Protocol

The rats were acclimatized in the animal facilities for at least 1 week prior to the surgical procedure. Approximately 1 week prior to the clamp experiment Tygon catheters were inserted under halothane anaesthesia into the jugular vein (for infusion) and the carotid artery (for blood sampling) and exteriorized and fixed on the back of the neck. The rats were given Streptocilin vet. (Boehringer Ingelheim; 0.15 ml/rat, i.m.) post-surgically and placed in an animal care unit (25° C.) during the recovery period. In order to obtain analgesia, Anorphin (0.06 mg/rat, s.c.) was administered during anaesthesia and Rimadyl (1.5 mg/kg, s.c.) was administered after full recovery from the anaesthesia (2-3 h) and again once daily for 2 days.

The clamp technique employed was adapted from (1). At 7 am on the experimental day overnight fasted (from 3 μm the previous day) rats were weighed and connected to the sampling syringes and infusion system (Harvard 22 Basic pumps, Harvard, and Perfectum Hypodermic glass syringe, Aldrich) and then placed into individual clamp cages where they rested for ca. 45 min before start of experiment. The rats were able to move freely on their usual bedding during the entire experiment and had free access to drinking water. After a 30 min basal period during which plasma glucose levels were measured at 10 min intervals, the insulin derivative to be tested and human insulin (one dose level per rat, n=6-7 per dose level) were infused (i.v.) at a constant rate for 300 min. Plasma glucose levels were measured at 10 min intervals throughout and infusion of 20% aqueous glucose was adjusted accordingly in order to maintain euglyceamia. Samples of re-suspended erythrocytes were pooled from each rat and returned in about ½ ml volumes via the carotid catheter.

On each experimental day, Samples of the solutions of the individual insulin derivatives to be tested and the human insulin solution were taken before and at the end of the clamp experiments and the concentrations of the peptides were confirmed by HPLC. Plasma concentrations of rat insulin and C-peptide as well as of the insulin derivative to be tested and human insulin were measured at relevant time points before and at the end of the studies. Rats were killed at the end of experiment using a pentobarbital overdose.

Test compounds and doses: Insulins to be tested were diluted from a stock solution containing 97 μM of the insulin derivative in 5 mM phosphate pH 7.7. The final concentration in the solution ready for use was 0.45 μM of the insulin derivative, 5 mM of phosphate, 100 mM of sodium chloride, 0.007% of polysorbate 20. The pH was 7.7 and the i.v. infusion rate was 15 and 20 pmol·min$^{-1}$·kg$^{-1}$.

A stock solution of human insulin that was used as reference compound was formulated in a similar medium and infused i.v. at 6, 15 or 30 pmol·min$^{-1}$·kg$^{-1}$.

Both stock solutions were stored at −20° C. and thawed overnight at 4° C. before use. The solutions were gently turned upside down several times 15 min before they were transferred to the infusion syringes.

Assay (III)

Determination in Pigs of $T_{50\%}$ of the Insulin Derivatives of the Invention $T_{50\%}$ is the time when 50% of an injected amount of the A14 Tyr[$^{125}$I] labelled derivative of an insulin to be tested has disappeared from the injection site as measured with an external γ-counter.

The principles of laboratory animal care are followed, Specific pathogen-free LYYD, non-diabetic female pigs, cross-breed of Danish Landrace, Yorkshire and Duroc, are used (Holmenlund, Haarloev, Denmark) for pharmacokinetic and pharmacodynamic studies. The pigs are conscious, 4-5 months of age and weighing 70-95 kg. The animals fast overnight for 18 h before the experiment.

Formulated preparations of insulin derivatives labelled in Tyr$^{A14}$ with $^{125}$I are injected sc. in pigs as previously described (Ribel, U., Jørgensen, K, Brange, J. and Henriksen, U. The pig as a model for subcutaneous insulin absorption in man. Serrano-Rios, M. and Lefèbvre, P. J. 891-896.1985. Amsterdam; New York; Oxford, Elsevier Science Publishers. 1985 (Conference Proceeding)).

At the beginning of the experiments a dose of 60 nmol of the insulin derivative according to the invention (test compound) and a dose of 60 nmol of insulin detemir (both $^{125}$I labelled in Tyr A14) are injected at two separate sites in the neck of each pig.

The disappearance of the radioactive label from the site of sc. injection is monitored using a modification of the traditional external gamma-counting method (Ribel, U. Subcutaneous absorption of insulin analogues. Berger, M. and Gries, F. A. 70-77 (1993). Stuttgart; New York, Georg Thime Verlag (Conference Proceeding)). With this modified method it is possible to measure continuously the disappearance of radioactivity from a subcutaneous depot for several days using cordless portable device (Scancys Laboratorieteknik, Værløse, DK-3500, Denmark). The measurements are performed at 1-min intervals, and the counted values are corrected for background activity.

The invention claimed is:

1. An insulin derivative having a formula

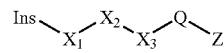

wherein Ins is a parent insulin and $X_1$—$X_2$—$X_3$—Q—Z is a substituent and where the Ins is attached to the substituent via an amide bond between the α-amino group of the N-terminal amino acid residue of the B chain of Ins or an e-amino group of a Lys residue present in the A or B chain of Ins and a CO-group in $X_1$, $X_2$ or $X_3$ of the substituent;

$X_1$ is:
- —CO—$(CH_2)_n$ where n is 1, 2, 3, 4, 5 or 6;
- —CO—$((CR^6R^7)_q$—NR—CO$)_{1-4}$—, where $R^6$ and $R^7$ independently of each other and independently for each value of q can be hydrogen, $C_{1-6}$-alkyl, $C_{2-6}$-alkenyl, $C_{2-6}$-alkynyl, —$(CH_2)_{1-6}$—COOH; —$(CH_2)_{1-6}$—CONH$_2$, —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H, q is 1-6 and R is hydrogen, —$(CH_2)_{1-6}$—COOH; —$(CH_2)_{1-6}$—CONH$_2$; —$(CH_2)_{1-6}$—SO$_3$H; —$(CH_2)_{1-6}$—PO$_3$H$_2$; —$(CH_2)_{1-6}$—O—SO$_3$H$_2$; —$(CH_2)_{1-6}$—O—PO$_3$H$_2$; $C_{1-6}$-alkyl, $C_{2-6}$-alkenyl; $C_{2-6}$-alkynyl or aryl or $CH_2$-aryl, in which the aryl group may be substituted with 1 or 2 groups selected from group consisting of —COOH, —CH$_3$, —SO$_3$H, —(CH$_2$)$_{1-6}$—SO$_3$H, —PO$_3$H$_2$, —(CH$_2$)$_{1-6}$—O—PO$_3$H$_2$, tetrazol-5-lyl or CONH$_2$, C$_{1-6}$-alkyl, C$_{2-6}$-alkenyl, C$_{2-6}$-alkynyl, hydrogen, halogen, —CN, —CF$_3$, —OCF$_3$, —S(O)$_2$CF$_3$, —SCF$_3$, —NO$_2$, —OR$^2$, —SR$^2$, —NR$^2$S(O)$_2$R$^3$, —S(O)$_2$NR$^2$R$^3$, —S(O)NR$_2$R$^3$, —S(O)R$^2$, —S(O)$_2$R$^2$, —C(O)NR$^2$R$^3$, —OC(O)NR$^2$R$^3$, —NR$^2$C(O)R$^3$, —CH$_2$C(O)NR$^2$R$^3$, —OCH$_2$C(O)NR$^2$R$^3$, —OC(O)R$^2$, —OCH$_2$C(O)R$^2$, —C(O)R$^2$ or —C(O)OR$^2$ or —OCH$_2$C(O)OR$^2$, where R$^2$ and R$^3$ independently are hydrogen, C$_{1-6}$-alkyl, C$_{2-6}$-alkenyl or C$_{2-6}$-alkynyl;

an amino acid amide residue of an amino acid with carboxylic acid in the side chain, or an amino acid with an uncharged side chain, or an amino acid with negatively charged side chain, which residue forms, with its carboxylic acid group, an amide bond together with the a-amino group of the N-terminal amino acid residue of the B chain of Ins or together with the e-amino group of a Lys residue present in the A or B chain of Ins;

a chain composed of two, three or four residues linked together via amide bonds in which the residues are chosen from the group consisting of: a-amino acid amide residues and amino acid residues as specified above, in which the chain—via an amide bond—is linked to the a-amino group of the N-terminal amino acid residue of the B chain of Ins or to the e-amino group of a Lys residue present in the A or B chain of Ins; or a bond;

X$_2$ is:

—CO—;

—COCH(R$^8$)—;

—COCH$_2$N(CH$_2$R$^8$)—;

—COCH$_2$N(CH$_2$RS)COCH$_2$N(CH$_2$R$_8$)—;

—COCH$_2$CH$_2$N(CH$_2$CH$_2$R$^8$)—;

—COCH$_2$CH$_2$N(CH$_2$CH$_2$RS)—COCH$_2$CH$_2$N(CH$_2$CH$_2$R$^8$)—;

—COCH$_2$N(CH$_2$CH$_2$RS)—;

—COCH$_2$CH$_2$N(CH$_2$RS)— where R$^8$ can be COOH or CONH$_2$;

—CO—((CH$_2$)$_{2-6}$—NH—CO)$_{1-4}$—;

—(CO—(CH$_2$)$_{2-6}$—CO—NH)$_{1-4}$—;

—(CO—(CR$^9$R$^{10}$)$_{1-6}$—CO—NH))$_{1-4}$—, where R$^9$ can be H, —COOH, —(CH$_2$)$_{1-6}$COOH, CH$_3$, —(CH$_2$)$_{1-6}$CH$_3$ or CONH$_2$ and R$^{10}$ can be H, —(CH$_2$)$_{1-6}$COOH, CH$_3$ or —(CH$_2$)$_{1-6}$CH$_3$; or a bond;

provided that if an amine in X$_1$ or X$_2$ forms a bond with the rest of the substituent, the amine must be bound to the rest of the substituent via a carbonyl group;

X$_3$ is —C=O, provided that X$_3$ is only present if X$_1$ and X$_2$ are bonds;

Q is a chain of the formula —(CH$_2$)$_{s1}$-Q$_1$-(CH$_2$)$_{s2}$-Q$_2$-(CH$_2$)$_{s3}$-Q$_3$-(CH$_2$)$_{s4}$-Q$_4$-(CH$_2$)$_{s5}$—; wherein Q$_1$, Q$_2$ and Q$_3$ are all bonds, Q$_4$ is C$_6$H$_4$, S2, S3 and s4 are all one, S1 is 5, 6, 7 or 8 and s5 is 0, 1 or 2;

and

Z is:

—COOH;

—CO-Asp;

—CO-Glu;

—CO-Gly;

—CO-Sar;

—CH(COOH)$_2$;

—N(CH$_2$COOH)$_2$;

—SO$_3$H;

—PO$_3$H$_2$;

O—SO$_3$H;

O—PO$_3$H$_2$; or tetrazo-5-lyl;

and any Zn$^{2+}$ complex thereof.

2. The insulin derivative according to claim 1, wherein X$_1$ is selected from the group consisting of β-D-Asp-amide, β-L-Asp-amide, γ-L-Glu-amide and γ-D-Glu-amide.

3. The insulin derivative according to claim 1, wherein X$_2$ is a bond.

4. The insulin derivative according to claim 1, wherein X$_2$ is selected from the group consisting of —(CO—(CH$_2$)$_2$—NH—CO)$_1$—, —(CO—(CH$_2$)$_3$—NH—CO)$_1$—, —CO— or —COCH(COOH)—.

5. The insulin derivative according to claim 1, wherein X$_1$ is a bond.

6. The insulin derivative according to claim 1, wherein Z is COOH.

7. The insulin derivative according to claim 1, wherein the parent insulin is desB30 human insulin.

8. A pharmaceutical composition for the treatment of diabetes in a patient in need of such treatment, comprising a therapeutically effective amount of an insulin derivative according to claim 1 optionally together with a pharmaceutically acceptable carrier.

9. A method of treating diabetes in a patient in need of such treatment, comprising administering to the patient a therapeutically effective amount of an insulin derivative according to claim 1 optionally together with a pharmaceutically acceptable carrier.

10. The method according to claim 9 for pulmonary treatment of diabetes.

11. The insulin derivative according to claim 1 selected from the group consisting of:

N$^{\epsilon B29}$-(12-(4-carboxyphenyl) dodecanoyl-γ-Glu) desB30 insulin,

N$^{\epsilon B29}$-(-11-(4-carboxyphenyl) undecanoyl γ-Glu) desB30 insulin,

N$^{\epsilon B29}$-(12-(3-carboxyphenyl) dodecanoyl γ-Glu desB30 insulin,

N$^{\epsilon B29}$-(9-[4-(2-carboxyethyl)phenyl]nonanoyl) γ-Glu) desB30 insulin, and N$^{\epsilon B29}$-(4-[11-(4-carboxyphenyl)undecanoylamino]butyryl) desB30 insulin.

* * * * *

UNITED STATES PATENT AND TRADEMARK OFFICE
CERTIFICATE OF CORRECTION

PATENT NO.         : 8,796,205 B2
APPLICATION NO.    : 12/297914
DATED              : August 5, 2014
INVENTOR(S)        : Ib Jonassen et al.

It is certified that error appears in the above-identified patent and that said Letters Patent is hereby corrected as shown below:

In the Claims:

At column 71, claim number 1, beginning at line number 2, please amend the line as follows:

"...—$PO_3H_2$, –$(CH_2)_{1-6}$–O –$PO_3H_2$, tetrazo –5 –lyl or..."

At column 71, claim number 1, beginning at line number 6, please amend the line as follows:

"...$R^3$, –$S(O)_2NR^2R^3$, $S(O)NR^2R^3$, –$S(O)R^2$,..."

At column 71, claim number 1, beginning at line number 39, please amend the line as follows:

"...—$COCH_2N(CH_2R^8)COCH_2N(CH_2R^8)$—;..."

At column 71, claim number 1, beginning at line number 41, please amend the line as follows:

"...—$COCH_2CH_2N(CH_2CH_2R^8)$—$COCH_2CH_2N(CH_2CH_2R^8)$—;..."

At column 71, claim number 1, beginning at line number 44, please amend the line as follows:

"...—$COCH_2N(CH_2CH_2R^8)$—;..."

Signed and Sealed this
Third Day of March, 2015

Michelle K. Lee
*Deputy Director of the United States Patent and Trademark Office*

CERTIFICATE OF CORRECTION (continued)
U.S. Pat. No. 8,796,205 B2

At column 71, claim number 1, beginning at line number 46, please amend the line as follows:

"...—$COCH_2CH_2N(CH_2R^8)$—..."